United States Patent [19]
Furukawa

[11] Patent Number: 5,522,799
[45] Date of Patent: Jun. 4, 1996

[54] FLUID INFUSION PUMP CAPABLE OF DETECTING ERRONEOUS TUBE DISPLACEMENT

[75] Inventor: Toshio Furukawa, Nara, Japan

[73] Assignee: Sharp Kabushiki Kaisha, Osaka, Japan

[21] Appl. No.: 356,860

[22] Filed: Dec. 15, 1994

[30] Foreign Application Priority Data

Dec. 17, 1993 [JP] Japan .................... 5-318056

[51] Int. Cl.$^6$ ................................ A61M 31/00
[52] U.S. Cl. ............... 604/65; 604/67; 128/DIG. 12; 128/DIG. 13
[58] Field of Search ................ 604/62, 65, 66, 604/67, 153; 128/DIG. 12, DIG. 13

[56] References Cited

U.S. PATENT DOCUMENTS

| | | | |
|---|---|---|---|
| 4,648,812 | 3/1987 | Kobayashi et al. | 417/477 |
| 4,671,792 | 6/1987 | Borsanyi | 604/153 |
| 4,731,057 | 5/1988 | Tanaka et al. | 604/153 |
| 5,018,945 | 5/1991 | D'Silva | 417/12 |
| 5,279,556 | 1/1994 | Goi et al. | 604/67 |
| 5,312,334 | 5/1994 | Hara | 605/65 |
| 5,356,378 | 11/1994 | Doan | 604/65 |
| 5,370,612 | 12/1994 | Maeda et al. | 604/67 |
| 5,389,071 | 2/1995 | Kawahara | 604/51 |

FOREIGN PATENT DOCUMENTS

| | | |
|---|---|---|
| 3-205060 | 9/1991 | Japan . |
| 60171241 | 1/1993 | Japan . |

Primary Examiner—Corrine M. Maglione
Assistant Examiner—Anh-Tuan T. Nguyen
Attorney, Agent, or Firm—David G. Conlin; Milton Oliver

[57] ABSTRACT

A pressure sensor 16 has a length C and a width D identical respectively to a length A and a width B of a fluid pumping section 11 and is provided in a portion of a cover 15 opposite to the fluid pumping section 11. The fluid pumping section 11 has a structure for pressing a tube placed in a groove 13 by means of fingers which advance and retract in a cavity 14 formed in a wall 12 of a main body. A possible erroneous placement of the tube is detected according to a change of pressure force exerted from each of the fingers, detected by the pressure sensor 16. The pressure sensor 16, which is provided within a range in which the fingers can press the tube, can detect even a slight displacement, of the tube from the range in which the fingers can press the tube, to thereby allow detection of erroneous tube placement free of a dead zone to be achieved.

16 Claims, 25 Drawing Sheets

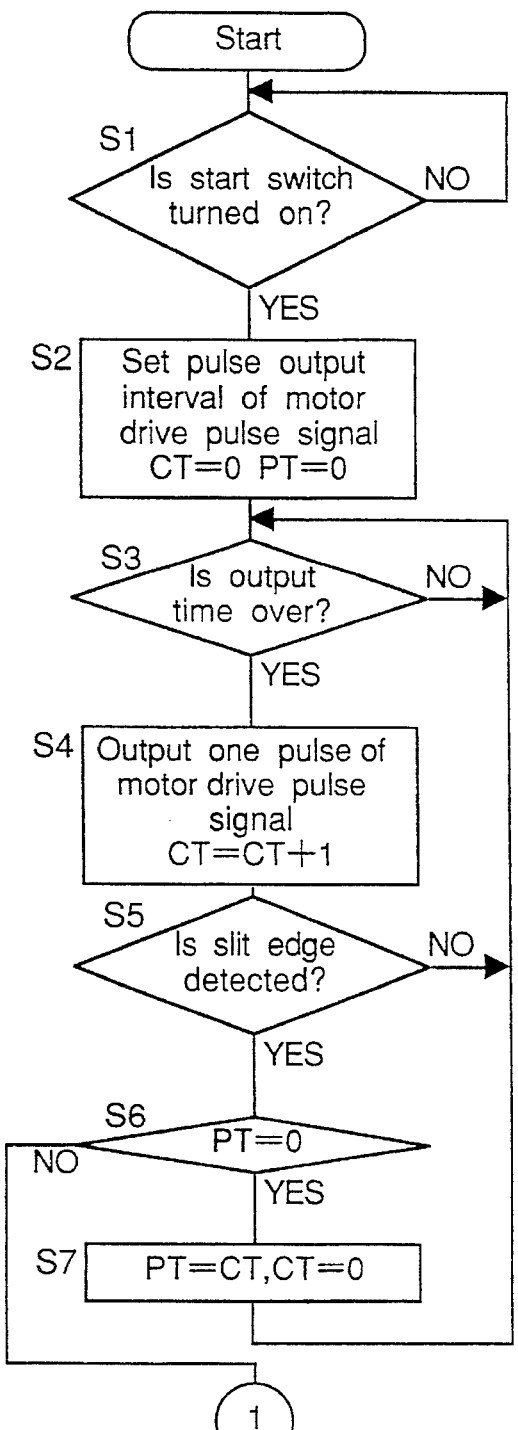
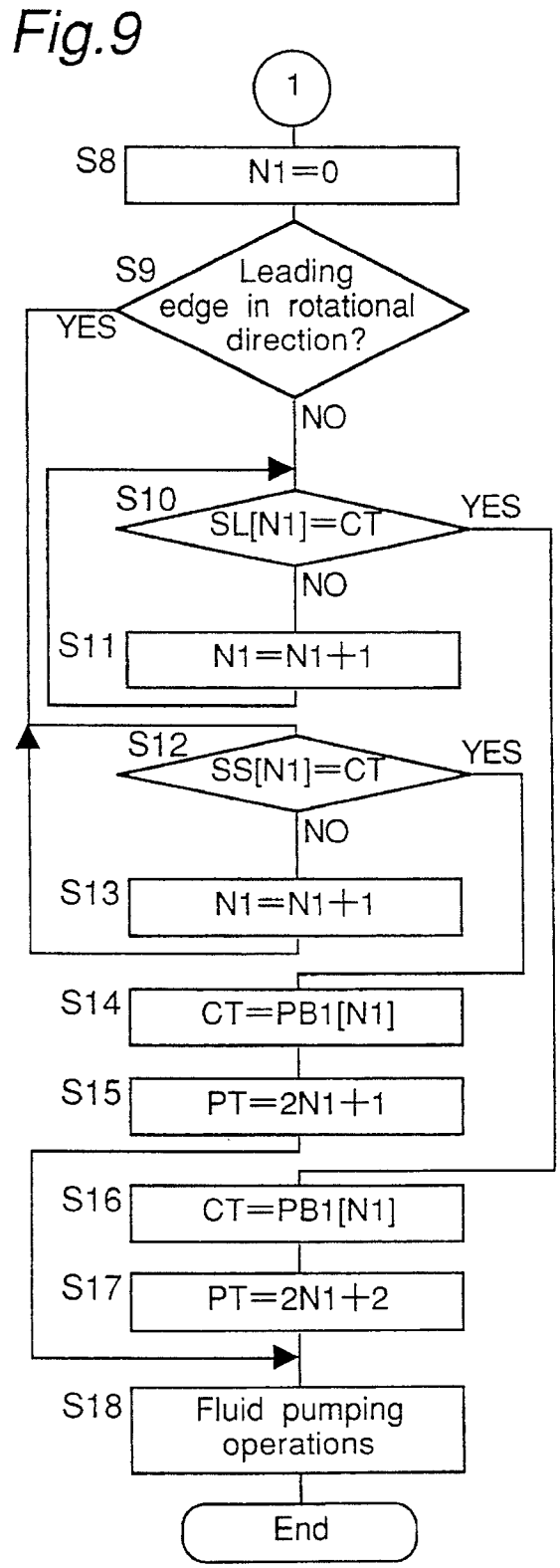
Fig.9

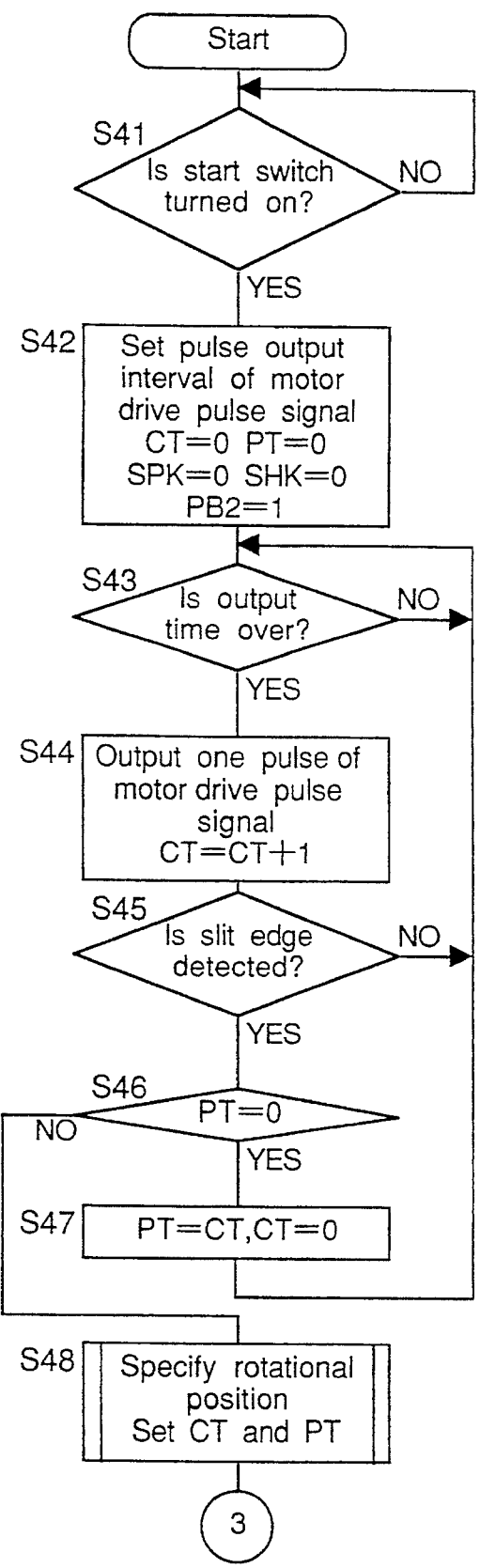
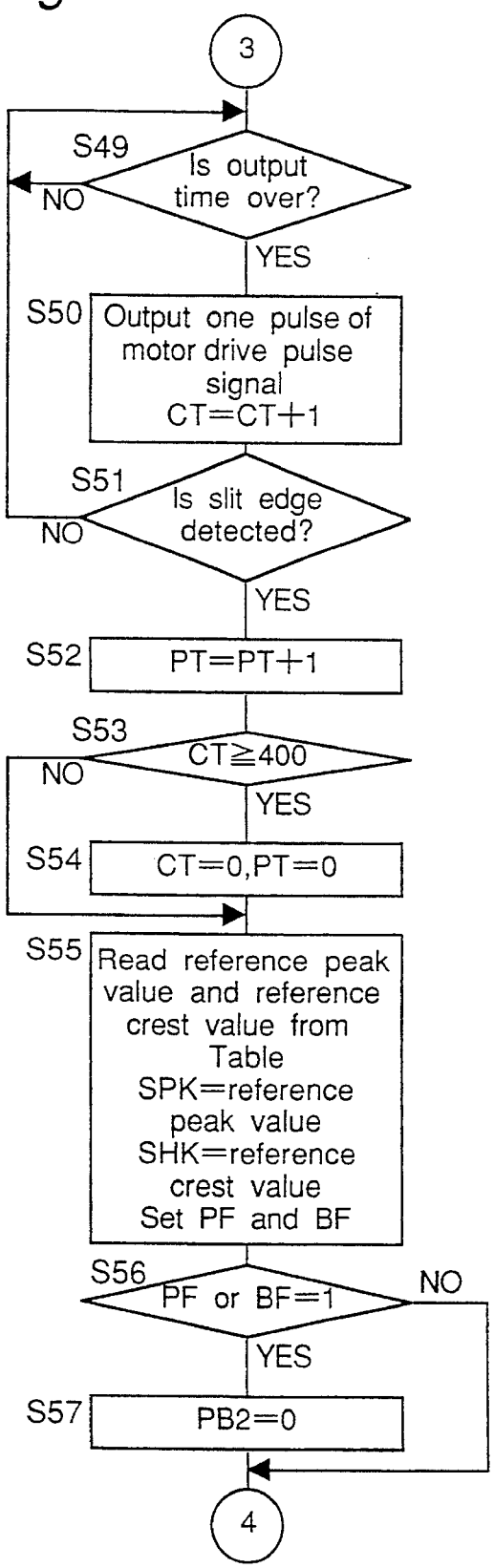
Fig. 11

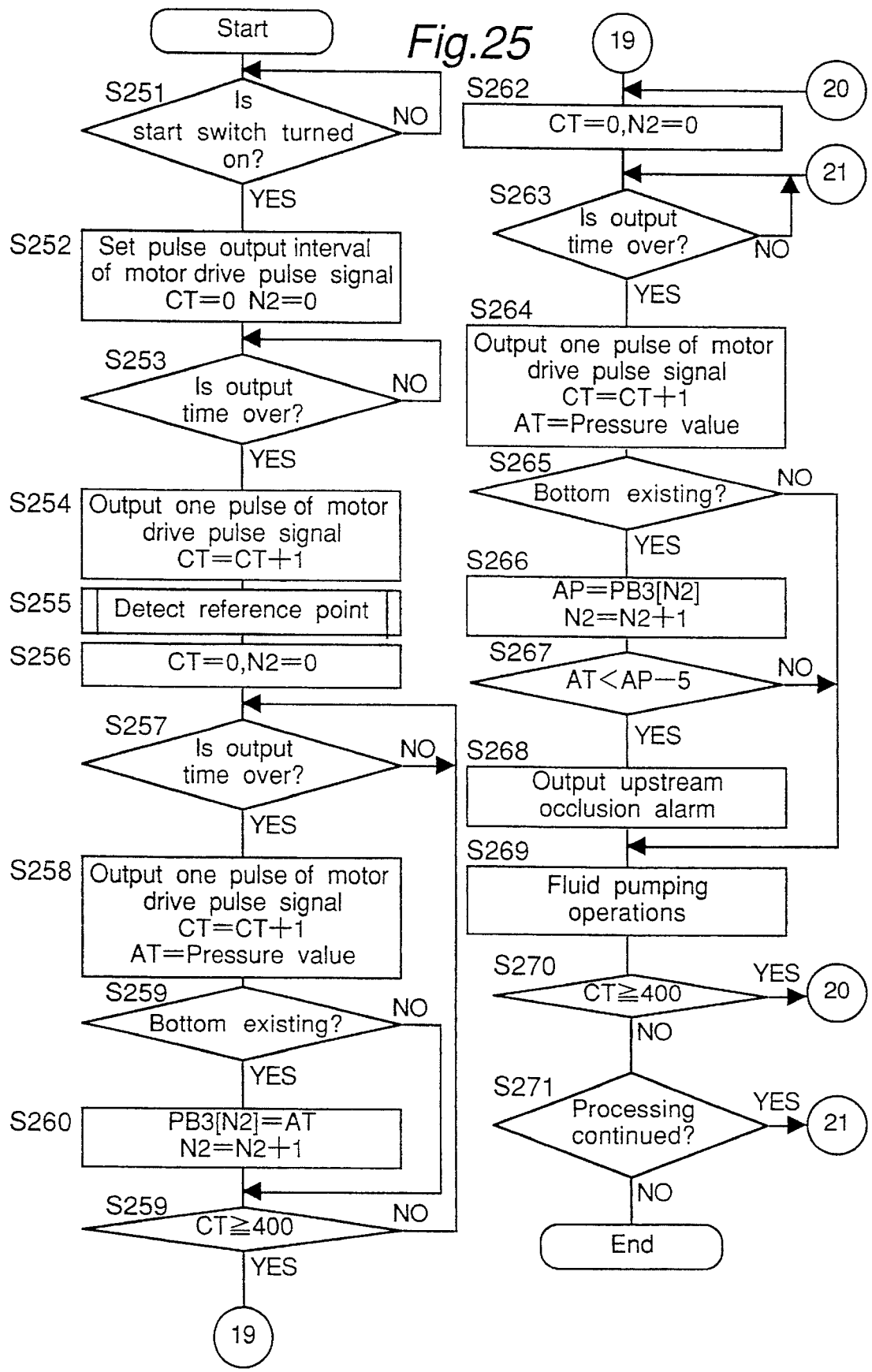

FLUID INFUSION PUMP CAPABLE OF DETECTING ERRONEOUS TUBE DISPLACEMENT

BACKGROUND OF THE INVENTION

1. Field of the Invention

The present invention relates to a fluid infusion pump which peristaltically presses a tube to transfer a fluid in the tube.

2. Description of the Prior Art

A linear peristaltic system fluid infusion pump has its fluid pumping section approximately composed of a groove formed in a wall in which a tube is placed, a plurality of fingers in a stack for peristaltically occluding the tube placed in the groove so that an occluded portion of the tube moves in one direction, and cams for driving the fingers. By advancing and retracting the fingers with respect to the tube while providing a phase shift between adjacent fingers by means of the corresponding cams, the tube is peristaltically occluded sequentially in one direction.

The above-mentioned type of fluid infusion pump is provided with a variety of detection means and control means as follows.

(1) Erroneous tube placement detection

As shown in FIG. 26, pressure sensors 3 are provided on both sides of a cavity 2 in which the aforementioned fingers (not shown) of a fluid pumping section 1 advance and retreat. When a tube is placed in a groove 4, the tube is displaced onto either of the pressure sensors 3, with which a detection value obtained from the pressure sensor 3 varies, to permit detections of the fact that the tube is erroneously placed.

(2) Downstream occlusion detection

By providing a pressure sensor on the downstream side of the fluid pumping section, or by separating the fluid pumping section into an upstream side and a downstream side and providing a pressure sensor at the boundary between the upstream side and the downstream side, a downstream occlusion is detected by a pressure increase on the downstream side (on the fluid delivery side). It is to be noted that the downstream occlusion is detected by a pressure sensor different from the pressure sensor for the erroneous tube placement detection.

(3) Upstream occlusion detection

By providing a pressure sensor on the upstream side of the fluid pumping section, or by separating the fluid pumping section into an upstream side and a downstream side and providing a pressure sensor at the boundary between the upstream side and the downstream side, an upstream occlusion is detected by a pressure increase on the upstream side (on the fluid supply side). It is to be noted that the upstream occlusion is detected by a pressure sensor different from the pressure sensor for the erroneous tube placement detection.

(4) Motor rotational position detection

By providing an encoder comprised of a rotation detecting disk which is provided at an end portion of a shaft around which the cams are mounted and is provided with slits formed at regular intervals and a photosensor, a rotational position with respect to a reference point is detected by means of light travelling through the slits. Otherwise, by driving the shaft by means of a pulse motor, a rotational position with respect to the reference point is detected by the amount of pulses applied to the pulse motor in one rotation of the shaft from the reference point obtained from the photosensor.

When the finger in the lowermost position among the fingers in a stack is pressing the tube, the content volume of the tube does not change, and the outlet of the fluid pumping section is occluded to transfer no medication fluid (dead band). Therefore, it has been performed to preparatorily detect the period of the dead band from the rotational position of the motor detected in a manner as described above, and control the speed of the motor in the period.

(5) Driving torque control (control of current applied to the motor)

A driving torque in a required phase is controlled according to the phase with respect to the reference point detected in the item (4). When controlling the current applied to the motor, the motor input current is reduced in steps. In the case where, when the amount of pulses to be supplied to a stepping motor is set greater than the amount of pulses to be supplied in the slit passage time of the rotation detecting disk, no change occurs in the amount of pulses counted when the slits pass (i.e., slit passage time), it is decided that a stepout (a condition in which the motor is at idle due to a shortage of motor torque) is occurring, and therefore the motor input current is increased.

Unfortunately, there are problems as follows in the detection means and the control means of the aforementioned fluid infusion pump.

(A) Erroneous tube placement detection

Since the erroneous placement of the tube is detected according to the change of the detection value obtained from the pressure sensors 3 provided on both sides of the fluid pumping section 1 as described in regard to the item (1), the pressure sensors 3 are required to have a waterproof structure. Therefore, it is required to provide a sealing section having a thickness slightly greater than 1 mm at each of the pressure sensors 3. Furthermore, it is very difficult to arrange the pressure sensors 3 close to the cavity 2 of the fluid pumping section 1 leaving no space between them, and therefore each of the pressure sensors 3 is placed beside the cavity 2 with a space of about 1 mm provided between them.

Consequently, the pressure sensor is to be provided apart by a space of about 2 mm from the outermost end of the fluid pumping section 1, and therefore a dead zone of about 2 mm from the outermost end of the fluid pumping section 1 takes place. Therefore, when the tube is erroneously placed in a portion apart by about 2 mm from the fluid pumping section 1, it is possible that the erroneous placement of the tube may be not detected.

(B) Downstream/upstream occlusion detection

As described in regard to the items (2) and (3), it is required to provide a special pressure sensor on the downstream side or the upstream side of the fluid pumping section, or at the portion of separation of the fluid pumping section. The above-mentioned arrangement is an obstacle in compacting the fluid infusion pump.

(C) Motor rotational position detection

When the encoder as described in regard to the item (4) is employed, the encoder requires a great amount of volume, which is an obstacle in compacting and reducing the cost of the fluid infusion pump.

Furthermore, when the aforementioned encoder or a pulse motor is employed, the position in which the motor stops is not identified when the power is turned on for the reason that the rotational position is detected from the reference position of one turn of the shaft obtained from the photosensor. Therefore, it is not found which finger is pressing the tube when the power is turned on, and in the worst case, the rotational position cannot be detected until the shaft makes one rotation.

The above-mentioned fact causes a serious problem when the medication fluid is transferred at a low flow rate of 0.1 ml/hr or in a similar case. In detail, a medication fluid to be infused at such a low flow rate of 0.1 ml/hr requires a flow control with high accuracy in most cases. Therefore, the rotating speed of the motor is increased in the period of the dead band to eliminate the period in which no fluid is transferred to thereby allow the fluid to be consistently transferred. However, when the flow rate is 0.1 ml/hr, it takes about one hour to detect the reference position through one rotation of the motor from the time when the power is turned on. Therefore, immediately after the power is turned on, it is possible that a condition in which no medication fluid is transferred may take place.

Furthermore, at a low flow rate of 0.1 ml/hr or in a similar case, there is observed a local change of flow rate as in portions indicated by the arrows in FIG. 27 even when the flow rate is set at a constant value by means of the structure of the fingers and setting of a tube pressing timing of the fingers in the fluid pumping section. It is to be noted that an interval (A) is the dead band when the motor is started.

(D) Driving torque control (control of current applied to the motor)

When controlling the driving torque in the required phase based on the phase with respect to the reference point detected in the item (4), the current cannot be controlled until the motor makes one turn from the time when the power is turned on and detects the reference position (about one hour when the flow rate is 0.1 ml/hr) in the same manner as in the motor rotational position detection. Therefore, it is required to flow a great quantity of current in the above-mentioned time. Consequently, a great current consumption results to require a power battery to have a great capacity, which is an obstacle in compacting the fluid infusion pump.

Furthermore, when controlling the current applied to the motor by means of the encoder as described in regard to the item (5), it is possible that the fluid transfer may be stopped until the slit passage time is counted by supplying pulses more in amount than the amount of pulses to be supplied to the motor in a time in which one slit passes. Therefore, it is possible that a fluid transfer speed required in the case where the fluid is transferred at a low flow rate cannot be controlled with high accuracy.

SUMMARY OF THE INVENTION

The object of the present invention is therefore to provide a fluid infusion pump which can detect the erroneous tube placement and is free of the dead zone, a fluid infusion pump which can detect the downstream occlusion and upstream occlusion as well as the rotational position of the motor and is able to be miniaturized, a fluid infusion pump which can immediately detect the dead band when the power is turned on and control the flow rate with high accuracy, or a fluid infusion pump which achieves a reduced current consumption when the power is turned on or in a steady-state operation.

In order to achieve the aforementioned object, the present invention provides a fluid infusion pump in which a tube is placed on a wall of a main body of the fluid infusion pump to be covered with a cover, and the tube is peristaltically pressed forwardly or reversely in a lengthwise direction to be occluded by fore end portions of a plurality of fingers which advance and retreat in a cavity formed in the wall with the cover closed, thereby transferring a medication fluid inside the tube in the lengthwise direction, the fluid infusion pump comprising:

pressure detecting means for detecting a pressure force exerted from each of the fingers via the tube and outputting a detection signal while being placed in a position of the cover opposite to the fingers in the wall of the main body within a range of area in which the fore end portions of the fingers can press the tube.

According to the present invention as described above, in a condition in which the tube is placed along the wall surface of the main body and the cover closed, the tube is peristaltically pressed by the fore end portions of the fingers to transfer the medication fluid inside the tube.

In the above case, a pressure force exerted from each of the fingers via the tube is detected by the pressure detecting means placed in a position of the cover opposite to the fingers provided in the wall of the main body within the range of area in which the fore end portion of each of the fingers can press the tube to thereby output a detection signal.

Also, the present invention provides a fluid infusion pump in which a tube is placed on a wall of a main body of the fluid infusion pump to be covered with a cover, and the tube is peristaltically pressed forwardly or reversely in a lengthwise direction to be occluded by fore end portions of a plurality of fingers which advance and retreat in a cavity formed in the wall with the cover closed, thereby transferring a medication fluid inside the tube in the lengthwise direction, the fluid infusion pump comprising:

a pressure plate which is placed in a position of the cover opposite to the fingers in the wall of the main body within a range of area in which the fore end portions of the fingers can press the tube, and is urged by a spring toward the fingers against a pressure force exerted from each of the fingers via the tube; and pressure detecting means for detecting the pressure force exerted from each of the fingers via the tube, the pressure plate, and the spring and outputting a detection signal while being connected to an end of the spring on a side opposite from the pressure plate.

According to the present invention as described above, when the medication fluid in the tube is transferred, the pressure plate placed in a position of the cover opposite to the fingers in the wall of the main body within a range of area in which the fore end portions of the fingers can press the tube is pressed by the fingers via the tube against an urge force of the spring.

Then, by the pressure detecting means connected to the end of the spring on the side opposite from the pressure plate, the pressure force exerted from each of the fingers is detected via the tube, the pressure plate, and the spring to thereby output a detection signal.

In an embodiment, the pressure detecting means comprises: a pressure sensing plate which is distorted by a compression force exerted from the spring while being mounted to the end of the spring on the side opposite from the pressure plate; and a load cell for detecting a distortion of the pressure sensing plate.

According to the embodiment, when the medication fluid in the tube is transferred and the pressure plate is pressed against the urge force of the spring, the pressure sensing plate connected to the end of the spring on the side opposite from the pressure plate is distorted in response to the compression force of the spring.

Then the distortion force of the pressure sensing plate is detected by the load cell to output the detection signal corresponding to the pressure force exerted from each of the fingers.

In an embodiment, there is further provided a slit disk which has slits having different lengths in a direction of rotation arranged not at an identical interval in a circle, and is mounted to a shaft of a motor for driving the fingers via cams;

a photosensor which detects light travelling through any of the slits of the slit disk and outputs a detection signal; and rotational position detecting means for specifying one of the slits located in a position of the photosensor by a specified method based on a detection signal outputted from the photosensor and detecting a rotational position of the motor.

According to the embodiment, when the medication fluid in the tube is transferred, light travelling through the slits which have different lengths in the direction of rotation and are arranged not at an identical interval in a circle in the slit disk mounted to the shaft of the motor for driving the fingers via the cams is detected by the photosensor to thereby output a detection signal.

Then the slit located in the position of the photosensor is specified according to a specified method based on the detection signal from the photosensor by the rotational position detecting means to thereby detect the rotational position of the motor.

In an embodiment, there is further provided time counting means for counting a time interval between a time when the detection signal from the photosensor is inverted in level and a time when the detection signal is subsequently inverted in level, wherein the rotational position detecting means comprises slit specifying means for detecting the length of the slit or the interval of the slits passing through the position of the photosensor based on a time interval counted by the time counting means, and specifying the slit located in the position of the photosensor based on a value of the detected length or interval.

According to the embodiment, when the medication fluid in the tube is transferred, the time interval between the time when the detection signal from the photosensor is inverted in level and the time when the detection signal is subsequently inverted in level is counted by the time counting means.

Then the length of the slit or the interval of the slits passing through the position of the photosensor is detected by the slit specifying means of the rotational position detecting means based on the time counted by the time counting means, and according to the value of the detected length or interval, the slit located in the position of the photosensor is specified. Then based on the specified slit, the rotational position of the motor is detected.

In an embodiment, the motor is a stepping motor, a counter which counts an amount of drive pulses supplied to the stepping motor in a time interval between a time when the detection signal from the photosensor is inverted in level and a time when the detection signal is subsequently inverted in level is further comprised, and the rotational position detecting means comprises slit specifying means for detecting the length of the slit or the interval of the slits passing through the position of the photosensor based on an amount of pulses counted by the counter, and specifying the slit located in the position of the photosensor based on a value of the detected length or interval.

According to the embodiment, the medication fluid in the tube is transferred. In the above stage, the amount of drive pulses supplied to the stepping motor for driving the fingers via the cams is counted in the time interval between the time when the detection signal from the photosensor is inverted in level and the time when the detection signal is subsequently inverted in level.

Then, the length of the slit or the interval of the slits passing through the position of the photosensor is detected by the slit specifying means of the rotational position detecting means based on the amount of pulses counted by the counter. Then the slit located in the position of the photosensor is specified according to the detected length or interval to thereby detect the rotational position of the motor.

In an embodiment, there is further provided erroneous placement deciding means for observing a change of pressure force exerted from each of the fingers by taking in the detection signal from the pressure detecting means, and when at least one of a peak and a bottom of the pressure force is not greater than a specified level, deciding that the tube is not correctly placed in the position where the tube is to be pressed by the fingers.

According to the embodiment, when the medication fluid in the tube is transferred, the placement of the tube is observed based on the detection signal from the pressure detecting means arranged in the range of area in which the fore end portions of the fingers can press the tube. When at least one of the peak and the bottom of the pressure force exerted from each of the fingers is not greater than a specified level, the erroneous placement deciding means decides that the tube is not correctly placed in the position where the tube is to be pressed by the fingers.

Thus the erroneous placement of the tube is decided with high accuracy based on the detection signal from the pressure detecting means arranged without any dead zone.

In an embodiment, the erroneous placement deciding means takes in the detection signal from the pressure detecting means in a cycle shorter than a cycle in which the fingers press the tube.

According to the embodiment, when the medication fluid in the tube is transferred, the detection signal from the pressure detecting means is taken in by the erroneous placement deciding means in a cycle shorter than the cycle in which the fingers press the tube.

Thus the peak and bottom pressure values of the pressure force exerted from each of the fingers are securely taken in to decide whether the tube is erroneously placed.

In an embodiment, there is further provided a slit disk which has slits having different lengths in a direction of rotation arranged not at an identical interval in a circle, and is mounted to a shaft of a motor for driving the fingers via cams;

a photosensor which detects light travelling through any of the slits of the slit disk and outputs a detection signal; and rotational position detecting means for specifying one of the slits located in a position of the photosensor by a specified method based on a detection signal outputted from the photosensor and detecting a rotational position of the motor, and wherein the erroneous placement deciding means takes in the detection signal from the pressure detecting means in synchronization with an inversion in level of the detection signal from the photosensor.

According to the embodiment, when the medication fluid in the tube is transferred, the detection signal from the pressure detecting means is taken in by the erroneous placement deciding means in synchronization with the inversion in level of the detection signal from the photosensor.

Thus the peak and bottom pressure values of the pressure force exerted from each of the fingers are securely taken in in synchronized with the inversion in level of the detection signal from the photosensor to decide whether the tube is erroneously placed.

In an embodiment, there is further provided downstream occlusion deciding means for observing the pressure force exerted from each of the fingers by taking in the detection signal from the pressure detecting means, and when the pressure force increases in level to reach a specified level, deciding that downstream occlusion occurs.

According to the embodiment, when the medication fluid in the tube is transferred, the level of the pressure force exerted from each of the fingers based on the detection signal from the pressure detecting means is observed by the downstream occlusion deciding means. When the level of the pressure force increases to reach a level not smaller than a specified level, it is decided that the downstream occlusion occurs.

Thus the downstream occlusion is detected based on the detection signal from the pressure detecting means usable in detecting the erroneous placement of the tube.

In an embodiment, there is further provided upstream occlusion deciding means for observing a change of the pressure force exerted from each of the fingers by taking in the detection signal from the pressure detecting means, and when a bottom level in the change of the pressure force reduces by a value not smaller than a specified value, deciding that upstream occlusion occurs.

According to the embodiment, when the medication fluid in the tube is transferred, the change of the pressure force exerted from each of the fingers is observed based on the detection signal from the pressure detecting means by the upstream occlusion deciding means. When the bottom level in the change of the pressure force reduces by not less than a specified value, it is decided that the upstream occlusion occurs.

Thus the upstream occlusion is detected based on the detection signal from the pressure detecting means usable in detecting the erroneous placement of the tube.

In an embodiment, the motor is a stepping motor, and there is further provided time counting means for counting an elapsed time from a time when one pulse of drive pulses is supplied to the stepping motor;

time setting means for setting a pulse output interval time by a specified method according to the rotational position of the stepping motor detected by the rotational position detecting means; and motor driving means for driving the stepping motor by supplying one pulse of the drive pulses to the stepping motor when the elapsed time counted by the time counting means reaches the pulse output interval time.

According to the embodiment, when the medication fluid in the tube is transferred, the elapsed time from the time when the drive pulse is supplied by one pulse to the stepping motor is counted by the time counting means. Meanwhile, a pulse output interval time is set by the time setting means by a specified method according to the rotational position of the stepping motor detected by the rotational position detecting means.

When the elapsed time counted by the time counting means reaches the pulse output interval time, the drive pulse is supplied by one pulse to the stepping motor to thereby drive the stepping motor.

Thus the stepping motor is driven at a speed according to the rotational position thereof.

In an embodiment, the motor is a stepping motor, and the fluid infusion pump further comprises:

duty ratio setting means for seeing a duty ratio of drive pulses to be supplied to the stepping motor by a specified method according to the rotational position of the stepping motor detected by the rotational position detecting means; and duty ratio controlling means for controlling the duty ratio of the drive pulses so that the duty ratio set by the duty ratio setting means is achieved, whereby a motor driving torque is controlled by controlling a current applied to the stepping motor.

According to the embodiment, when the medication fluid in the tube is transferred, the duty ratio of the drive pulses supplied to the stepping motor is set by the duty ratio setting means by a specified method according to the rotational position of the stepping motor detected by the rotational position detecting means. Then the duty ratio of the drive pulses is controlled by the duty ratio controlling means so that the duty ratio set by the duty ratio setting means is achieved.

Thus the current applied to the stepping motor is controlled according to the rotational position of the stepping motor to thereby control the motor driving torque.

In an embodiment, the motor is a stepping motor, and the fluid infusion pump further comprises:

motor initial driving means for driving the stepping motor until an edge of a next slit of the slit disk reaches a position in the vicinity of the photosensor by supplying a specified amount of pulses having a duty ratio set by a specified method to the stepping motor according to the rotational position of the stepping motor detected by the rotational position detecting means;

duty ratio setting means for setting the duty ratio of the drive pulses to be supplied to the stepping motor located in a rotational position such that the edge of the next slit of the slit disk reaches a position in the vicinity of the photosensor at a stationary duty ratio at which a minimum current assuring a stationary torque is achieved by a specified method according to the rotational position of the stepping motor, and thereafter setting the duty ratio of the drive pulses at a duty ratio at which a necessary minimum drive current in a present rotational position is achieved by successively supplying to the stepping motor the drive pulses having a duty ratio obtained by gradually increasing the set stationary duty ratio until the detection signal from the photosensor is inverted in level; and motor driving means for driving the stepping motor until an edge of a next slit but one of the slit disk reaches a position in the vicinity of the photosensor by supplying to the stepping motor the drive pulses having a drive duty ratio set according to a specified procedure based on the duty ratio set by the duty ratio setting means.

According to the embodiment, when the medication fluid in the tube is transferred, the duty ratio of the drive pulses is set by the motor initial driving means according to the rotational position to thereby drive the stepping motor until the edge of the next slit of the slit disk reaches the position in the vicinity of the photosensor. Then the stationary duty ratio set by a specified method is gradually increased by the duty ratio setting means until the detection signal from the photosensor is inverted in level. Thus the duty ratio of the drive pulses is set at the duty ratio at which the necessary minimum drive current in the present rotational position is achieved.

Then the drive pulse having a drive duty ratio based on the duty ratio set by the duty ratio setting means is supplied to the stepping motor by the motor driving means to thereby drive the stepping motor until the edge of the next slit but one of the slit disk reaches the position in the vicinity of the photosensor.

Subsequently, the operations of the duty ratio setting means and the motor driving means are repeated to set the duty ratio of the drive pulses every time the slit edge is detected in a manner that the necessary minimum drive current in the present rotational position is achieved, with which the stepping motor is driven at the necessary minimum drive current.

In an embodiment, the motor is a stepping motor, and there is further provided reversing start duty ratio setting means for setting a stationary duty ratio by a specified method according to the rotational position of the stepping motor detected by the rotational position detecting means, and setting the duty ratio of the drive pulses at a reversing start duty ratio at which a drive current for making the stepping motor start to reverse in a present rotational position is achieved by successively supplying to the stepping motor drive pulses having a duty ratio obtained by gradually reducing the set stationary duty ratio until the detection signal from the photosensor is inverted in level;

duty ratio setting means for setting the duty ratio of the drive pulses at a duty ratio at which a minimum drive current necessary in a time when the stepping motor starts to be driven is achieved by successively supplying to the stepping motor drive pulses having a duty ratio obtained by gradually increasing the reversing start duty ratio set by the reversing start duty ratio setting means until the detection signal from the photosensor is inverted in level; and motor driving means for making the stepping motor start to be driven by supplying to the stepping motor the drive pulses having the drive duty ratio set according to a specified procedure based on the duty ratio set by the duty ratio setting means.

According to the embodiment, the stationary duty ratio set according to the rotational position is gradually reduced by the reversing start duty ratio setting means until the detection signal from the photosensor is inverted in level. Thus the duty ratio of the drive pulses is set at the reversing start duty ratio at which the drive current for making the stepping motor start to rotate reversely in the present rotational position is achieved.

Then the reversing start duty ratio is gradually increased by the duty ratio setting means until the detection signal from the photosensor is inverted in level to be set at the duty ratio at which the minimum drive current necessary in the time when the stepping motor starts to be driven is achieved.

Then the drive pulse having a drive duty ratio based on the duty ratio set by the duty ratio setting means is supplied to the stepping motor by the motor driving means to thereby drive the stepping motor.

Thus the duty ratio of the drive pulses is set so that the minimum drive current necessary in the time when the stepping motor starts to be driven is achieved, with which the stepping motor starts to be driven at a small current.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 9 is a flowchart of a motor rotational position detecting operation of the fluid infusion pump;

FIG. 11 is a flowchart of an erroneous tube placement detecting operation of the fluid infusion pump;

FIG. 25 is a flowchart of an upstream occlusion detecting operation of the fluid infusion pump;

DETAILED DESCRIPTION OF THE PREFERRED EMBODIMENTS

The present invention will now be described in detail based on several embodiments thereof with reference to the accompanying drawings.

The following embodiments are related to a fluid infusion pump having an encoder for detecting the rotational position of a motor.

First embodiment

Figure 1:
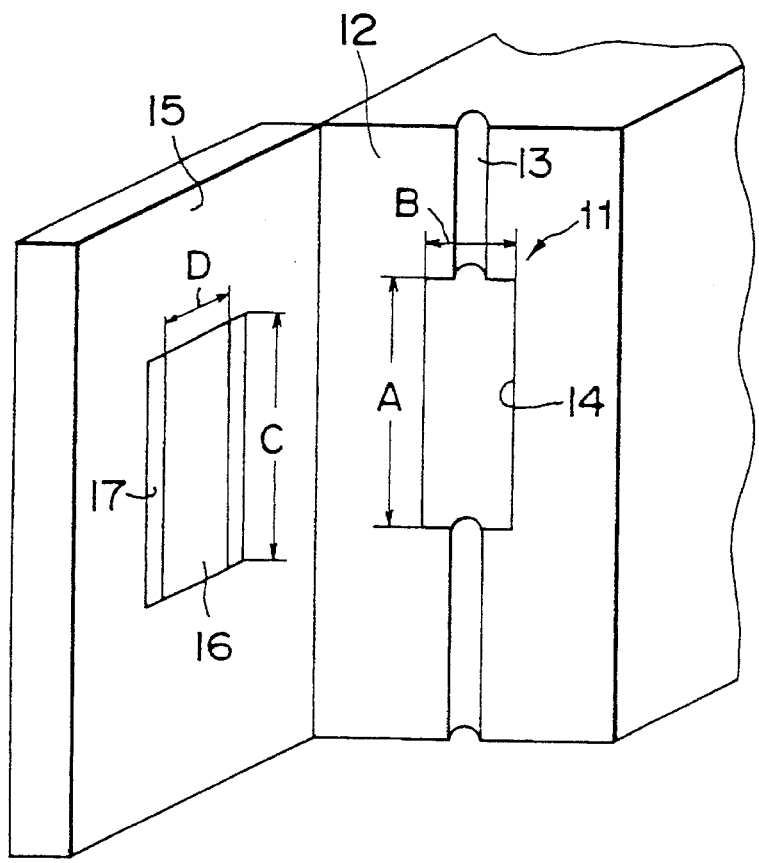
FIG. 1 is an external view of a portion in the vicinity of a fluid pumping section of a fluid infusion pump of the present invention.
Figure 26:
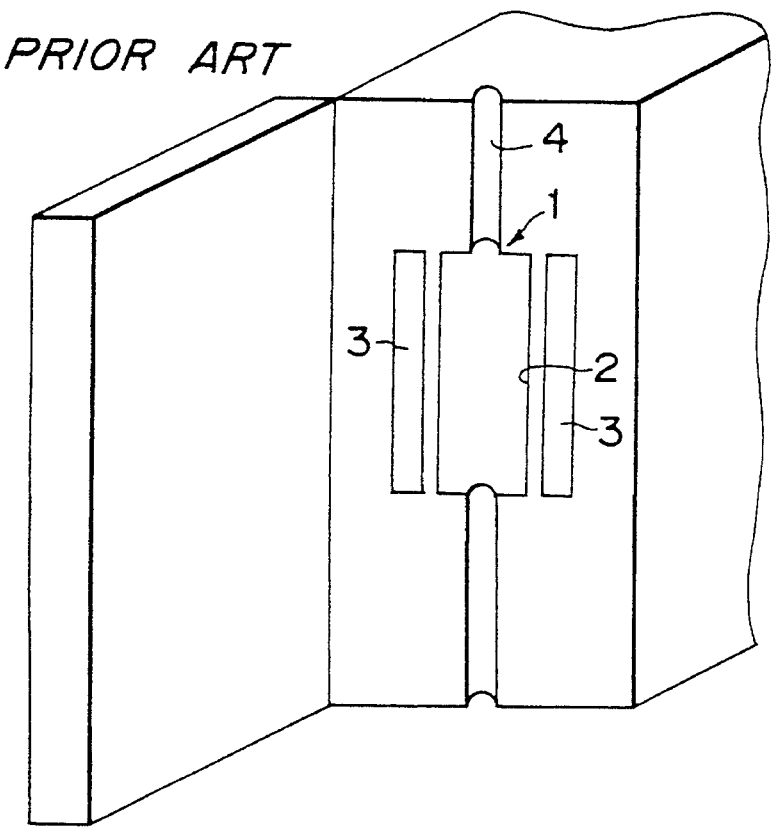
FIG. 26 is an explanatory view of an erroneous tube placement detection of a conventional fluid infusion pump.

FIG. 1 shows an external view of a portion in the vicinity of a fluid pumping section of a fluid infusion pump of the present embodiment.

A fluid pumping section 11 of the fluid infusion pump of the present embodiment is a linear peristaltic system. The fluid pumping section 11 is comprised of a groove 13 which is formed in a wall 12 of a main body and receives a tube, a plurality of fingers in a stack which peristaltically occlude the tube placed in the groove 13, cams for driving the fingers, and a shaft around which the cams are mounted. The fingers peristaltically occlude the tube placed in the groove 13 by advancing toward and retreating from a cover 15 while shifting in phase between each adjacent ones in a cavity 14 formed in a middle portion of the groove 13.

Since the fingers, the cams, and the shaft are assembled in the cavity 14, they are not shown in FIG. 1.

In a position of an inner wall of the cover 15 for covering the fluid pumping section 11 wherein the position is opposite to the fluid pumping section 11, there is buried a pressure plate 17. To a surface of the pressure plate 17 is attached a pressure sensor 16 in a sheet form, and is urged toward the fingers by a spring (not shown in FIG. 1) from inside.

Figure 2A:
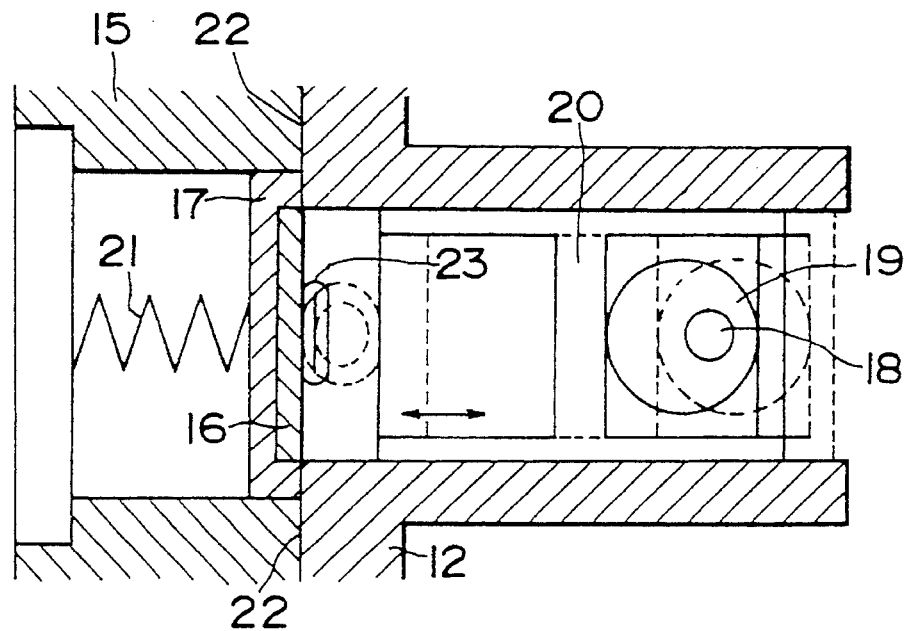
FIGS. 2A and 2B are sectional views of an exemplified fluid pumping section.
Figure 2B:
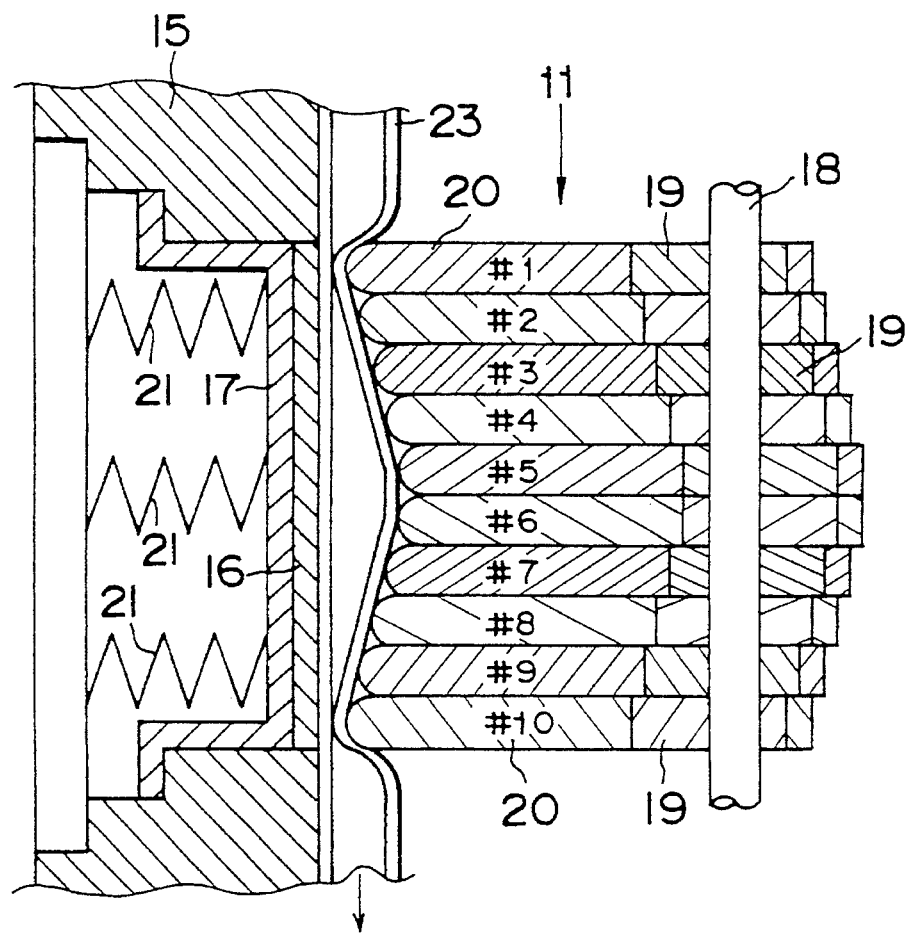

FIGS. 2A and 2B are sectional views of the fluid pumping section 11 in a condition in which the cover 15 is closed. It is to be noted that FIG. 2A is a transverse sectional view, while FIG. 2B is a longitudinal sectional view. The following describes an operation of the fluid pumping section 11 with reference to FIGS. 2A and 2B.

When the shaft 18 is made to rotate by a motor (not shown), ten cams 19 mounted in a stack around the shaft 18 to sequentially shift in phase as offset by 2 mm with respect to the shaft 18 rotate. Then the fingers 20 in which the cams 19 are rotatably inserted reciprocate within a length of 4 mm in a direction perpendicular to the surface of the pressure plate 17. In the above case, the pressure plate 17 is pressed against a reference surface 22 by a strong urge force exerted from the spring 21. Therefore, when each cam 19 reaches a top dead center, the corresponding finger 20 occludes the tube 23 (indicated by solid lines in FIG. 2A). When each cam 19 reaches a bottom dead center, the corresponding finger 20 releases the tube 23 at maximum (indicated by dashed lines in FIG. 2A).

Thus by mounting the ten cams 19 around the shaft 18 while shifting in angle the cams 19 by 36 degrees between adjacent ones, and making each of the cams 19 correspond to a respective of the fingers 20, the fingers 20 occlude the tube 23 sequentially from a #1 finger (expressed as "$20_1$", and so forth) to a #10 finger $20_{10}$ according as the shaft 18 makes one turn to thereby discharge the medication fluid in the tube 23.

When the medication fluid is discharged, a pressure applied to the tube 23 from each of the fore ends portions of the #1 finger 201 through the #10 finger, $20_{10}$ is detected by the pressure sensor 16 attached to the surface of the pressure plate 17. Then, according to a detected change of pressure, there can be detected the rotational position of the cams 19 (i.e., the rotational position of the motor), a possible erroneous placement of the tube 23 in the groove 13, and the like.

Figure 3A:
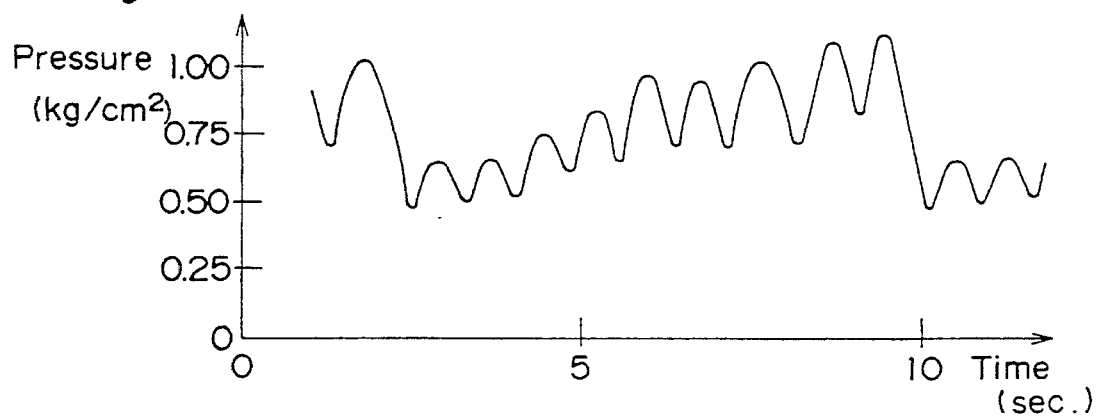
FIGS. 3A, 3B, and 3C are graphs showing an exemplified change of pressure detected by a pressure sensor shown in FIGS. 2A and 2B.
Figure 3B:
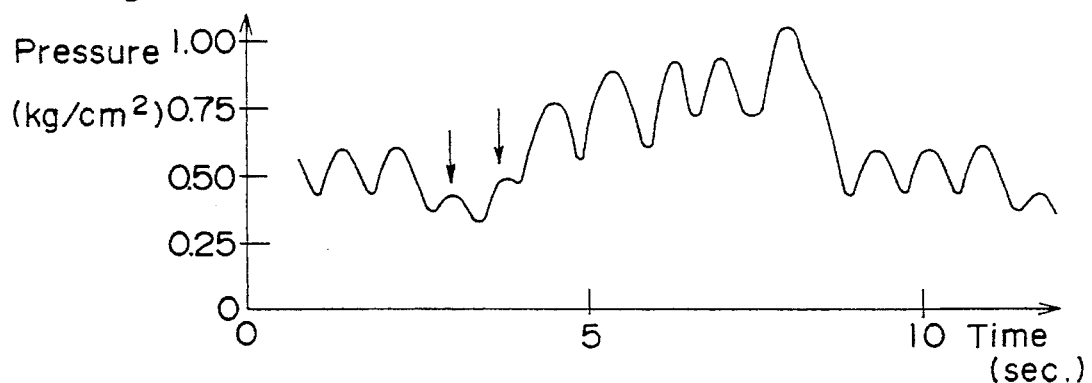
Figure 3C:
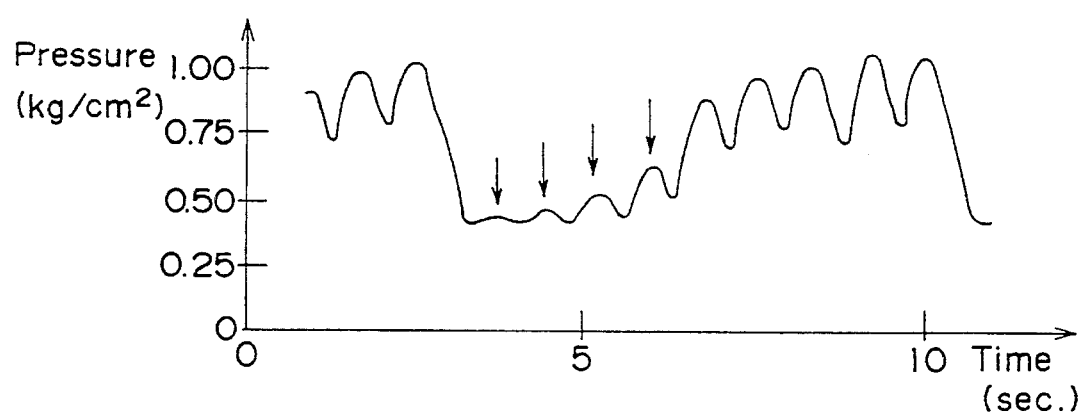

FIGS. 3A, 3B, and 3C show examples of the change of pressure detected by the pressure sensor 16. FIG. 3A shows a change of pressure in a case where the tube is normally placed. According to the application of a pressure from each finger 20, nine peaks appear (the #1 finger $20_1$ and the #10 finger $20_{10}$ located at both ends simultaneously press the tube 23). As a whole, the pressure increases sequentially from the pressure corresponding to the #2 finger $20_2$ to the pressure corresponding to the #10 finger $20_{10}$. In contrast to the above, in FIG. 3B, peaks of the pressures corresponding to the #4 finger $20_4$ and the #5 finger $20_5$ do not appear in positions pointed by the arrows, which indicates the fact that the tube is erroneously placed in a middle portion of the fluid pumping section 11. In FIG. 3C, peaks of pressures corresponding to the #2 finger $20_2$ through the #5 finger $20_5$ do not appear in positions pointed by the arrows, which indicates the fact that the tube is erroneously placed in an upper portion off the fluid pumping section 11.

Therefore, by making a length A and a width B of the fluid pumping section 11 shown in FIG. 1 have with a length C and a width D of the pressure sensor 16 the following relationships:

$$A=C, B=D,$$

an area of the pressure sensor 16 abutting against the tube 23 is reduced when the tube 23 is displaced even a little bit from the territory of the fluid pumping section 11. Therefore, an output level of the pressure sensor 16 is reduced which allows the erroneous placement of the tube to be detected. With the above-mentioned arrangement, no dead zone in which the displacement of the tube cannot be detected takes place.

Figure 4:
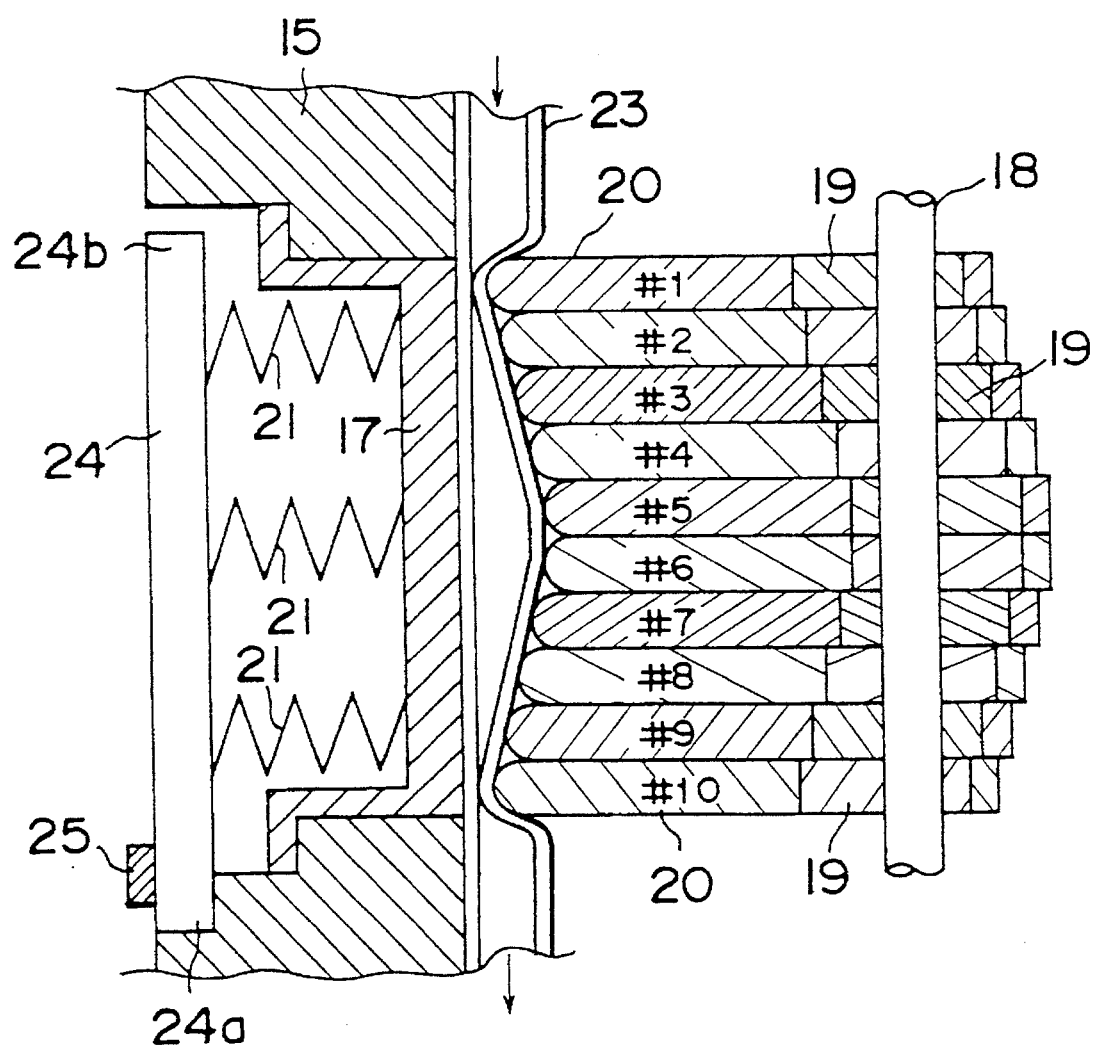
FIG. 4 is a sectional view of a fluid pumping section different from the one shown in FIGS. 2A and 2B.

FIG. 4 is a sectional view of a structure in the vicinity of the fluid pumping section employing a load cell 25 as a pressure detecting means for detecting the pressure applied to the tube 23 from the #1 finger $20_1$ through the #10 finger $20_{10}$.

In the present structure, the surface of the pressure plate 17 is exposed to the fingers 20 to be able to directly support the tube 23. Meanwhile, an outer end of the spring 21 which urges the pressure plate 17 toward the fingers 20 is connected to a pressure sensing plate 24 which has its lower end 24a fixed to the cover 15 and has its upper end 24b made to serve as a free end. Another surface of the pressure sensing plate 24 is mounted with the load cell 25 for detecting a distortion force of the pressure sensing plate 24.

In the above-mentioned structure, when the pressure plate 17 is pressed by each of the fingers 20, the pressure plate 17 moves to compress the spring 21. Then the pressure sensing plate 24 is distorted by an elasticity force of the spring 21, and the distortion in the time is detected by the load cell 25.

By making the length and width of the fluid pumping section 11 equal to the length and width of the exposed portion of the pressure plate 17, no dead zone in which the displacement of the tube cannot be detected takes place.

In the structure of each fluid pumping section, the spring 21 is provided on the side of the cover 15. However, it is acceptable to constitute each finger 20 by a first finger part (not shown) following the cam 19 and a second finger part (not shown) for pressing the tube 23, and interpose a spring (not shown) between the first finger part and the second finger part. In the above-mentioned case, a pressure plate can be formed integrally with the cover 15 or composed of the inner wall itself of the cover 15. When the above-mentioned arrangement is adopted, it is preferred to attach a pressure sensor having the same dimensions as those of the fluid pumping section in an area opposite to the fluid pumping section onto the pressure plate formed integrally with the cover 15 or the inner wall of the cover 15.

In regard to a pressure detecting means usable in the present invention, it is acceptable to use a conductive rubber in a sheet form, a pressure sensor of which capacitance varies in compliance with a pressure, or the like other than the pressure sensor 16 in a sheet form and the load cell 25 of which resistance varies in compliance with a pressure. Otherwise, it is also permitted to use another pressure detecting means according to the progress of technology.

Then the following describes a control system of the fluid infusion pump having the aforementioned structure in the vicinity of the fluid pumping section. It is herein assumed that the aforementioned fluid pumping section and the pressure detecting means are the fluid pumping section 11 and the pressure sensor 16 shown in FIGS. 2A and 2B. In the above-mentioned case, the fluid pumping section or the pressure detecting means is not always required to be the fluid pumping section 11 or the pressure sensor 16 shown in FIGS. 2A and 2B.

Figure 5:
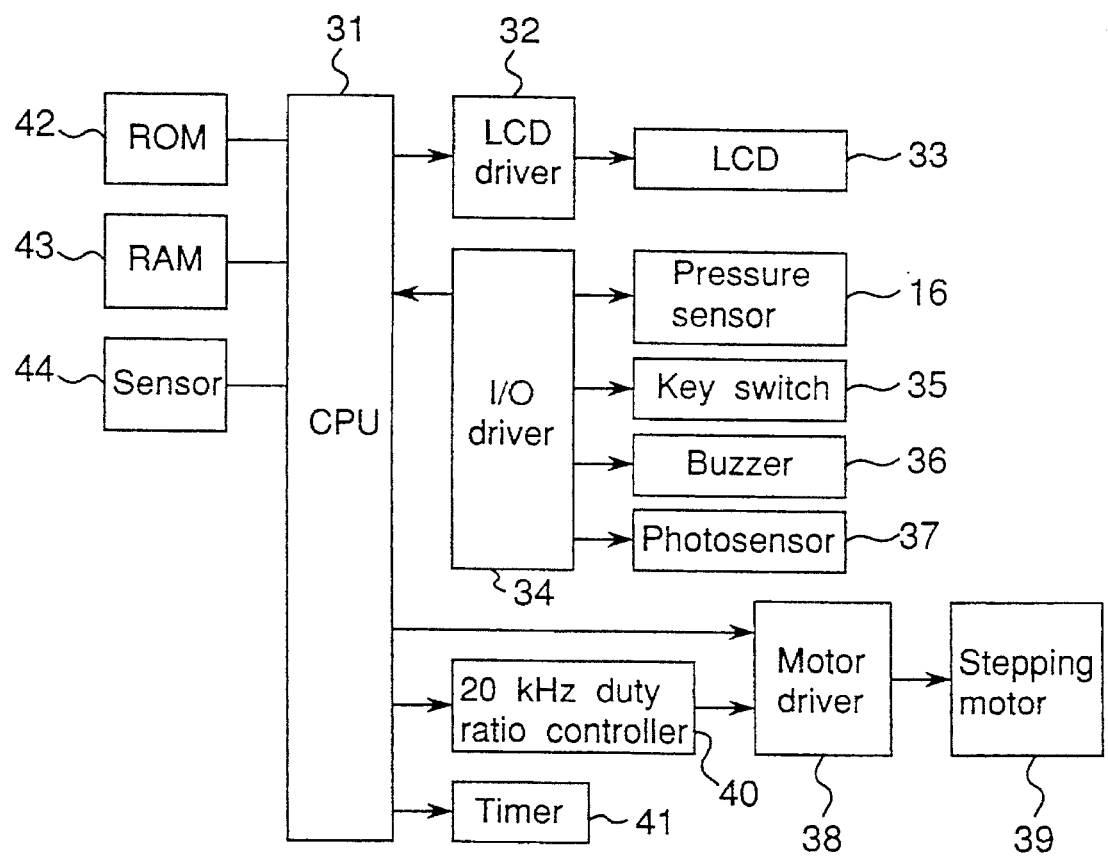
FIG. 5 is a block diagram of a control system of the fluid infusion pump having the fluid pumping section shown in FIGS. 2A and 2B or in FIG. 4.

FIG. 5 is a block diagram of the control system of the present fluid infusion pump.

On an LCD (liquid crystal display) 33 driven by an LCD driver 32 are displayed the flow rate of the fluid and the like.

The pressure sensor 16 detects a pressure force exerted from each of the fingers 20 for pressing the tube 23. A key switch 35 is comprised of keys and switches for the setting of fluid transfer start, fluid transfer stop, flow rate, and the like. A buzzer 36 issues an alarm sound when an alarm takes place. A photosensor 37 is a sensor for detecting an edge of a slit of the slit disk in an encoder described in detail hereinafter. An I/O driver 34 is a drive circuit for peripheral circuits including an amplifier, an analog-to-digital converter, and the like for processing waveforms from each sensor, and the like.

Figure 6A:
FIGS. 6A, 6B, 6C, and 6D are explanatory views of a motor drive pulse signal supplied to a stepping motor as shown in FIG. 5.
Figure 6B:
Figure 6C:
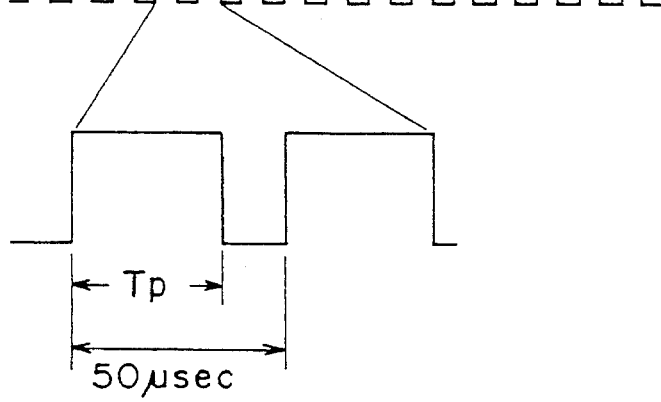
Figure 6D:
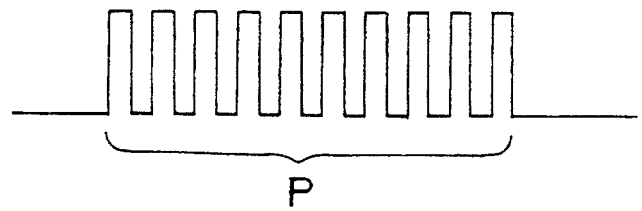

A stepping motor 39 rotates the shaft 18 to drive the fingers 20 to perform the fluid transfer. A 20 kHz duty ratio control section 40 controls the duty ratio of a pulse signal having a frequency of 20 kHz, and outputs a 20 kHz duty ratio changing pulse signal. A motor driver takes a logical product of a normal motor drive pulse signal and the 20 kHz duty ratio changing pulse signal outputted from the 20 kHz duty ratio control section 40 to generate a motor drive pulse signal, and supplies the obtained signal to the stepping motor In the above case, the 20 kHz duty ratio changing pulse signal has a pulse waveform having a cycle of 50 μsec as shown in FIGS. 6B and 6C, and a pulse width Tp is changed by the 20 kHz duty ratio control section 40 to control the duty ratio of the signal. Therefore, the motor drive pulse signal which is the logical product of the normal motor drive pulse signal shown in FIG. 6A and the 20 kHz duty ratio changing pulse signal shown in FIG. 6B contains pulses P which has the same cycle as that of the normal motor drive pulse signal and a duty ratio controlled by the 20 kHz duty ratio control section 40 as shown in FIG. 6D.

Thus the quantity of current supplied to the stepping motor 39 is controlled to control the driving torque of the stepping motor 39.

A timer 41 counts a time in executing a variety of control operations. Sensors 44 include a sensor for air detection and the like other than the pressure sensor 16 and the photosensor 37.

A RAM (random access memory) 43 stores data such as pressure data taken in from a variety of tables and sensors. A CPU (central processing unit) 31 controls the LCD driver 32, I/O driver 34, motor driver 38, 20 kHz duty ratio control section 40, timer 41, sensors 44, and RAM 43 according to a program stored in a ROM (read only memory) 42 to execute the processes of fluid transfer control, fluid transfer speed correction, output waveform processing of the pressure sensor 16, and the like.

Figure 7:
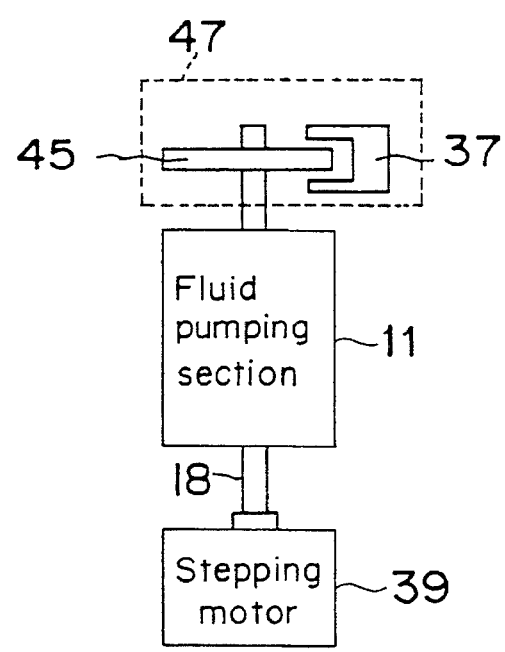
FIG. 7 is an explanatory view of an encoder mounted in the fluid infusion pump.

As shown in FIG. 7, the shaft 18 of the fluid infusion pump of the present embodiment has its upper end portion mounted with a slit disk 45 having a plurality of slits along the periphery of the slit disk. An encoder 47 is comprised of the slit disk 45 and the photosensor 37. A lower end portion of the shaft is mounted with the stepping motor 39 shown in FIG. 5. The stepping motor 39 makes one turn in 400 pulses of the supplied motor drive pulse signal. When the stepping motor 39 makes one turn, the fluid pumping section 11 transfers a medication fluid by 0.1 ml.

Figure 8:
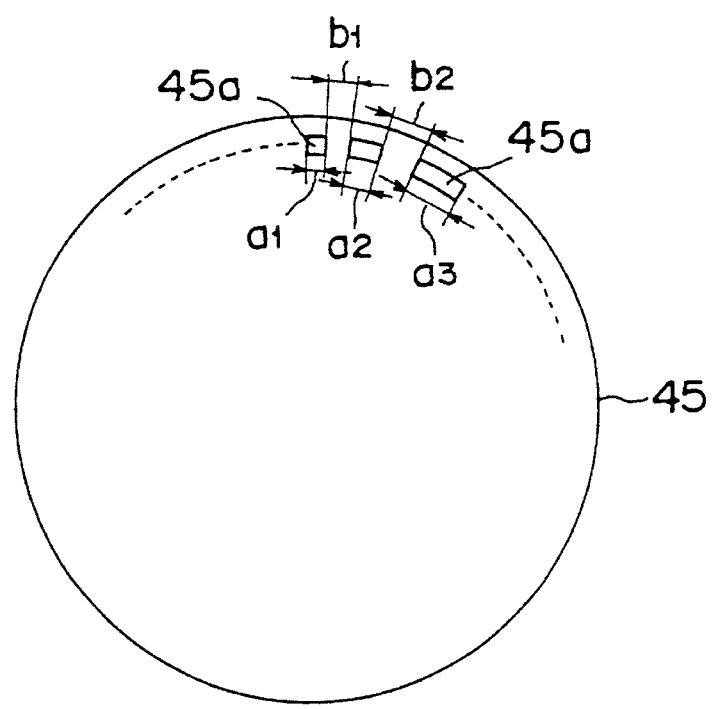
FIG. 8 is a plan view of a slit disk as shown in FIG. 7.

As shown in FIG. 8, slits 45a provided at the slit disk 45 have different dimensions in regard to their circumferential length $a_i$ and circumferential interval $b_i$ (i=1, 2, ..., 19), where a combination ($a_i$, $b_i$) of the slit length $a_i$ and the slit interval $b_i$ has an arrangement as described hereinbelow. It is to be noted that each numeral representing the width or the interval is the amount of pulses of the motor drive pulse signal.

The aforementioned combination ($a_i$, $b_i$) is as follows.

($a_i$, $b_i$): (3, 19)→(4, 18)→(5, 17)→(6, 16)→
(7, 15)→(8, 14)→(9, 13)→(10, 12)→
(11, 11)→(12, 10)→(13, 9)→(14, 8)→
(15, 7)→(16, 6)→(17, 5)→(18, 4)→
(19, 3)→(21, 1)→(2, 2)

In order to measure the slit length $a_i$ and the slit interval $b_i$ in terms of time, assuming that a set flow rate is Y ml/hr and the amount of pulses corresponding to the slit length $a_i$ or the amount of pulses corresponding to the slit interval $b_i$ is $Z_i$, the time can be expressed as follows.

$$3600/(10Y \times 400) \times Z_i (sec)$$

The fluid infusion pump having the above-mentioned construction operates in a manner as follows to detect the rotational position of the motor as a reference in executing a variety of control operations.

FIG. 9 is a flowchart of a rotational position detecting operation executed under the control of the CPU 31. The following describes in detail the rotational position detecting operation with reference to FIG. 9.

In step S1, it is decided whether or not a start switch is turned on. When the start switch is turned on, the program flow proceeds to seep S2.

In step S2, a pulse output interval time of the motor drive pulse signal supplied to the stepping motor 39 is set by the motor driver 38 according to a set flow rate.

Then, the contents of a count value CT and an edge number PT stored in the RAM 43 are initialized to "0".

In step S3, it is decided whether or not an elapsed time (referred to as an "output time" hereinafter) from a time when one pulse of the pulses P (refer to FIG. 6D) of the motor drive pulse signal is supplied to the stepping motor 39 exceeds a specified time (pulse output interval time). Consequently, when the output time is exceeding the pulse output interval time, the program flow proceeds to step S4.

In step S4, one pulse off the pulses P of the motor drive pulse signal is supplied from the motor driver 38 to the stepping motor 39, and the count value CT of the amount of pulses supplied to the stepping motor 39 is incremented.

In step S5, it is decided whether or not the edge of the slit 45a of the slit disk 45 is detected by the photosensor 37. Consequently, when the edge is detected, the program flow proceeds to step S6. Otherwise, the program flow returns to step S3.

In step S6, it is decided whether or not the content of the edge number PT is "0", i.e., whether or not the present edge is the first edge from the start of the rotation of the slit disk 45. Consequently, when the present edge is the first edge, the program flow proceeds to step S7. Otherwise, the program flow proceeds to step S8 to enter into a routine of specifying the detected edge.

In step S7, since the first edge has already passed, the content of the count value CT is set in the content of the edge number PT. Then the content of the count value CT is cleared to "0". Thereafter, the program flow returns to step S3 to enter into a process of detecting the next edge.

In step S8, the content of an address number N1 stored in the RAM 43 is initialized to "0".

In the above case, the address number N1 indicates an address of a table in the RAM 43 in which the combination of the slit length $a_i$ and the slit interval $b_i$ of the slit 45a is stored.

In step S9, it is decided whether or not the type of the edge detected in step S45 is the leading edge (at which the output of the photosensor 37 changes from a low level to a high level) in the direction of rotation. Consequently, when the edge is the leading edge, the program flow proceeds to step S12. When the edge is the trailing edge, the program flow proceeds to step S10.

In step S10, since the concerned edge is the trailing edge, a value SL[N1] of the slit length $a_i$ stored in the address number N1 of the table in the RAM 43 is read, and then it is decided whether or not the slit length SL[N1] is equal to the count value CT (measured actual value of the slit length $a_i$ according to the amount of pulses). Consequently, when they are equal to each other, the program flow proceeds to step S16. Otherwise, the program flow proceeds to step S11.

In step S11, the address number N1 is incremented, and thereafter the program flow returns to step S10 to compare the count value CT with the slit length $a_i$ stored in the next address.

In step S12, since the concerned edge is the leading edge, a value SS[N1] of the slit interval $b_i$ stored in the address number N1 of the table in the RAM 43 is read, and it is decided whether or not the slit interval SS[N1] is equal to the count value CT (measured actual value of the slit interval $b_i$ according to the amount of pulses). Consequently, when they are equal to each other, the program flow proceeds to step S14. Otherwise, the program flow proceeds to step S13.

In step S13, the address number N1 is incremented, and thereafter the program flow returns to step S12 to compare the count value CT with the slit interval $b_i$ stored in the next address.

In step S14, the amount of pulses PB1[N1] in an interval from the first edge to the concerned edge is set in the count value CT of the pulses P of the motor drive pulse signal supplied to the stepping motor 39.

For instance, it is assumed that the address number N1 is "2" when it is decided that the count value CT is equal to the slit interval SS[N1] in step S12. In the above case, the slit length $a_i$ and the slit interval $b_i$ stored in the address numbers "0" and "1" of the table in the RAM 43 are summed up to calculate the amount of pulses PB1[2] in a manner as follows.

$$PB1[2] = a_1 + b_1 + a_2 + b_2$$
$$= 3 + 19 + 4 + 18$$
$$= 44$$

Therefore, the value of "44" is set in the count value CT.

In step S15, the edge number is calculated based on the address number N1 according to the following equation, and set as the edge number PT.

$$PT = 2 \times N1 + 1$$

In step S16, the amount of pulses PB1[N1] in the interval from the first edge to the concerned edge is set in the count value CT.

For instance, it is assumed that the address number N1 is "2" when it is decided that the count value CT is equal to the slit width SL[N1] in step S10. In the above case, the slit length $a_i$ and the slit interval $b_i$ stored in the address numbers "0" and "1" and the slit length $a_i$ stored in the address number "2" of the table in the RAM 43 are summed up to calculate the amount of pulses PB1[2] in a manner as follows.

$$PB1[2] = a_1 + b_1 + a_2 + b_2 + a_3$$
$$= 3 + 19 + 4 + 18 + 5$$
$$= 49$$

Therefore, the value of "49" is set in the count value CT.

In step S17, the edge number is calculated based on the address number N1 according to the following equation, and set as the edge number PT.

$$PT = 2 \times N1 + 2$$

In step S18, a phase with respect to a reference point of the leading edge (the edge corresponding to the edge number PT of "1") in the direction of rotation at the first slit is calculated based on the content of the set count value CT according to the following equation.

$$\text{Phase} = 360° \times (CT/400)$$

Thereafter, a variety of operations such as the erroneous tube placement detection necessary for driving the fluid infusion pump (the operations referred to as "fluid pumping operations" hereinafter) are executed based on the calculated phase angle, and then the rotational position detecting operation is completed.

In other words, according to the present embodiment, the aforementioned rotational position detecting means is comprised of the step S5 through step S17, and the slit specifying means is comprised particularly of the step S10 through step S13, step S15, and step S17.

According to the present embodiment as described above, by setting up the amount of pulses PB1[N1] in the interval from the first edge to the concerned edge and the edge number PT of the concerned edge at the point of time when the second edge is detected from the time when the stepping motor 39 has started to rotate, the slit 45a located in the position of the photosensor 37 is specified to detect the rotational position of the motor. With the above-mentioned arrangement, the detection of the rotational position can be achieved with high accuracy in a short time even at a low flow rate of 0.1 ml/hr or in a similar case to allow the dead band to be correctly detected when the power is turned on and thereby allow the fluid transfer to be stably performed.

Second embodiment

Then the following describes a second embodiment related to the detection of the rotational position of the motor.

Figure 10:
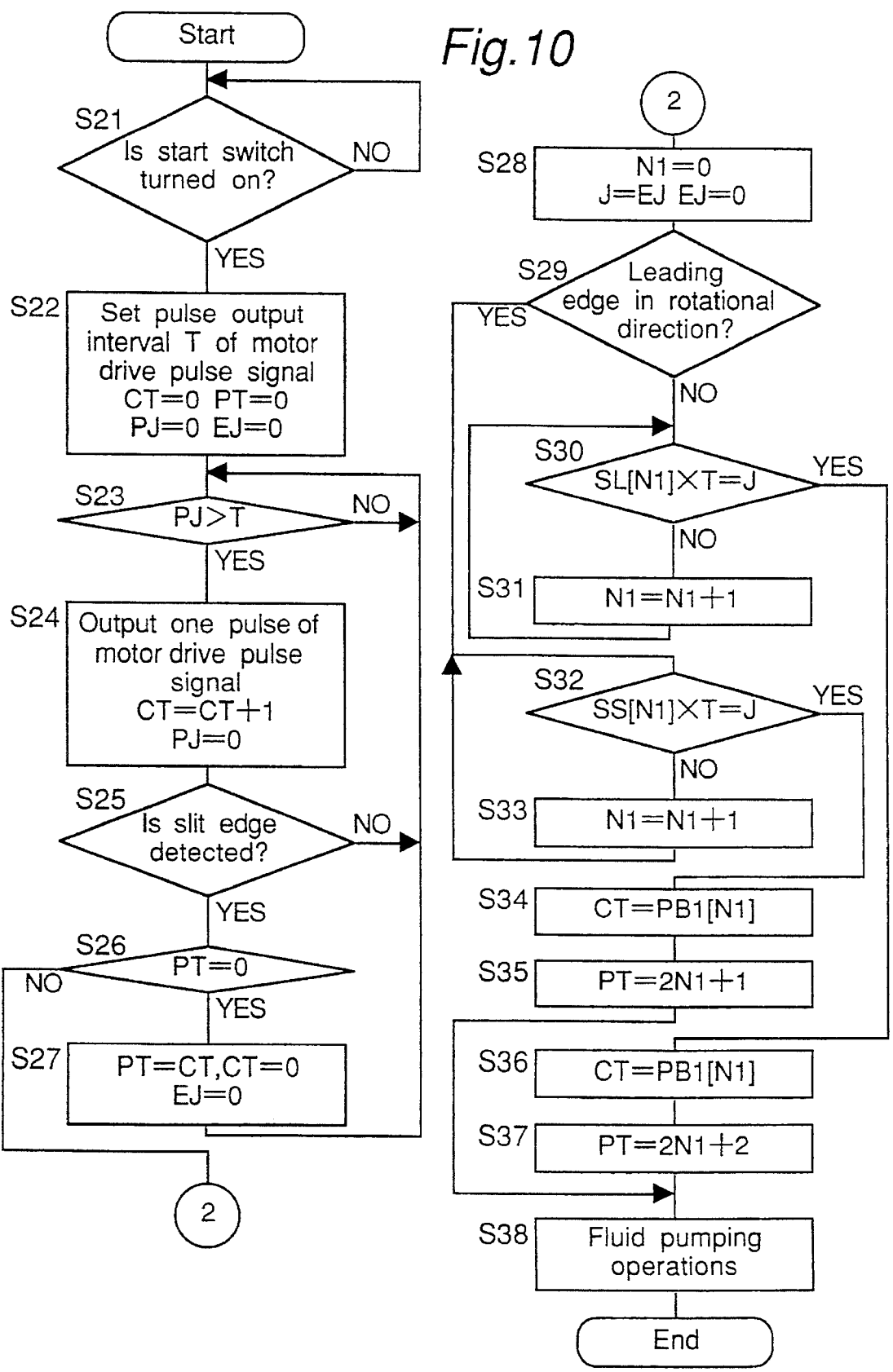
FIG. 10 is a flowchart of a motor rotational position detecting operation of the fluid infusion pump different from the flowchart of FIG. 9.

FIG. 10 is a flowchart of a rotational position detecting operation executed under the control of the CPU 31 in the second embodiment.

In step S21, it is decided whether or not the start switch is turned on. When the start switch is turned on, the program flow proceeds to step S22.

In step S22, a pulse output interval time T of the motor drive pulse signal supplied to the stepping motor 39 is set by means of the motor driven 39 based on the set flow rate Y (ml/hr) which has been inputted from the key switch 35 and stored in the RAM 43 according to the following equation.

$$T = 3600/4000 \, Y \text{ (sec)}$$

Then the contents of the count value CT and the edge number PT stored in the RAM 4B are initialized to "0", and a after-pulse-application elapsed time PJ and a after-edge-detection elapsed time EJ counted by the timer 41 are reset. The after-pulse-application elapsed time PJ and the after-edge-detection elapsed time EJ are automatically incremented.

In step S23, it is decided whether or not the after-pulse-application elapsed time PJ which is an elapsed time from the time when one pulse of the pulses P of the motor drive pulse signal is supplied to the stepping motor 39 is exceeding the pulse output interval time T. Consequently, when the after-pulse-application elapsed time PJ is exceeding the pulse output interval time T, the program flow proceeds to step S24.

In step S24, one pulse of the pulses P of the motor drive pulse signal is supplied from the motor driver 38 to the stepping motor 39, and the count value CT is incremented. Meanwhile, the after-pulse-application elapsed time PJ is cleared.

In step S25, it is decided whether or not the edge of the slit 45a of the slit disk 45 is detected by the photosensor 37. Consequently, when the edge is detected, the program flow proceeds to step S26. Otherwise, the program flow returns to step S23.

In step S26, it is decided whether or not the content of the edge number PT is "0" and represents the first edge. Consequently, when the edge is the first edge, the program flow proceeds to step S27. Otherwise, the program flow proceeds to step S28 to enter into a routine of specifying the detected edge.

In step S27, since the first edge has been already passed, the content of the count value CT is set in the content of the edge number PT, and the content of the count value CT is cleared to "0". Then the after-edge-detection elapsed time EJ is reset. Thereafter, the program flow returns to step S23 to enter a process of detecting the next edge.

In step S28, the content of the address number N1 stored in the RAM 43 is initialized to "0", and the content of the after-edge-detection elapsed time EJ is set in the elapsed time J. Thereafter, the after-edge-detection elapsed time EJ is reset.

In the above case, the address number N1 is the address of the table in the RAM 43 which stores the combination of the slit length $a_i$ (expressed in the amount of pulses) and the slit interval $b_i$ (expressed in the amount of pulses) of the slit 45a as described above.

In step S29, it is decided whether or not the type of the edge detected in step S25 is the leading edge in the direction of rotation. Consequently, when the edge is the leading edge, the program flow proceeds to step S32. When the edge is the trailing edge, the program flow proceeds to step S30.

In step S30, since the concerned edge is the trailing edge, the value SL[N1] of the slit length $a_i$ stored in the address number N1 of the table in the RAM 43 is read. Then it is decided whether or not the elapsed time J (measured actual value of the slit length $a_i$ in terms of time) is equal to the "slit width SL[N1]×T". When they are equal to each other, the program flow proceeds to step S36. Otherwise, the program flow proceeds to step S31.

In step S31, the address number N1 is incremented, and then the program flow returns to step S30 to compare the measured actual value with the slit length $a_i$ stored in the next address.

In step S32, since the concerned edge is the leading edge, the value SS[N1] of the slit interval $b_i$ stored in the address number N1 of the table in the RAM 43 is read. Then it is decided whether or not the elapsed time J (measured actual value of the slit interval $b_i$ in terms of time) is equal to the "slit interval SS[N1]×T". When they are equal to each other, the program flow proceeds to step S34. Otherwise, the program flow proceeds to step S33.

In step S33, the address number N1 is incremented, and then the program flow returns to step S32 to compare the measured actual value with the slit interval $b_i$ stored in the next address.

In step S34, the amount of pulses PB1[N1] in the interval from the first edge to the concerned edge is set in the count value CT.

In the above case, the amount of pulses PB1[N1] is calculated by the same method as the calculation method described in step S14 of the first embodiment.

In step S35, a value calculated based on the address number N1 by the same method as in step S15 of the first embodiment is set in the edge number PT.

In step S36, the amount of pulses PB1[N1] in the interval from the first edge to the concerned edge is set in the count value CT.

In the above case, the amount of pulses PB1[N1] is calculated by the same method as the calculation method described in step S16 of the first embodiment.

In step S37, a value calculated based on the address number N1 by the same method as in step S17 of the first embodiment is set in the edge number PT.

In step S38, a phase with respect to the reference point of the leading edge in the direction of rotation at the first slit is calculated based on the content of the set count value CT according to the following equation.

$$\text{Phase} = 360° \times (CT/400)$$

Thereafter, a variety of fluid pumping operations necessary for driving the fluid infusion pump are executed based on the calculated phase angle, and then the rotational position detecting operation is completed.

In other words, according to the second embodiment, the aforementioned rotational position detecting means is comprised of the step S25 through step S37, and the slit specifying means is comprised particularly of the step S30 through step S33, step S35, and step S37.

As described above, in contrast to the first embodiment in which the detection of the rotational position of the motor is executed based on the amount of pulses of the motor drive pulse signal supplied to the stepping motor 39, the amount of pulses is managed in terms of time in the present second embodiment.

Third embodiment

Then the following describes a third embodiment related to an erroneous tube placement detecting operation.

Figure 12:
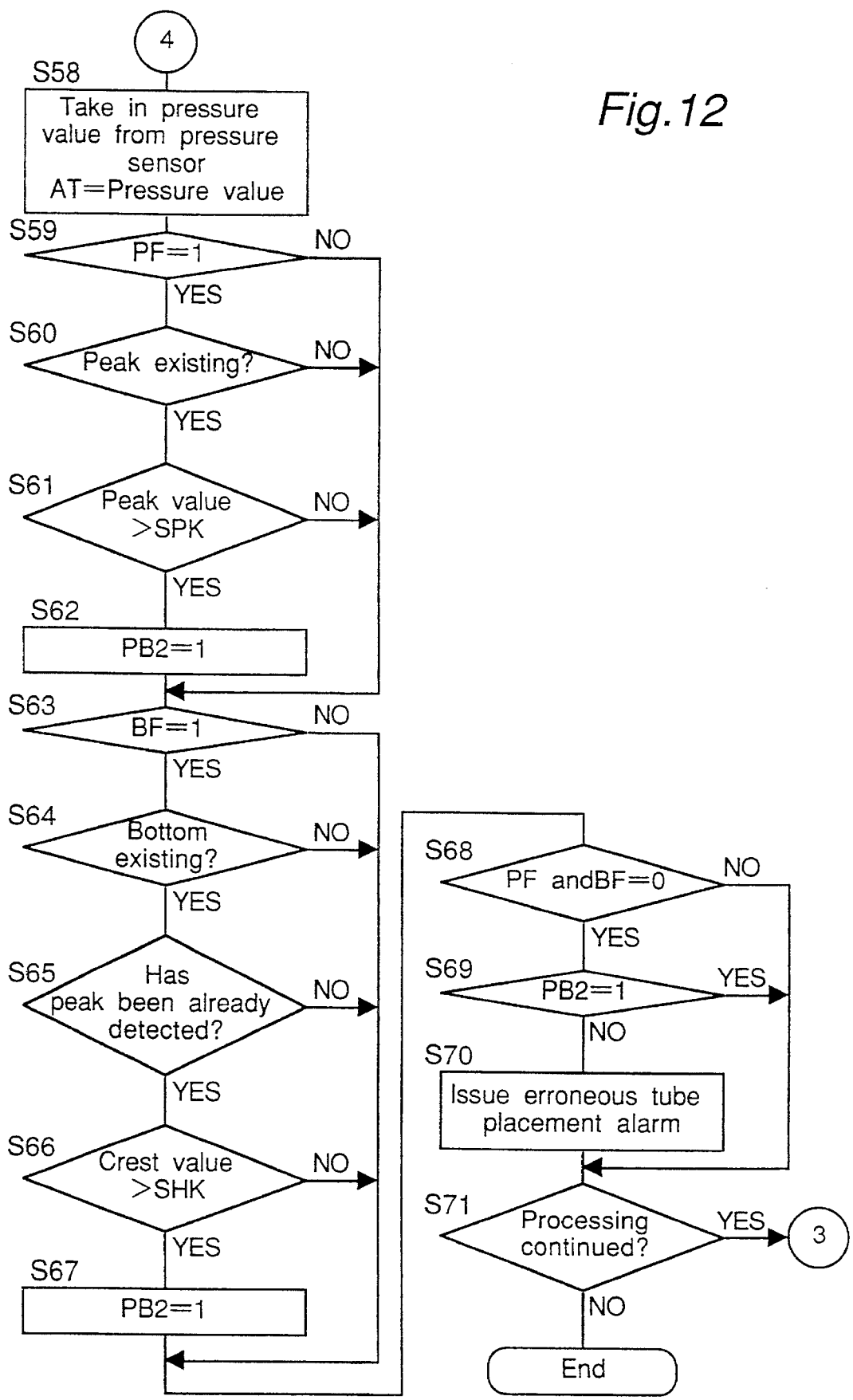
FIG. 12 is a flowchart of the erroneous tube placement detecting operation continued from the flowchart of FIG. 11.

FIGS. 11 and 12 are flowcharts of the erroneous tube placement detecting operation executed under the control of the CPU 31. The following describes in detail the erroneous tube placement detecting operation with reference to FIGS. 11 and 12.

In step S41, it is decided whether or not the start switch is turned on. When the start switch is turned on, the program flow proceeds to step S42.

In step S42, the pulse output interval time of the motor drive pulse signal supplied to the stepping motor 39 is set by the motor driver 38 in the same manner as in step S2 of the first embodiment.

Then the contents of the count value CT, the edge number PT, a reference peak value SPK, and a reference crest value SHK are each initialized to "0", and the content of an erroneous tube placement decision flag PB2 is initialized to "1".

In step S43 through step S47, supplying of the pulses P of the motor drive pulse signal to the stepping motor 39, incrementing of the count value CT, and detecting of the edge of the slit 45a are executed in the same manner as in step S3 through step S7 of the rotational position detecting operation of the first embodiment. When the second edge is detected, the program flow proceeds to step S48.

In step S48, specifying of the rotational position of the slit disk 45 (i.e., the rotational position of the stepping motor 39) and setting of the count value CT and the edge number PT are executed in the same manner as in step S8 through step S17 of the rotational position detecting operation of the first embodiment.

Thus the rotational position of the stepping motor 39 is specified through the aforementioned steps, and then the program flow enters into the erroneous tube placement detecting operation.

In step S49, it is decided whether or not the aforementioned output time is exceeding a specified time. Consequently, when the output time is exceeding the specified time, the program flow proceeds to step S50.

In step S50, one pulse of the pulses P of the motor drive pulse signal is supplied from the motor driver 38 to the stepping motor 39, and the count value CT is incremented.

In step S51, it is decided whether or not the edge of the slit 45a is detected. Consequently, when the edge is detected, the program flow proceeds to step S52. Otherwise, the program flow returns to step S49 to continue the edge detecting operation.

In step S52, the edge number PT is incremented.

In step S53, it is decided whether or not the content of the count value CT is not smaller than a value of 400. Consequently, when the value is not smaller than the value of 400, the program flow proceeds to step S54. Otherwise, the step S54 is skipped.

In step S54, it is decided that the stepping motor 39 has made one turn since the count value CT has reached the value of 400, and the contents of the count value CT and the edge number PT are cleared.

In step S55, a reference peak value of a pressure waveform in the vicinity of the present rotational position of the motor is read from the corresponding table of the RAM 43 based on the count value CT or the edge number PT set in step S50 and step S52, or in step S54, and then set in the reference peak value SPK. Then the peak value (reference crest value) ranging from the peak to the bottom relevant to the present reference peak value is read and set in the reference crest value SHK.

It is to be noted that the reference peak value and the reference crest value are respectively the peak value of a peak in the vicinity of a specified rotational position of the pressure waveform (refer to FIG. 3A) detected by the pressure sensor 16 when the tube is correctly placed and the minimum value that the crest value can take in the range from the peak to the bottom.

When the rotational position is located in the vicinity of a position at which a peak of the pressure waveform exists, a value of "1" is set in a peak flag PF. When the rotational position is located in the vicinity of a position at which a bottom exists, a value of "1" is set in a bottom flag BF. When the rotational position is located in a position other than the position in the vicinity of the position at which the peak exists or in the vicinity of the position at which the bottom exists, a value of "0" is set in the peak flag PF or the bottom flag BF.

In step S56, it is decided whether or not the content of the peak flag PF or the bottom flag BF is "1". Consequently, when the content is "1", the program flow proceeds to step S57. Otherwise, the step S57 is skipped.

In step S57, a value of "0" is set in the erroneous tube placement decision flag PB2.

In step S58, the pressure value from the pressure sensor 16 is taken in, and then set in a pressure value AT.

In step S59, it is decided whether or not the content of the peak flag PF is "1" (i.e., whether the present rotational position is located in the vicinity of the position at which the peak exists). Consequently, when the content is "1", the program flow proceeds to step S60. Otherwise, the program flow proceeds to step S63 to enter into a process of checking a portion in the vicinity of the bottom.

In step S60, it is decided whether or not a peak exists in the pressure waveform in the vicinity of the present rotational position based on the pressure value taken in in step S58. Consequently, when a peak exists, the program flow proceeds to step S61. Otherwise, the program flow proceeds to step S63 to enter into the process of checking a portion in the vicinity of the bottom.

In step S61, it is decided whether or not the voltage value of the peak detected in step S60 is higher than the reference peak value SPK. Consequently, when the detected peak is higher than the reference peak value SPK, the program flow proceeds to step S62. Otherwise, the program flow proceeds to step S63 to enter into the process of checking a portion in the vicinity of the bottom.

In step S62, it is decided that the peak detected in step S60 is a peak owing to the fact that a finger 20 correctly press the tube 23, and a value of "1" is set in an erroneous tube placement decision flag P21. Thus it is decided that the tube 23 is correctly placed in the vicinity of the finger 20 pressing the tube 23 in the present rotational position of the motor.

In step S63, it is decided whether or not the content of the bottom flag BF is "1" (i.e., whether the present rotational position is located in the vicinity of the position at which the bottom exists). Consequently, when the content is "1", the program flow proceeds to step S64. Otherwise, the program flow proceeds to step S68.

In step S64, it is decided whether or not a bottom exists in the pressure waveform in the vicinity of the present rotational position based on the pressure value taken in in step S58. Consequently, when a bottom exists, the program flow proceeds to step S65. When no bottom exists, the program flow proceeds to step S68.

In step S65, it is decided whether or not the peak in the pressure waveform has been already detected. Consequently, when a peak has been detected, the program flow proceeds to step S66. Otherwise, the program flow proceeds to step S68.

In step S66, it is decided whether or not the crest value of a range from the previous peak to the present bottom is higher than the reference crest value SHK. When the crest value is higher than the reference crest value SHK, the program flow proceeds to step S67. Otherwise, the program flow proceeds to step S68.

In step S67, it is decided that the bottom detected in step S64 is the correct bottom, and a value of "1" is set in the erroneous tube placement decision flag PB2. Thus it is decided that the tube 23 is correctly placed in the vicinity of the present rotational position of the motor.

In step S68, it is decided whether or not the contents of the peak flag PK and the bottom flag BF are both "0". Consequently, when the contents are both "0", the program flow proceeds to step S71. Otherwise, the program flow proceeds to step S69.

In step S69, it is decided whether or not the content of the erroneous tube placement decision flag PB2 is "1". Consequently, when the content is "1", it is decided that the erroneous tube placement is not occurring since a peak or a bottom has been previously detected, and then the program flow proceeds to step S71. When the content is not "1", it is decided that the erroneous tube placement is occurring since neither a peak nor a bottom has been detected, and then the program flow proceeds to step S70.

In step S70, an erroneous tube placement alarm is outputted to the I/O driver 34, and the buzzer 36 (refer to FIG. 5) issues an alarm sound.

In step S71, it is decided whether or not the erroneous tube placement detecting operation is to be continued. When the operation is consequently continued, the program flow returns to step S49 to enter into a process of detecting the next edge. Otherwise, the erroneous tube placement detecting operation is completed.

In other words, the erroneous placement deciding means is comprised of the step S58 through step S70 in the present third embodiment.

In the present third embodiment as described above, the slit disk 45 is mounted to the upper end portion of the shaft 18 in the fluid pumping section 11. Every time the edge of the slit 45a of the slit disk 45 is detected by the photosensor 37, the rotational position of the motor is detected based on the amount of pulses of the motor drive pulse signal supplied to the stepping motor 39 from the time when the previous edge has been detected and the type of the edge, and the erroneous tube placement is detected based on the reference peak value and the reference crest value relevant to the present rotational position stored in the RAM 43.

Therefore, according to the present embodiment, it can be decided whether the erroneous tube placement is occurring every time an edge is detected to allow the erroneous tube placement to be detected with high accuracy even at a low flow rate of 0.1 ml/hr.

In the above case, when only the slit length $a_i$ of the slit 45a is gradually increased, the rotational position of the motor can be detected, whereas the cycle of detecting the erroneous tube placement is accordingly increased. Therefore, conversely the slit interval $b_i$ is gradually reduced to achieve a proper balance.

Fourth embodiment

Then the following describes a fourth embodiment related to the motor rotating speed controlling operation.

Normally, when the stepping motor 39 is driven at a regular pulse output interval time T as in the case of the second embodiment, a dead band is generated to cause the fluid flow rate to be varied depending on a timing of pressing the tube 23 by the fingers 20.

Therefore, in the present embodiment, the rotating speed of the stepping motor 39 is controlled by decreasing or increasing the pulse output interval time T in correspondence with the slit it length $a_i$ and the slit interval $b_i$ of the slit 45a. A decreasing or increasing ratio (referred to as a "correction ratio" hereinafter) in the above case is stored in a table in the RAM 43 as set in a manner as follows in correspondence with ($a_i$, $b_i$). It is to be noted that the set values of the correction ratio are each denoted in terms of percentage (%).

($STa_i$, $STb_i$):  (5, 5)→(5, 5)→(5, 5)→(120, 120)→
 (150, 80)→(120, 120)→(140, 80)→(120, 120)→
 (130, 80)→(120, 120)→(140, 100)→(120, 120)→
 (150, 90)→(120, 120)→(140, 120)→(120, 120)→
 (150, 80)→(120, 120)→(5, 5)

Therefore, assuming that the amount of pulses of the motor drive pulse signal outputted in the time of the slit length $a_i$ is $Z_{ai}$ (=$a_i$) and the set flow rate is Y (ml/hr) in the present fourth embodiment, the above-mentioned time of the slit length ai can be expressed as follows.

$$\{3600/(4000\times Y)\}\times Z_{ai}\times ((ST_{ai})/100)$$

Furthermore, assuming that the correction ratio of the slit length $a_i$ or the slit interval $b_i$ relevant to a correction pulse output interval time Th is X, the interval time Th can be expressed as follows.

$$Th=3600/(4000\times Y)\times (X/100)$$

In the above case, assuming that a pulse amount relevant to the jth edge is P[j]=($a_j$, $b_j$) and the correction ratio relevant to the jth edge is ST[j]=($ST_{aj}$, $ST_{bj}$), the following equation:
Equation 1:

$$\sum_{j=1}^{38} (P[j]\times ST[j]) = 40000$$

holds, producing the same result as in the case where the stepping motor 39 is driven with the pulse output interval time T corrected at a correction ratio of 100%. Therefore, no error is generated in the flow rate due to the motor rotating speed controlling operation of the present fourth embodiment.

Figure 13:
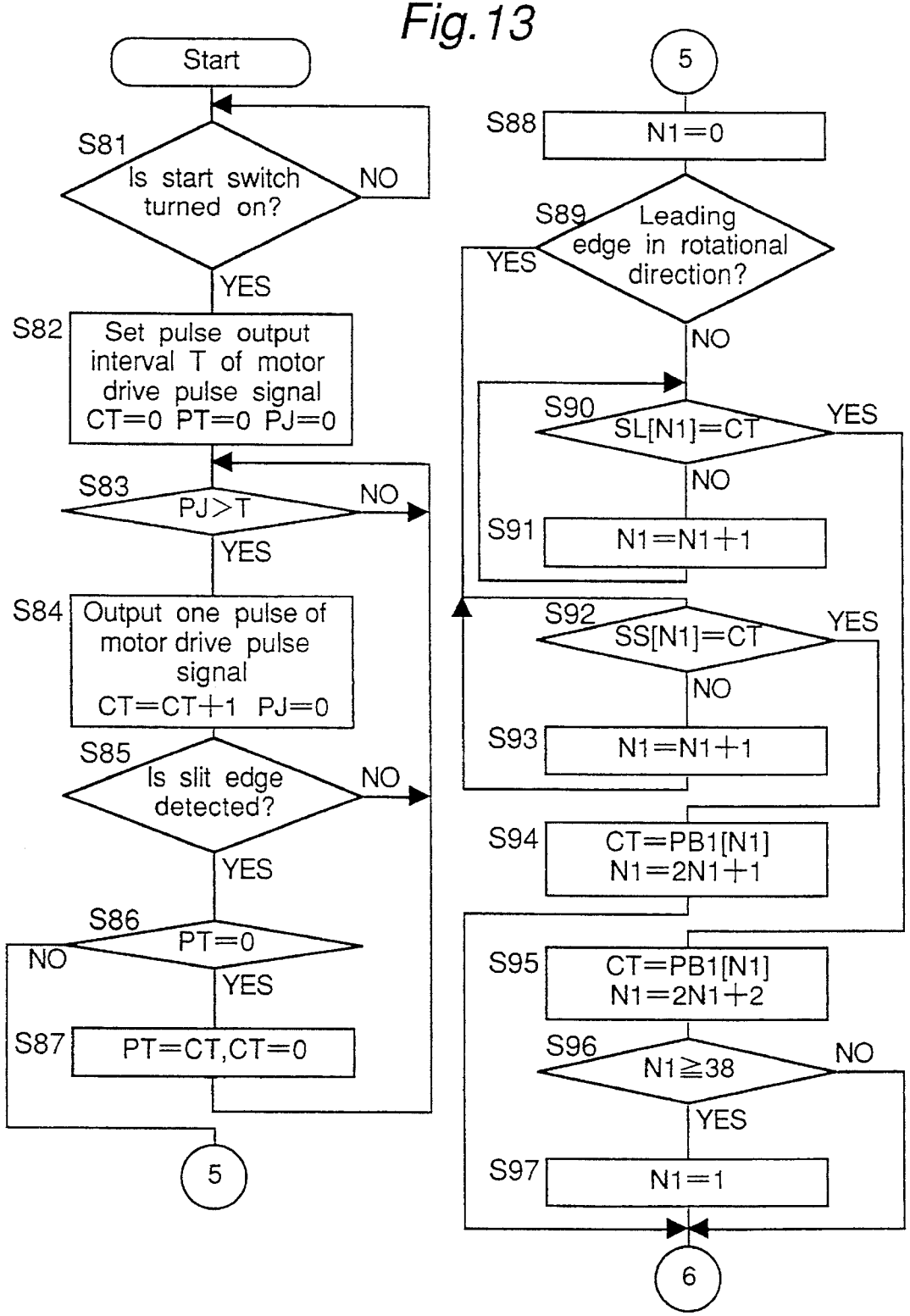
FIG. 13 is a flowchart of a motor rotating speed controlling operation of the fluid infusion pump.
Figure 14:
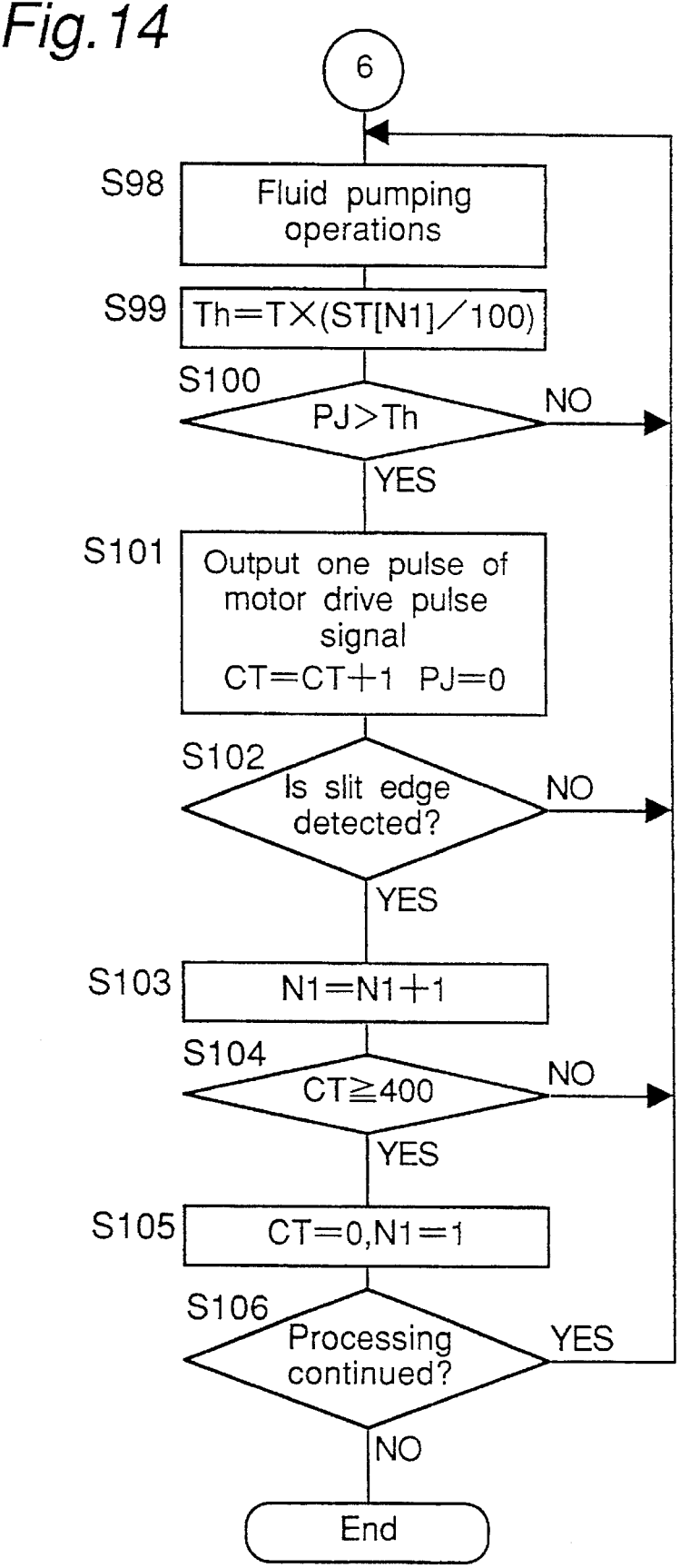
FIG. 14 is a flowchart of the motor rotating speed controlling operation continued from the flowchart of FIG. 13.

FIGS. 13 and 14 are flowcharts of the motor rotating speed controlling operation executed under the control of the CPU 31.

In step S81, it is decided whether or not the start switch is turned on. When the start switch is turned on, the program flow proceeds to step SS2.

In step S82, the pulse output interval time T is set based on the set flow rate Y (ml/hr) stored in the RAM 43 in the same manner as in step S22 of the second embodiment.

Then the contents of the count value CT and the edge number PT stored in the RAM 43 are initialized to "0",. and the after-pulse-application elapsed time PJ is reset.

In step S83 through step S87, one pulse of the pulses P of the motor drive pulse signal is outputted to drive the stepping motor 39 in the same manner as in step S23 through step S27 in the rotational position detecting operation of the second embodiment. When the edge of the slit 45a is detected two times, the program flow proceeds to step S88.

In step S88 through step S93, decision of the type of the edge of the slit 45a, comparison of a measured actual value corresponding to the amount of pulses of the slit length $a_i$ with the slit length SL[N1], and comparison of a measured actual value corresponding to the amount of pulses of the slit interval $b_i$ with the slit interval SS[N1] are executed in the same manner as in step S8 through step S13 in the rotational position detecting operation of the first embodiment. When the measured actual value of the slit length $a_i$ is equal to the slit length SL[N1], the program flow proceeds to step S97. When the measured actual value of the slit interval $b_i$ is equal to the slit interval SS[N1], the program flow proceeds to step S94.

In step S94, the amount of pulses PB1[N1] in the interval from the first edge to the concerned edge is set in the count value CT in the same manner as in step S14 and step S15 of the first embodiment. Then the content of the address number N1 is renewed according to the edge number calculated based on the address number N1. Thereafter, the program flow proceeds to step S98.

In contrast to the fact that the address number N1 prior to the renewal represents the address in which the data ($a_i$, $b_i$) of a combination of the slit length $a_i$ and the slit interval $b_i$ is stored, the address number N1 after the renewal represents the address in which each of the correction ratio $ST_{si}$ of the slit length $a_i$ or the correction ratio $ST_{bi}$ of the slit interval $b_i$ are stored In the present fourth embodiment, the correction ratio $ST_{si}$ and the correction ratio $ST_{bi}$ are stored in consecutive addresses.

In step S95, the amount of pulses PB1[N1] in the interval from the first edge to the concerned edge is set in the count value CT in the same manner as in step S16 and step S17 of the first embodiment. Then the content of the address number N1 is renewed according to the edge number calculated based on the address number N1.

In step S96, it is decided whether or not the content of the address number N1 is not smaller than "38", i.e., whether the address number has reached the last address. Consequently, when the address number has not reached the last address, the program flow proceeds to step S98. Otherwise, the program flow proceeds to step S97.

In step S97, since the content of the address number N1 has reached the last address, the first address number "1" is set in the address number N1. Thereafter, the program flow proceeds to step S98.

In step S98, the count value CT set in the above-mentioned manner corresponds to a phase with respect to the reference point of the leading edge in the direction of rotation at the first slit as understood from the following equation.

Phase=360°×(CT/400)

Therefore, the aforementioned fluid pumping operations necessary for driving the fluid infusion pump are executed based on the count value CT.

Thus the rotational position of the stepping motor 39 is detected through the aforementioned steps. Subsequently, in order to make the fluid flow rate linear by removing the dead band, the program flow enters into a motor rotating speed controlling process based on the detected rotational position of the stepping motor 39.

In step S99, the value ST[N1] of the correction ratio $ST_{ai}$ or the correction ratio $ST_{bi}$ stored in the corresponding table in the RAM 43 is read based on the address number N1 calculated in step S94 or step S95. Then the correction pulse output interval time Th relevant to one pulse of the motor drive pulse signal subsequently supplied to the stepping motor 39 is calculated according to the following equation.

Th=T×(ST[N1]/100)

In step S100, it is decided whether or not the after-pulse-application elapsed time PJ is longer than the correction pulse output interval time Th. In other words, it is decided whether or not the correction pulse output interval time Th has elapsed from the time when the pulse P of the motor drive pulse signal has been previously outputted. Consequently, when the correction pulse output interval time Th has elapsed, the program flow proceeds to step S101. Otherwise, the program flow returns to step S98 to continue the fluid pumping operations.

In step S101, one pulse of the pulses P of the motor drive pulse signal is supplied to the stepping motor 39. Thus the one pulse of the pulses P of the motor drive pulse signal is outputted in accordance with a timing obtained by increasing or decreasing the normal pulse output interval time T according to the correction ratio ST[N1] to thereby control the rotating speed of the stepping motor 39.

Thereafter, the content of the count value CT is incremented, and the after-pulse-application elapsed time PJ is reset.

In step S102, it is decided whether or not the edge of the slit 45a is detected by the photosensor 37. Consequently, when the edge is detected, the program flow proceeds to step S103. Otherwise, the program flow returns to step S98 to continue the fluid pumping operations.

In step S103, the content of the address number N1 is incremented.

In step S104, it is decided whether or not the content of the count value CT is not smaller than a value of 400. Consequently, when the content is not smaller than the value of 400, the program flow proceeds to step S105. Otherwise, the program flow returns to step S98 to execute the fluid pumping operations, and the pulse P is outputted in accordance with a timing based on the correction ratio stored in the next address.

In step S105, since the stepping motor 39 has made one turn, the content of the count value CT is cleared to "0", and the first address "1" is set in the address number N1.

In step S106, it is decided whether or not the motor rotating speed controlling operation is to be continued. Consequently, when the above-mentioned operation is continued, the program flow returns to step S98, and the pulse P is outputted in accordance with a timing based on the correction ratio stored in the first address. Otherwise, the motor rotating speed controlling operation is completed.

In other words, according to the present fourth embodiment, the aforementioned time setting means is comprised of the step S99, and the motor driving means is comprised of the step S100 and step S101.

In the present fourth embodiment as described above, the rotational position of the stepping motor 39 is detected at the second edge of the slit after the stepping motor 39 has started. Subsequently, every time an edge is detected, the pulse P of the motor drive pulse signal is supplied to the stepping motor 39 in accordance with a timing obtained by decreasing or increasing the pulse output interval time T at the correction ratios $ST_{ai}$ and $ST_{bi}$ of the concerned edge to control the rotating speed of the stepping motor 39.

In the above case, by mounting the slit disk 45 to the shaft 18 so that the first slit to the third slit at which the correction ratios $ST_{ai}$ and $ST_{bi}$ are set at 5% pass through the position of the photosensor 37 in the dead band, the correction pulse output interval time Th in the dead band is remarkably reduced in comparison with the normal pulse output interval time T to increase the rotating speed of the stepping motor 39.

Consequently, the period in which the #10 finger $20_{10}$ located in the lowermost position presses the tube 23 can be reduced, and the fluid pumping section 11 operates as if the dead band does not exist.

In other words, according to the present fourth embodiment, by detecting the rotational position of the motor corresponding to the dead band prior to the time when the stepping motor 39 makes one turn when the power is turned on to increase the rotating speed of the stepping motor 39, the dead band condition can be eliminated. Furthermore, the fluid flow rate can be controlled every slit 45a of the slit disk 45, and by setting in optimum the values of the correction ratios $ST_{ai}$ and $ST_{bi}$, the change of flow rate when the stepping motor 39 makes one turn can be brought closer to the liner change.

When the fluid transfer speed characteristic varies depending on each fluid infusion pump, the fluid transfer speed characteristic of each fluid infusion pump can be made identical by setting the correction ratios of each fluid infusion pump so as to correct the variation of the fluid transfer speed characteristic.

Furthermore, by setting the correction ratios for every output of one pulse of the motor drive pulse signal, the rotating speed of the stepping motor 39 can be controlled every one pulse P.

Furthermore, by making the seep S81 through step S97 of the flowchart shown in FIG. 13 similar to the step S21 through step S37 of the flowchart shown in FIG. 10, the rotational position of the motor can be detected by time.

Fifth embodiment

Then the following describes an fifth embodiment related to the motor driving torque controlling operation.

In the present fifth embodiment, a combination $(a_i, b_i)$ of the slit length $a_i$ and the slit interval $b_i$ of each slit 45a provided at the slit disk 45 is stored in the table of the RAM 43 as arranged in a manner as follows in the same manner as in each of the aforementioned embodiments.

$(a_i, b_i)$: (3, 19)→(4, 18)→(5, 17)→(6, 16)→
(7, 15)→(8, 14)→(9, 13)→(10, 12)→
(11, 11)→(12, 10)→(13, 9)→(14, 8)→
(15, 7)→(16, 6)→(17, 5)→(18, 4)→
(19, 3)→(21, 1)→(2, 2)

The stepping motor 39 makes one turn in 400 pulses of the motor drive pulse signal, where the torque required for making one turn differs depending on the rotational position. Therefore, in a period in which the motor can be driven at a low torque, the stepping motor 39 can be driven with a small drive current. Therefore, in the present fifth embodiment, the duty ratio of the pulses P of the motor drive pulse signal shown in FIG. 6D is controlled according to the required torque by the 20 kHz duty ratio control section 40 to set the drive current supplied to the stepping motor 39 at a low level.

In the above case, the duty ratio ($DT_{ai}$, $DT_{bi}$) is stored in the table of the RAM 43 as see in a manner as follows in correspondence with ($a_i$, $b_i$). It is to be noted that set values of the duty ratio are denoted in terms of percentage (%).

$(DT_{ai}, DT_{bi})$: (50, 50)→(55, 55)→(60, 65)→(60, 50)→
(45, 55)→(60, 55)→(70, 65)→(60, 50)→
(45, 50)→(55, 55)→(65, 65)→(60, 55)→
(55, 55)→(50, 55)→(65, 65)→(60, 50)→
(50, 60)→(65, 70)→(65, 60)

Figure 15:
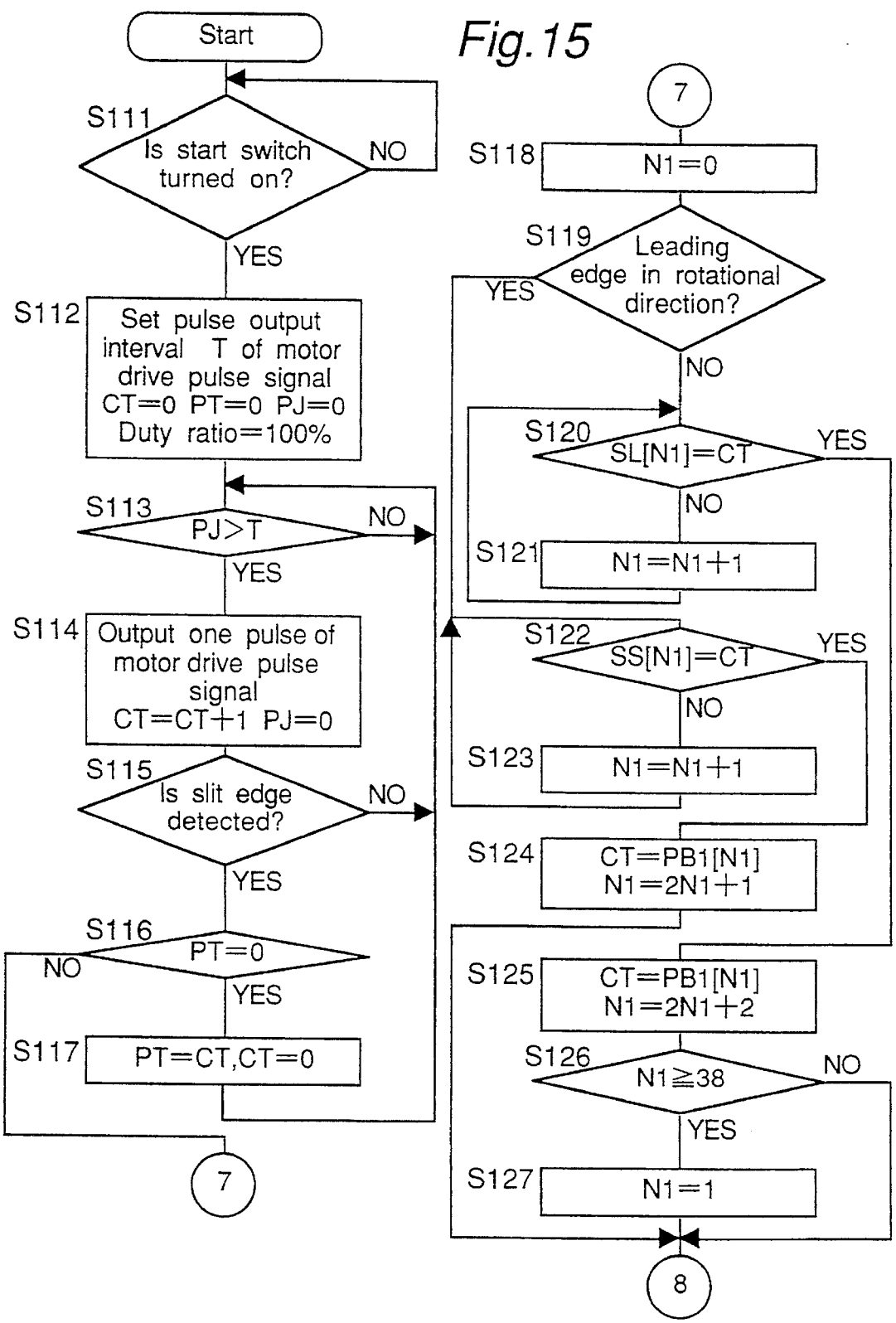
FIG. 15 is a flowchart of a motor driving torque controlling operation of the fluid infusion pump.
Figure 16:
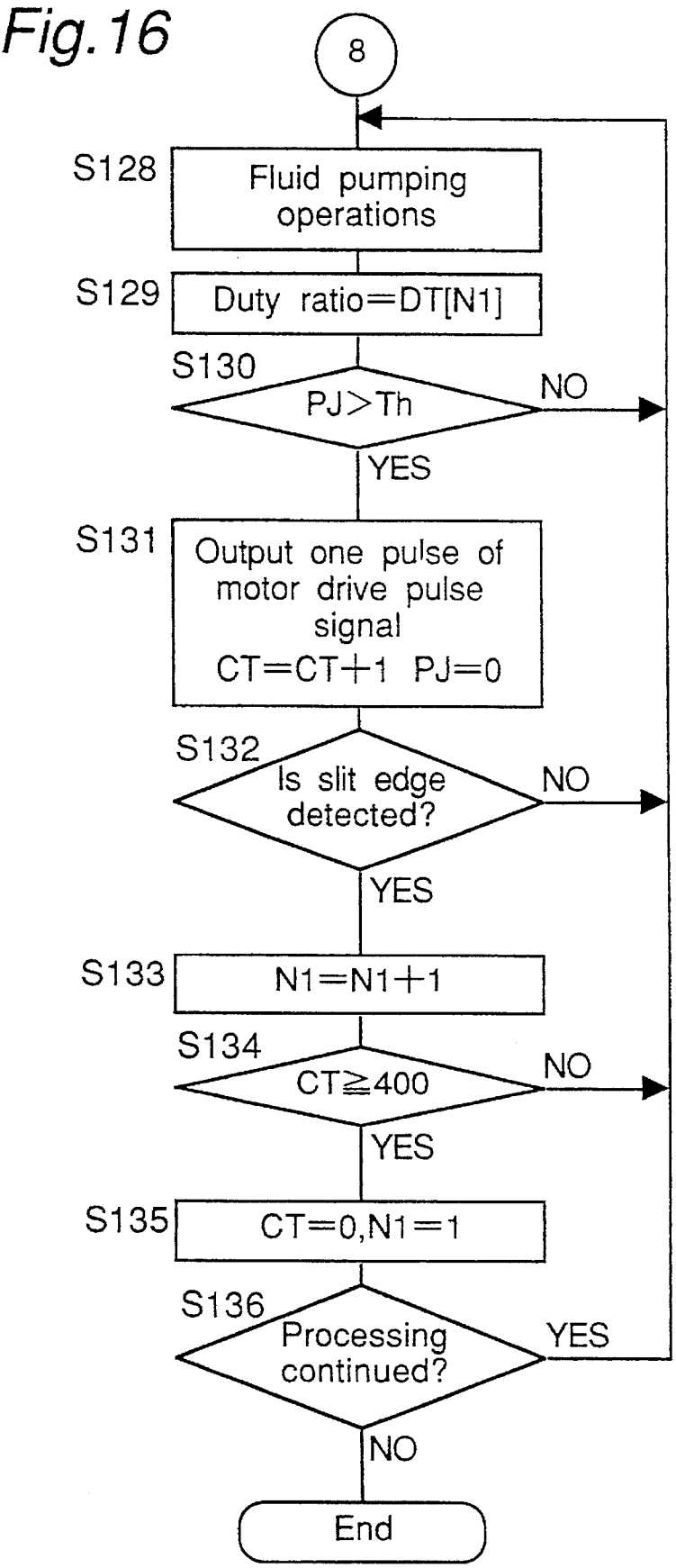
FIG. 16 is a flowchart of the motor driving torque controlling operation continued from the flowchart of FIG. 15.

FIGS. 15 and 16 are flowcharts of the motor driving torque controlling operation executed under the control of the CPU 31.

In step S111, it is decided whether or not the start switch is turned on. When the start switch is turned on, the program flow proceeds to step S112.

In step S112, the pulse output interval time T is set based on the set flow rate Y (ml/hr) stored in the RAM 43 in the same manner as in step S22 of the rotational position detecting operation of the second embodiment.

Then the contents of the count value CT and the edge number PT stored in the RAM 43 are initialized to "0", and the after-pulse-application elapsed time PJ is reset. Meanwhile, a command signal is outputted to the 20 kHz duty ratio control section 40 to initialize the duty ratio of the pulses P at 100%.

In step S113 through step S128, specifying of the edge detected in the second edge detecting stage, setting of the address N1 in which the duty ratio $DT_{ai}$ corresponding to the slit length $a_i$ or the duty ratio $DT_{bi}$ corresponding to the slit interval $b_i$ of the concerned edge is stored, setting of the amount of pulses PB1[N1] in the interval from the first edge to the concerned edge in the count value CT, and the fluid pumping operations are executed in the same manner as in step S83 through step S98 of the rotational position controlling operation of the fourth embodiment.

The rotational position of the stepping motor 39 is detected through the aforementioned steps. Subsequently, the program flow enters into a motor driving torque controlling process based on the detected rotational position of the stepping motor 39.

In step S129, the value DT[N1] of the duty ratio $DT_{ai}$ or the duty ratio $DT_{bi}$ stored in the corresponding table of the RAM 43 is read based on the address number N1 calculated in step S124 or step S125, and then transferred to the 20 kHz duty ratio control section 40.

In step S130 through step S136, when the after-pulse-application elapsed time PJ becomes longer than the pulse output interval time T in the same manner as in step S100 through step S106 of the fourth embodiment, one pulse of the pulses P of the duty ratio DT[N1] is supplied from the 20 kHz duty ratio control section 40 to the stepping motor 39, with which the stepping motor 39 is driven with the controlled drive current. Subsequently, every time an edge is detected, the duty ratio of the pulses P is controlled according to the duty ratio DT[N1] read from the RAM 43 to control the drive current.

In other words, the duty ratio setting means is comprised of the step S129 in the present fifth embodiment.

According to the present fifth embodiment as described above, the rotational position of the stepping motor 39 is detected at the second edge after the stepping motor 39 has started. Subsequently, every time an edge is detected, the duty ratio of the pulses P to be supplied to the stepping motor 39 is set at the duty ratio $DT_{ai}$, $DT_{bi}$ of the concerned edge to control the drive current of the stepping motor 39.

Therefore, according to the present fifth embodiment, by setting in optimum the duty ratio $DT_{ai}$, $DT_{bi}$ stored in the table of the RAM 43 according to the change of the required torque, the consumption current can be reduced by reducing the drive current according to the required torque before the stepping motor 39 makes one turn when the power is turned on. The above-mentioned arrangement can allow the power battery to be compacted.

Furthermore, by setting the duty ratio $DT_{ai}$, $DT_{bi}$ every one pulse P of the motor delve pulse signal, the drive current of the stepping motor 39 can be controlled every one pulse P, which allows the consumption current to be further reduced.

Furthermore, by making the step S111 through step S127 of the flowchart shown in FIG. 15 similar to the step S21 through step S37 of the flowchart shown in FIG. 10, the rotational position of the motor can be detected by time.

Sixth embodiment

Then the following describes a sixth embodiment related to the motor driving torque controlling operation.

In the present sixth embodiment, a combination $(a_i, b_i)$ of the slit length $a_i$ and the slit interval $b_i$ is stored in the table of the RAM 43 in the same arrangement as in each of the aforementioned embodiments. Meanwhile, the duty ratio $(DT_{ai}, DT_{bi})$ of the pulses P of the motor drive pulse signal is stored in a table different from that of $(a_i, b_i)$ of the RAM 43 in correspondence with $(a_i, b_i)$ in the same manner as in the fifth embodiment. It is to be noted that the set values of the duty ratio are expressed in terms of percentage (%).

Practical values of $(a_i, b_i)$ and $(DT_{ai}, DT_{bi})$ are described on the fifth embodiment.

Furthermore, the RAM 43 stores for every edge a cumulative pulse amount CO[N1] representing a cumulative value of the pulses P supplied to the stepping motor 39 while the slit disk 45 rotates from the position of the first edge to the position of each edge in a table different from the tables storing the values of $(a_i, b_i)$ and $(DT_{ai}, DT_{bi})$. Meanwhile, a stationary duty ratio DH[N1] representing a duty ratio of the pulses P required for securing the stationary torque of the stepping motor 39 is stored in correspondence with $(a_i, b_i)$.

It is to be noted that the duty ratio of the pulses P required for driving the stepping motor 39 which is initialized in step S142 is referred to as a drive duty ratio in contrast to the stationary duty ratio.

By controlling the duty ratio of the pulses P of the motor drive pulse signal as shown in FIG. 6D based on $(DT_{ai}, DT_{bi})$ by means of the 20 kHz duty ratio control section 40, the drive current of the stepping motor 39 can be controlled.

Figure 17:
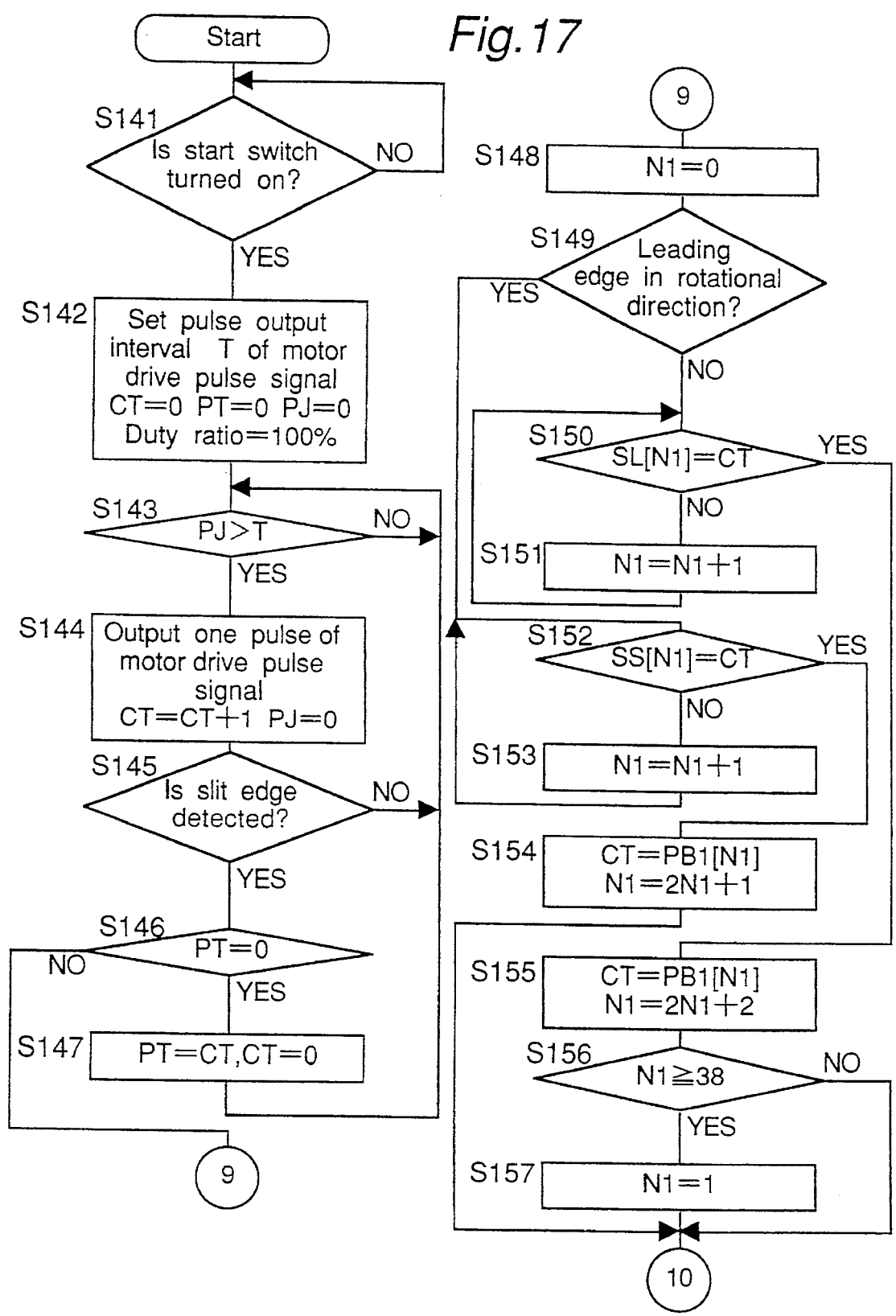
FIG. 17 is a flowchart of a motor driving torque controlling operation of the fluid infusion pump different from the flowchart of FIG. 15.
Figure 18:
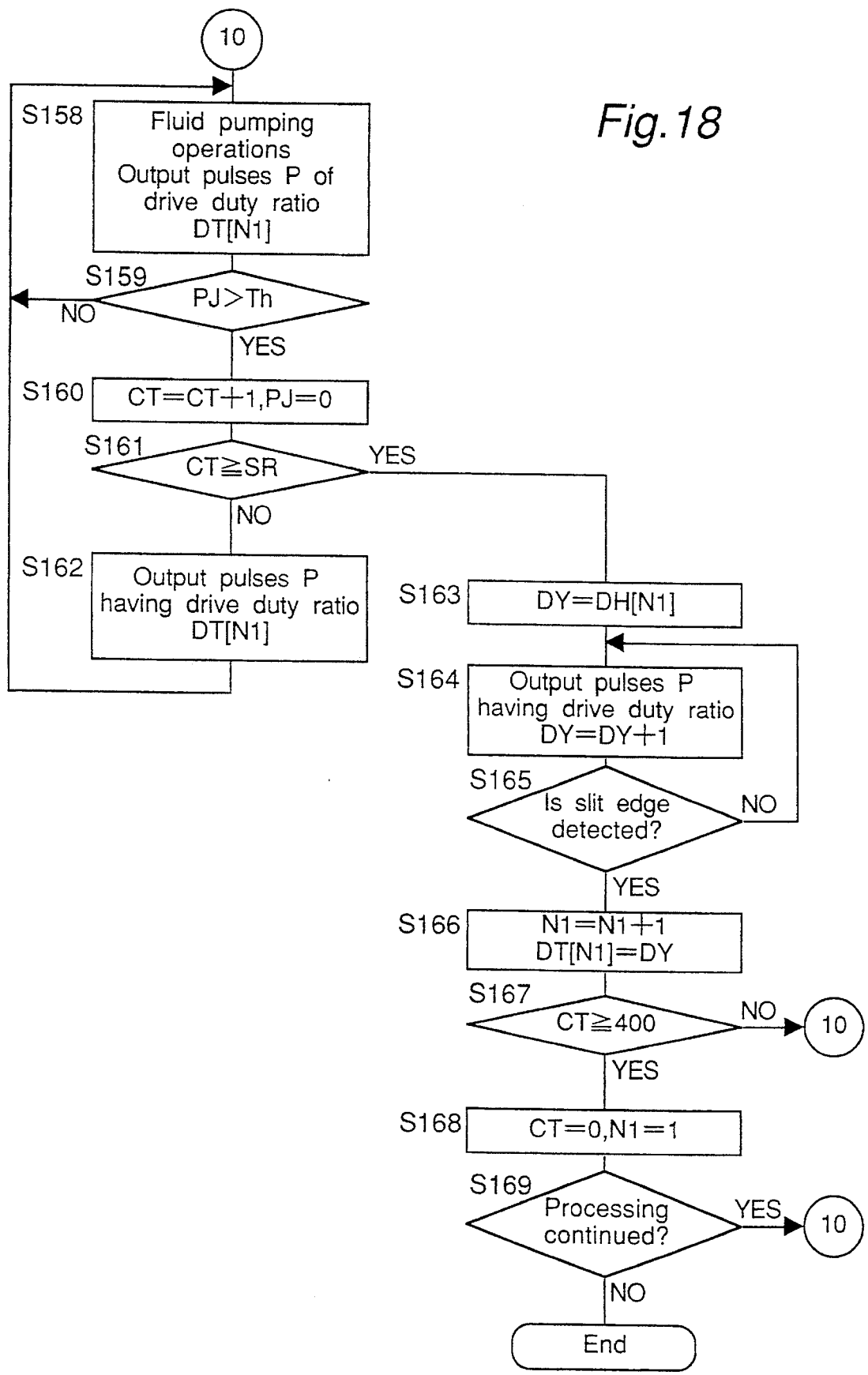
FIG. 18 is a flowchart of the motor driving torque controlling operation continued from the flowchart of FIG. 17.

FIGS. 17 and 18 are flowcharts of the motor driving torque controlling operation executed under the control of the CPU 31.

In step S141 through step S157, setting of the pulse output interval time T based on the set flow rate Y (ml/hr) and initialization of the duty ratio of the pulses P (100%) are executed in the same manner as in step S111 through step S127 of the driving torque controlling operation of the fifth embodiment. Then the stepping motor 39 is driven, and specifying of the edge detected in the second edge detecting stage, setting of the address N1 in which the duty ratio $DT_{ai}$ corresponding to the slit length $a_i$ or the duty ratio $DT_{bi}$ corresponding to the slit interval $b_i$ is stored, and setting of the amount of pulses PB1[N1] in the interval from the first edge to the concerned edge in the count value CT are executed.

The rotational position of the stepping motor 39 is detected through the aforementioned steps. Subsequently, the program flow enters into a motor driving torque controlling process based on the detected rotational position of the stepping motor 39.

In step S158, the aforementioned fluid pumping operations are started, the duty ratio DT[N1] read based on the address number N1 set in step S154 or step S155 is transferred to the 20 kHz duty ratio control section 40, and one pulse of the pulses P having the drive duty ratio DT[N1] is supplied to the stepping motor 39. Then the cumulative pulse amount CO[N1] is read from the corresponding table of the RAM 43 based on the address N1, and set in a set pulse amount SR.

In step S159, it is decided whether or not the after-pulse-application elapsed time PJ is longer than the pulse output interval time T. Consequently, when the time PJ is longer than the interval T, the program flow proceeds to step S160. Otherwise, the program flow returns to step S158 to continue the fluid pumping operations.

In step S160, the content of the count value CT is incremented, and the after-pulse-application elapsed time PJ is reset.

In step S161, it is decided whether or not the content of the count value CT exceeds the set pulse amount SR. Consequently, when the count value CT exceeds the set pulse amount SR (i.e., when the N1th edge has reached the position of the photosensor 37), the program flow proceeds to step S163. Otherwise, the program flow proceeds to step S162.

In step S162, one pulse of the pulses P of the duty ratio DT[N1] set in step S158 is outputted, and the program flow returns to step S158.

In other words, through the step S158 through step S162, the stepping motor B9 is made to rotate to a position where the N1th edge will reach the position of the photosensor 37 when one more pulse of the pulses P is outputted.

In step S163, the stationary duty ratio DH[N1] stored in the corresponding table of the RAM 43 is read based on the address number N1 and then set in a set duty ratio DY.

In step S164, the content of the set duty ratio DY is incremented. Then one pulse of the pulses P such that the set duty ratio DY is used as the drive duty ratio is outputted before the after-pulse-application elapsed time PJ reaches the pulse output interval time T.

In step S165, it is decided whether or not the edge of the slit 45a of the slit disk 45 is detected by the photosensor 37. Consequently, when an edge is detected, the program flow proceeds to step S166. Otherwise, the program flow returns to step S164, and the pulses P having the incremented set duty ratio DY is outputted.

Thus by gradually increasing the set duty ratio DY, the possible stepout condition is eliminated at the point of time when the minimum current required for obtaining the driving torque flows through the stepping motor 39, and the stepping motor 39 starts to rotate. Then by detecting the edge in a manner as described above, the fact that the stepping motor 39 has escaped from the stepout condition and starts to rotate is detected.

In step S166, since the edge of the slit 45a has been detected, the address number N1 is incremented. Thereafter, it is determined that the set duty ratio DY (i.e., the duty ratio at which the minimum current required for obtaining the driving torque is achieved) is the drive duty ratio for the concerned edge, and the set duty ratio DY is set in the drive duty ratio DT[N1].

In step S167, it is decided whether or not the content of the count value CT is not smaller than a value of 400. Consequently, when the content is not smaller than the value of 400, the program flow proceeds to step S168. Otherwise, the program flow returns to step S158 to execute the optimization of the drive duty ratio relevant to the next edge.

In step S168, since the stepping motor 39 has made one turn, the content of the count value CT is cleared to "0", and the first address "1" is set in the address number N1.

In step S169, it is decided whether or not the motor driving torque controlling operation is to be continued. Consequently, when the above-mentioned operation is continued, the program flow returns to step S158 to execute the optimization of the drive duty ratio relevant to the next edge. Otherwise, the motor driving torque controlling operation is completed.

In other words, in the present sixth embodiment, the motor initial driving means is comprised of the step S158 through step S162, the duty ratio setting means is comprised of the step S163 through step S165, and the motor driving means is comprised of the step S158 through step S162.

In the present sixth embodiment as described above, the rotational position of the stepping motor 39 is detected at the second edge after the stepping motor 39 has started. Subsequently, every time an edge is detected, the drive duty ratio at which the minimum current required for the driving torque of the stepping motor B9 is achieved is determined based on the duty ratio $DT_{ai}$, $DT_{bi}$ of the concerned edge to control in optimum the driving torque of the stepping motor 39.

Therefore, according to the present sixth embodiment, the drive current of the stepping motor 39 can be reduced without waiting for the completion of one turn of the stepping motor 39 to allow the power battery to be compacted while reducing the consumption current particularly at a low flow rate.

For instance, when the rotating speed of the stepping motor B9 is set so that each cam 19 makes one turn to achieve fluid transfer at a flow rate of 0.1 ml/hr in 400 pulses P of the motor drive pulse signal, the pulse output interval time T is nine seconds. Therefore, when the stepping motor B9 steps out while several pulses P are outputted, the fluid transfer is possibly stopped for several minutes.

However, according to the present sixth embodiment, an increment of 20 steps per second can be achieved even when the set duty ratio DY is incremented once per 50 msec in step S164, with which the drive duty ratio can be optimized in a very short time in comparison with the conventional case.

Although the set duty ratio DY which presents the minimum current required for obtaining the driving torque set in step S164 and step S165 is directly used as the drive duty ratio in step S166 of the aforementioned flowchart, a duty ratio obtained by adding a specified value to the set duty ratio DY may be used as the drive duty ratio to allow the driving torque to have a margin.

Furthermore, by making the step S141 through step S157 of the flowchart shown in FIG. 17 similar to the step S21 through step S37 of the flowchart shown in FIG. 10, the rotational position of the motor can be detected by time.

Furthermore, according to the present sixth embodiment, the drive duty ratio is optimized every time the edge of each slit 45a is detected, and therefore the conventionally used slit disk in which the slit length $a_i$ and the slit interval $b_i$ are identical can be utilized.

Seventh embodiment

Then the following describes a seventh embodiment related to a stationary torque controlling operation in driving the motor.

In the present seventh embodiment, a combination $(a_i, b_i)$ of the slit length $a_i$ and the slit interval $b_i$ is stored in the table of the RAM 43 as arranged in the same manner as in each of the aforementioned embodiments. The duty ratio of the pulses P of the motor drive pulse signal is stored in correspondence with $(a_i, b_i)$ in the same manner as in the fifth embodiment and the sixth embodiment in a table different from that of $(a_i, b_i)$ in the RAM 43. It is to be noted that set values of the duty ratio are denoted in terms of percentage (%).

Figure 19:
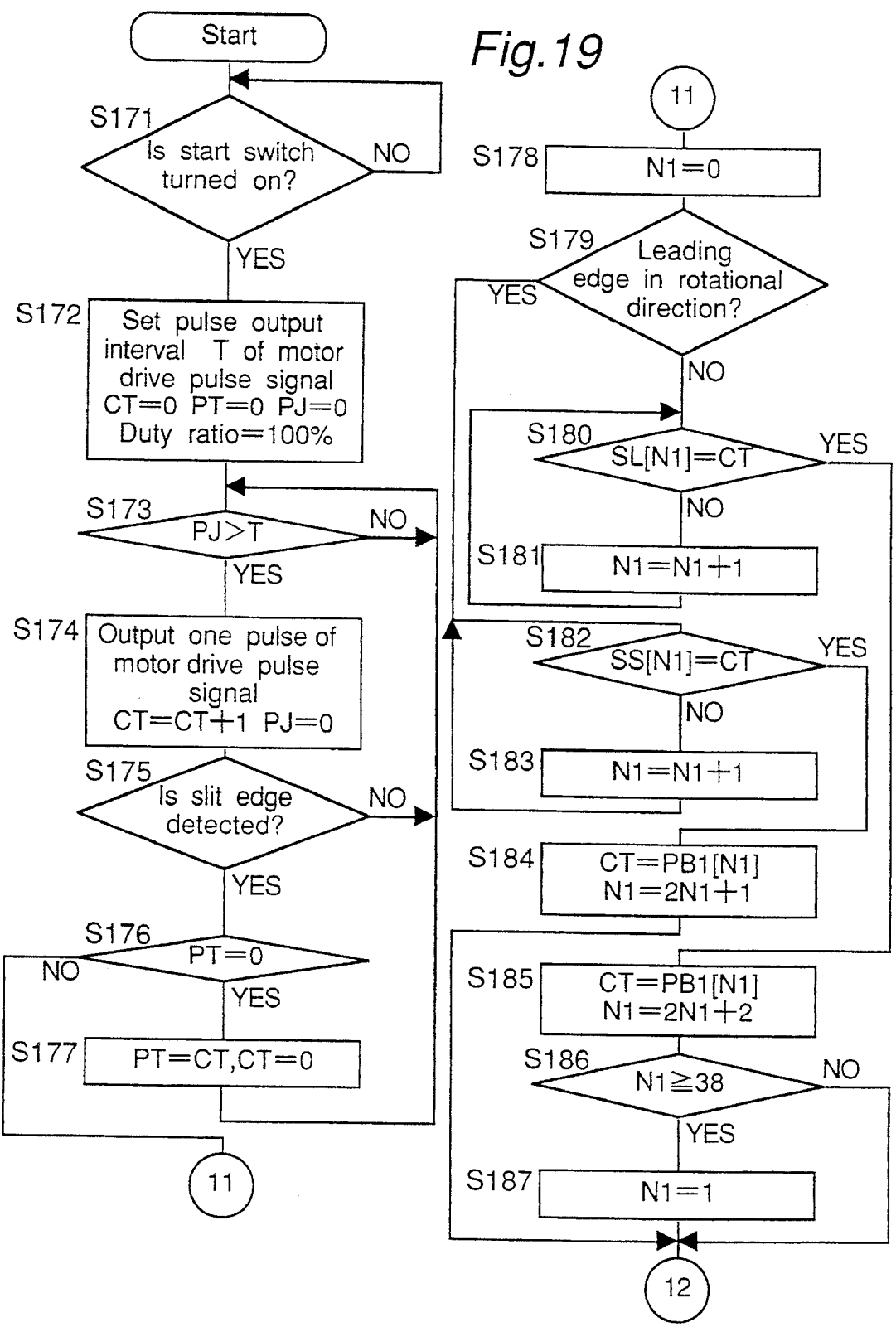
FIG. 19 is a flowchart of a stationary torque controlling operation in driving the motor of the fluid infusion pump.
Figure 20:
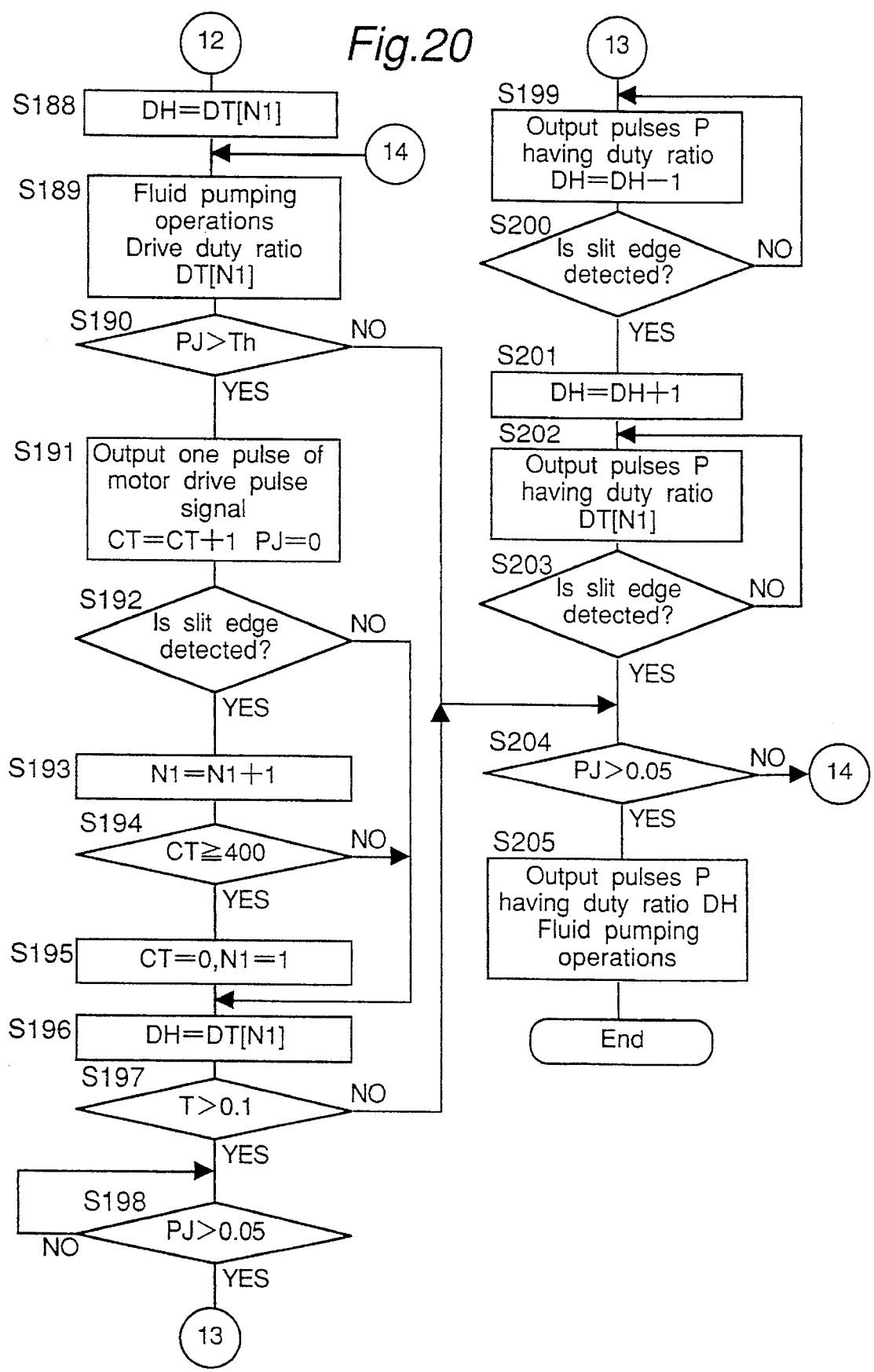
FIG. 20 is a flowchart of the stationary torque controlling operation in driving the motor continued from the flowchart of FIG. 19.

FIGS. 19 and 20 are flowcharts of the stationary torque controlling operation executed under the control of the CPU 31 when the motor starts to be driven.

In step S171 through step S187, setting of the pulse output interval time T, initialization of the duty ratio (100%), specifying of the edge detected in the second time, setting of the address N1 of the duty ratio $DT_{ai}$, $DT_{bi}$ of the concerned edge, and setting of the amount of pulses PB1[N1] in the interval from the first edge to the concerned edge are executed in the same manner as in step S111 through step S127 of the driving torque controlling operation of the fifth embodiment or step S141 through step S157 of the driving torque controlling operation of the sixth embodiment.

The rotational position of the stepping motor 39 is detected through the aforementioned steps. Subsequently, the program flow enters into a stationary torque controlling process in starting driving the motor based on the detected rotational position of the stepping motor 39.

In step S188, the value DT[N1] of the duty ratio $DT_{ai}$ or the duty ratio $DT_{bi}$ stored in the corresponding table of the RAM 43 is read based on the address number N1 calculated in step S184 or step S185, and set in a stationary duty ratio DH.

In step S189, the aforementioned fluid pumping operations are started, and the duty ratio DT[N1] read in step S188 is transferred to the 20 kHz duty ratio control section 40, and the initial value of the drive duty ratio is set in the duty ratio DT[N1].

In step S190, it is decided whether or not the after-pulse-application elapsed time PJ is longer than the pulse output interval time T. Consequently, when the time PJ is longer than the interval T, the program flow proceeds to step S191. Otherwise, the program flow proceeds to step S204.

In step S191, one pulse of the pulses P of the motor drive pulse signal is supplied to the stepping motor 39.

Thereafter, the content of the count value CT is incremented, and the after-pulse-application elapsed time PJ is reset.

In step S192, it is decided whether or not the edge of the slit 45a is detected by the photosensor 37. Consequently, when an edge is detected, the program flow proceeds to step S193. Otherwise, the program flow proceeds to step S196.

In step S193, the content of the address number N1 is incremented.

In step S194, it is decided whether or not the content of the count value CT is not smaller than a value of 400. Consequently, when the content is not smaller than the value of 400, the program flow proceeds to step S195. Otherwise, the step S195 is skipped.

In step S195, since the stepping motor 39 has made one turn, the content of the content value CT is cleared to "0", and the first address "1" is set in the address number N1.

In step S196, the drive duty ratio DT[N1] set in step S189 or the duty ratio DT[N1] based on the address number N1 set in step S195 is see as a temporary value of the stationary duty ratio DH.

In step S197, it is decided whether or not the pulse output interval time T see in step S172 is longer than 0.1 sec. Consequently, when the interval T is longer than 0.1 sec, the program flow proceeds to step S198. Otherwise, the program flow proceeds to step S204.

In the above case, according to the present seventh embodiment, the drive current is reduced when the fluid transfer speed is slow. Therefore, when the pulse output interval time T is toe greater than 0.1 sec and the fluid transfer speed is fast, the step S198 through step S203 are skipped to execute no optimization of the stationary duty ratio.

In step S198, when the operation of the stepping motor 39 is stabilized when the after-pulse-application elapsed time PJ reaches 0.05 sec, the program flow proceeds to step S199.

In step S199, the content of the stationary duty ratio DH is decremented, and the pulse P of the stationary duty ratio DH is supplied to the stepping motor 39.

In step S200, it is decided whether or not the edge of the slit 45a is detected. Consequently, when the edge is detected, the program flow proceeds to step S201. Otherwise, the program flow returns to step S199 to further decrement the stationary duty ratio In the above case, when the stationary duty ratio DH is reduced too much, the stepping motor 39 starts to rotate reversely. Therefore, the reverse rotation of the stepping motor 39 is detected in the aforementioned edge detecting operation.

In step S201, the stationary duty ratio DH is incremented to allow the minimum torque to be secured when the pulse P having the stationary duty ratio DH is supplied to the stepping motor 39.

In the above case, it is acceptable to provide a margin in the stationary torque by adding "2" to the stationary duty ratio DH taking into account the possible variation of the fluid pumping section 11.

In step S202, before the after-pulse-application elapsed time PJ reaches the pulse output interval time T, one pulse of the pulses P having the drive duty ratio DT[N1] is supplied to the stepping motor 39. Thus the possible generation of an error in the fluid transfer speed due to the reverse rotation of the stepping motor 39 is prevented.

In step S203, it is decided whether or not the edge of the slit 45a is detected by the photosensor 37 and the forward rotation of the stepping motor 39 is confirmed. Consequently, when the edge is detected, the program flow proceeds to step S204. Otherwise, the program flow returns to step S202, and one pulse of the pulses P having the drive duty ratio DT[N1] is supplied.

The optimization of the stationary duty ratio is completed through the aforementioned steps.

In step S204, when the after-pulse-application elapsed time PJ reaches 0.05 sec and the operation of the stepping motor 39 is stabilized, the program flow proceeds to step S205. Otherwise, the program flow returns to step S189 to supply the pulse P having the drive duty ratio to the stepping motor 39.

In step S205 one pulse of the pulses P having the stationary duty ratio DH is supplied to the stepping motor 39 to drive the stepping motor 39, with which the aforementioned fluid pumping operations are executed. Thereafter, the stationary torque controlling operation in the time when the motor is driven is completed.

In other words, according to the present seventh embodiment, the reversing start duty ratio setting means is comprised of the step S199 and step S200, the duty ratio setting means is comprised of the step S201 through step S203, and the motor driving means is comprised of the step S205.

In the present seventh embodiment as described above, the rotational position of the stepping motor 39 is detected at the second edge after the stepping motor 39 has started, and the stationary duty ratio supplied to the stepping motor B9 in the concerned rotational position is optimized based on the duty ratio $DT_{ai}$, $DT_{bi}$ of the concerned edge to thereby control the drive current in stating to drive the stepping motor 39.

Therefore, according to the present seventh embodiment, the drive current of the stepping motor 39 can be reduced without waiting for the completion of one turn of the stepping motor 39, and the consumption current can be reduced to allow the power battery to be compacted.

By optimizing the drive duty ratio according to the sixth embodiment after the stepping motor 39 is made to rotate with the drive current securing the minimum driving torque required in the driving start stage according to the present seventh embodiment, the stepping motor 39 can be continuously driven with the minimum drive current.

Furthermore, by making the step S171 through step S187 of the flowchart shown in FIG. 19 similar to the step S21 through S37 of the flowchart shown in FIG. 10, the rotational position of the motor can be detected by time.

Furthermore, according to the aforementioned seventh embodiment, the stationary duty ratio is optimized every time the edge of each slit 45a is detected, and therefore the conventionally used slit disk in which the slit length $a_i$ and the slit interval $b_i$ are identical can be utilized.

Eighth embodiment

A fluid infusion pump of the eighth embodiment has a structure obtained by removing the encoder 47 from the shaft 18 of the fluid pumping section 11 shown in FIG. 7 of the aforementioned fluid infusion pump, and the control system thereof is obtained by removing the photosensor 37 from the structure of the block diagram shown in FIG. 5.

The motor rotational position detection of the present embodiment is executed based on a detection signal from the pressure sensor 16 not resorting to the encoder.

Figure 21:
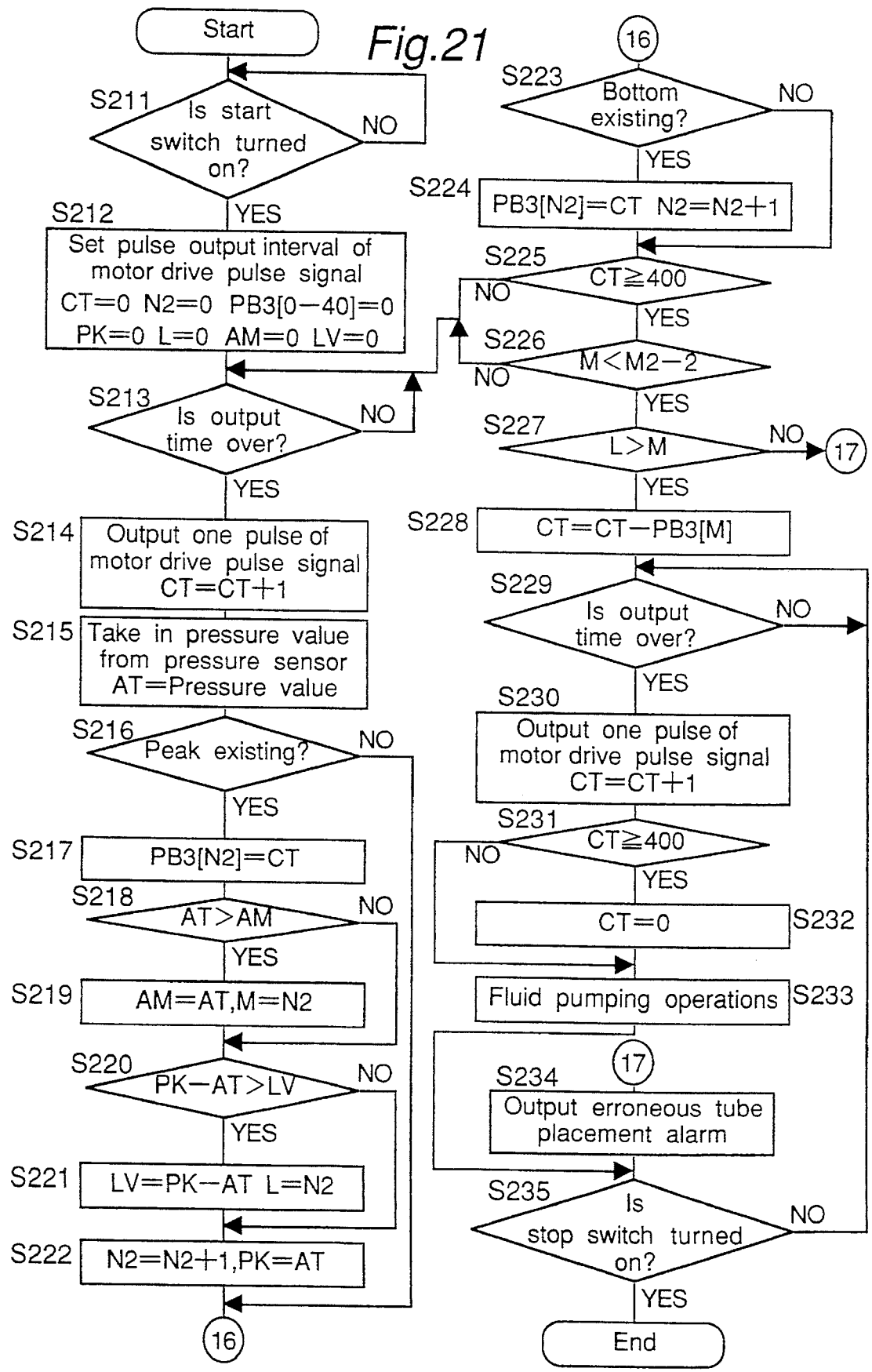
FIG. 21 is a flowchart of a motor rotational position detecting operation of the fluid infusion pump.

FIG. 21 is a flowchart of a rotational position detecting operation executed under the control of the CPU 31. The following describes in detail the rotational position detecting operation with reference to FIG. 21.

In step S211, it is decided whether or not the start switch is turned on. When the start switch is turned on, the program flow proceeds to step S212.

In step S212, the pulse output interval time of the motor drive pulse signal is set in the same manner as in step S2 of the rotational position detecting operation of the first embodiment.

Furthermore, the contents of the count value CT, address number N2, pulse cumulation value PB3[N2=0–40], previously sampled peak value PK, address L of the pulse cumulation value when the peak level change takes its maximum value, maximum peak value AM, and peak level maximum variance value LV stored in the RAM 43 are each initialized to "0".

In step S213, it is decided whether or not the output time exceeds a specified time. Consequently, when the output time exceeds the specified time, the program flow proceeds to step S214.

In step S214, one pulse of the pulses P of the motor drive pulse signal is supplied from the motor driver 38 to the stepping motor 39, and the count value CT of the amount of pulses is incremented.

In step S215, the pressure value from the pressure sensor 16 is taken in and see in the pressure value AT.

In step S216, it is decided whether or not a peak exists in the pressure waveform in the vicinity of the concerned rotational position based on the pressure value AT set in step S215. Consequently, when a peak exists, the program flow proceeds to step S217. Otherwise, the program flow proceeds to step S223 to enter into an operation of checking a portion in the vicinity of the bottom.

In step S217, the count value CT is set in the pulse cumulation value PB3[N2] stored in the address N2 of the corresponding table in the RAM 43.

In step S218, it is decided whether or not the pressure value AT taken in in step S215 is greater than the maximum peak pressure value AM. Consequently, when the pressure value AT is greater than the maximum peak pressure value AM, the program flow proceeds to step S219. Otherwise, the step S219 is skipped.

In step S219, the content off the maximum peak pressure value AM is replaced by the pressure value AT, and the present address number N2 is see in the address number M in which the pulse cumulation value in the above-mentioned time is stored.

In step S220, a difference between the previously sampled peak value PK and the pressure value (peak value) AT sampled in the present time is calculated, and it is decided whether or not the calculated value is greater than the peak level maximum variance value LV. Consequently, when the calculated value is greater than the value LV, the program flow proceeds to step S221. Otherwise, the step S221 is skipped.

In step S221, the content of the peak level maximum variance value LV is replaced by a value (PK–AT), and the present address number N2 is set in the address number L in which the pulse cumulation value in the above-mentioned time is stored.

In step S222, the address number N2 is incremented, and the content of the previously sampled peak value PK is replaced by the pressure value (peak value) AT sampled in the present time.

In step S223, it is decided whether or not a bottom exists in the pressure waveform in the vicinity of the concerned rotational position based on the pressure value AT set in step S215. Consequently, when a bottom exists, the program flow proceeds to step S224. Otherwise, the step S224 is skipped.

In step S224, the count value CT is set in the pulse cumulation value PB3[N2] stored in the address N2 of the corresponding table in the RAM 43, and the address number N2 is incremented.

In step S225, it is decided whether or not the content of the count value CT is not smaller than a value of 400. Consequently, when the content is not smaller than the value of 400, meaning that the stepping motor 39 has already made one turn, the program flow proceeds to step S226. Otherwise, the stepping motor 39 has not yet made one turn and there is the possibility that another maximum peak value may appear subsequently, and therefore the program flow returns to step S213 to continue searching the maximum peak value.

In step S226, it is decided whether or not the address number M which is storing the pulse cumulation value PB3[M] in the time when the maximum peak value AM appears is smaller than a value of (N2–2) to check whether or not two or more peaks or bottoms have been detected after the maximum peak value AM had been detected. Consequently, when the address number M is smaller than the value of (N2–2) and two or more peaks or bottoms have been detected after the maximum peak value AM had been detected, the program flow proceeds to step S227. When the address number M is not smaller than the value of (N2–2) and two or more peaks or bottoms have not yet been detected after the maximum peak value AM had been detected, there is the possibility that a peak level maximum variance value may be detected in the next peak. Therefore, the program flow returns to step S213 to continue detecting the peak level maximum variance value.

In step S227, it is decided whether or not the address number L which is storing a pulse cumulation value PB3[L] in the time when the maximum value LV of the variance of the peak level is detected is greater than the address number M which is storing the pulse cumulation value PB3[M] in the time when the maximum peak value AM is detected. In other words, it is decided whether or not the timing at which the maximum value LV of the variance of the peak level is detected is subsequent to the timing at which the maximum peak value AM is detected.

In the present case, the maximum value of the variance of the peak level is to appear subsequent to the appearance of the maximum peak value as shown in FIG. 3A. Therefore, when the above-mentioned decision produces a result of greatness (i.e., subsequence), the program flow proceeds to step S228. When the decision produces a result of smallness (i.e., precedence), the program flow proceeds to step S234.

In step S228, the pulse cumulation value PB3[M] in the time when the maximum peak value AM is detected is subtracted from the count value CT to calculate the amount of pulses in the present time with respect to the reference point of the time when the maximum peak value AM is detected.

Thus the rotational position of the motor in the present time with respect to the reference point of the time when the maximum peak value AM is detected (i.e., the position of the finger 20 that is pressing the tube 23) is represented by the amount of pulses of the motor drive pulse signal.

In step S229, it is decided whether or not the output time exceeds a specified time. Consequently, when the output time exceeds a specified time, the program flow proceeds to step S230.

In step S230, one pulse of the pulses P of the motor drive pulse signal is supplied from the motor driver 38 to the stepping motor 39, and the count value CT is incremented.

In step S231, it is decided whether or not the content of the count value CT is not smaller than a value of 400. Consequently, when the content is non smaller than the value of 400, the program flow proceeds to step S232. Otherwise, the step S232 is skipped.

In step S232, since the stepping motor 39 has made one turn, the content of the count value CT is cleared.

In step S233, the aforementioned fluid pumping operations are executed. Thereafter, the program flow proceeds to step S235.

In step S234, it is decided that the timing at which the peak level maximum variance value LV is detected is preceding the timing at which the maximum peak value AM is detected in step S227, and therefore it is decided that the maximum peak value is possibly reduced below a predetermined value due to an erroneous placement of the tube 23. Then an erroneous tube placement alarm is outputted to the I/O driver 34 to make the buzzer 36 issue an alarm sound.

In step S235, it is decided whether or not a stop switch is turned on. Consequently, when the stop switch is not turned on, the program flow returns to step S229, and one pulse of the pulses P of the motor drive pulse signal is outputted. When the stop switch is turned on, the rotational position detecting operation is completed.

In step S225 of the present eighth embodiment, the amount of pulses in the present time is calculated with the point of time when the maximum peak value AM is detected used as a reference by subtracting from the count value CT the pulse cumulation value PB3[M] in the time when the maximum peak value AM is detected. However, the amount of pulses in the present time may be calculated with the point of time when the peak level maximum variance value LV is detected used as a reference by subtracting from the count value CT the pulse cumulation value PB3[L] in the time when the peak level maximum variance value LV is detected.

According to the present eighth embodiment as described above, when the tube is correctly placed, the change of pressure from the pressure sensor 16 responds to the pressure from each of the fingers 20 in a manner as shown in FIG. 3A to produce nine peaks, and the peaks have increasing peak levels sequentially from the #2 finger $20_2$ to the #10 finger $20_{10}$ as a whole. In view of the above-mentioned fact, the point of time when the maximum peak value appears (the point of time when the pressures from the #1 finger $20_1$ and the #10 finger $20_{10}$ are applied) or the point of time when the peak level maximum variance value appears (the point of time when the pressure applying finger changes from the #1 finger $20_1$ to the #2 finger $20_2$) is used as the reference point. Then, according to the amount of pulses of the motor drive pulse signal from the reference point, the rotational position of the motor is detected.

Therefore, according to the present eighth embodiment, the rotational position of the motor can be easily detected without using any encoder having a great volume, which allows a cost reduction and the compacting of the fluid infusion pump to be achieved.

Ninth embodiment

Then the following describes a ninth embodiment related to a downstream occlusion detecting operation.

Figure 22:
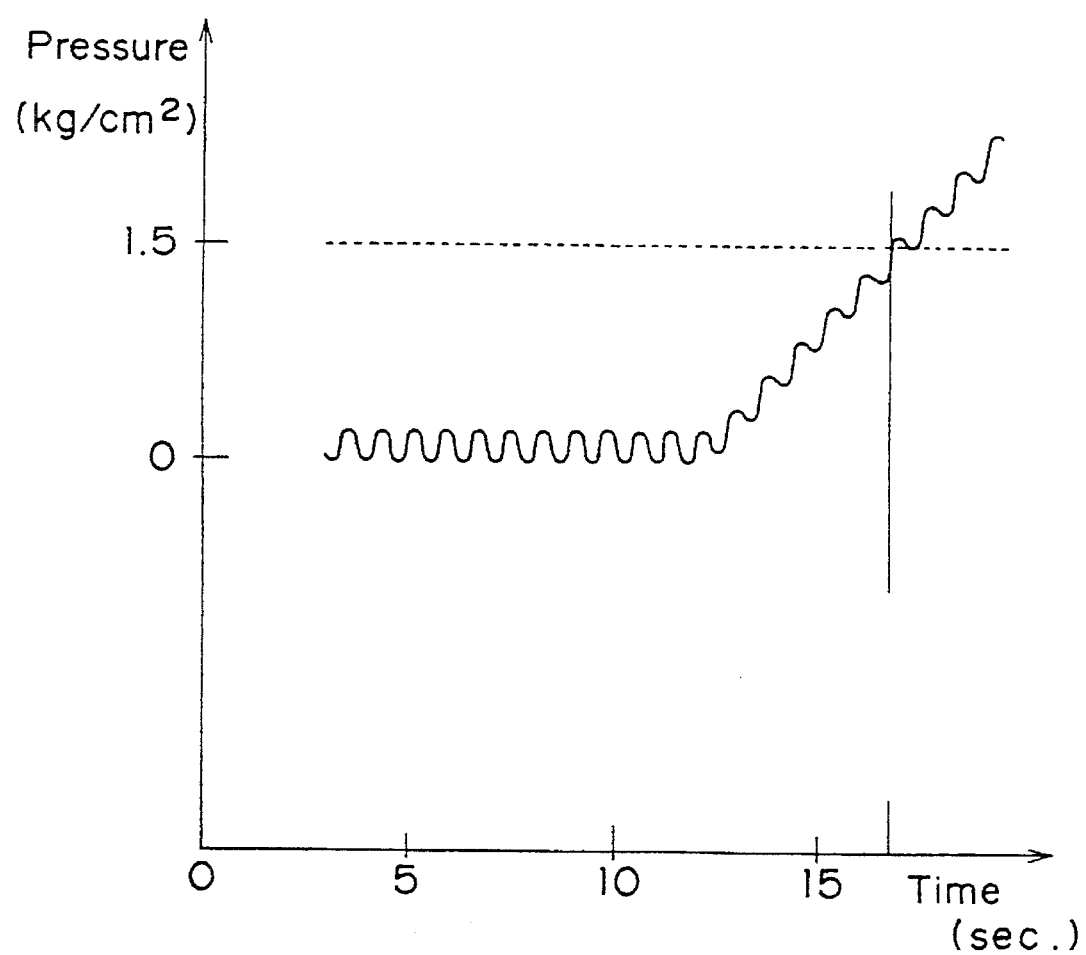
FIG. 22 is a graph showing an exemplified pressure increase detected by the pressure sensor in the case of downstream occlusion.

The downstream occlusion detection of the present ninth embodiment is executed based on the change of pressure from the pressure sensor 16 of the eighth embodiment. In detail, when the tube 23 is occluded on the downstream side, the pressure inside the tube increases. Therefore, in a manner as shown in FIG. 22, the pressure value detected by the pressure sensor 16 also increases. Therefore, by observing such a phenomenon that the pressure value from the pressure sensor 16 exceeds a specified value, the downstream occlusion is detected.

Figure 23:
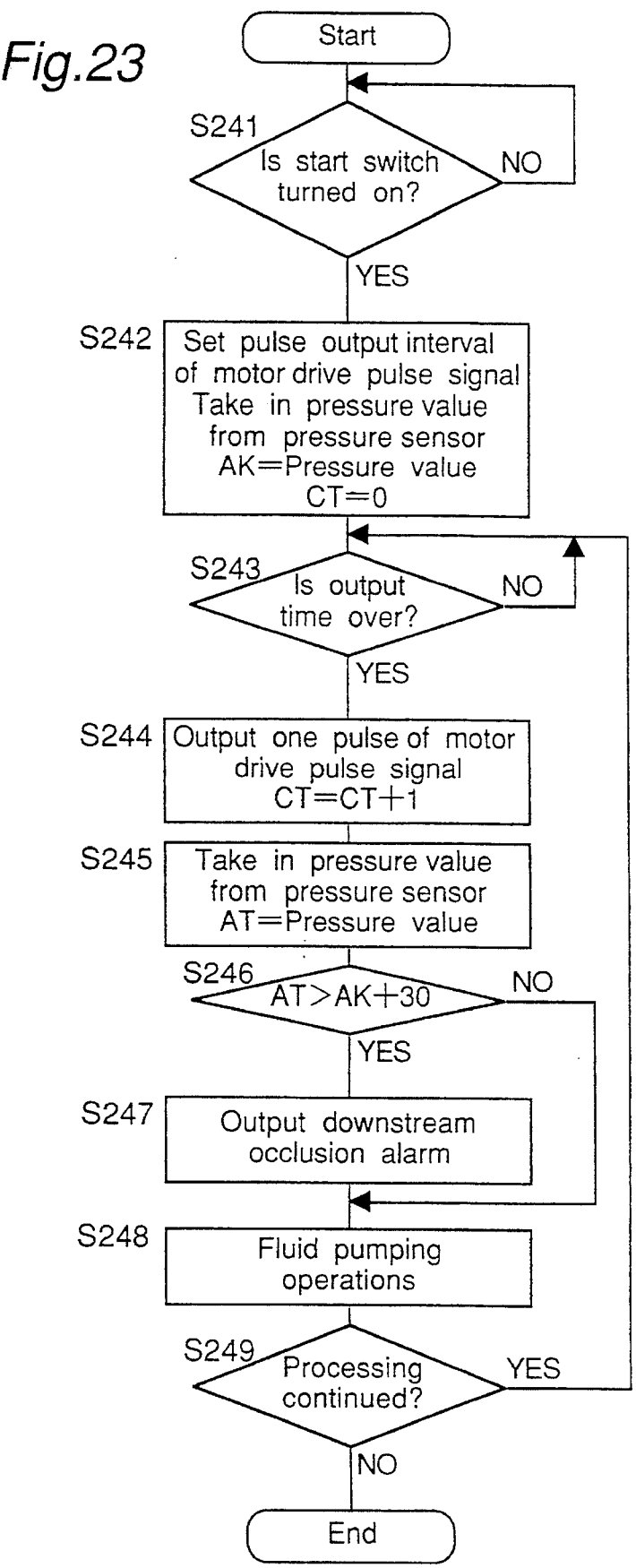
FIG. 23 is a flowchart of a downstream occlusion detecting operation of the fluid infusion pump.

FIG. 23 is a flowchart of a downstream occlusion detecting operation executed under the control of the CPU 31. The following describes in detail the downstream occlusion detecting operation with reference to FIG. 23.

In step S241, it is decided whether or not the start switch is turned on. When the start switch is turned on, the program flow proceeds to step S242.

In step S242, the pulse output interval time of the motor drive pulse signal is set according to a set flow rate.

Then the content of the count value CT stored in the RAM 43 is initialized to "0". Then, the pressure value from the pressure sensor 16 is taken in and set in the initial pressure value AK.

In step S243, it is decided whether or not the output time exceeds a specified time. Consequently, when the output time exceeds the specified time, the program flow proceeds to step S244.

In step S244, one pulse of the pulses P of the motor drive pulse signal is supplied from the motor driver 38 to the stepping motor 39, and the count value CT is incremented.

In step S245, the pressure value from the pressure sensor 16 is taken in and set in the pressure value AT.

In step S246, it is decided whether or not the present pressure value AT taken in from the pressure sensor 16 in step S245 is greater than a value obtained by adding a value of "30" to the initial pressure value AK. Consequently, when the value AT is greater than the obtained value, the program flow proceeds to step S247. Otherwise, the step S247 is skipped.

In the present ninth embodiment, the value from the pressure sensor 16 is subjected to an analog-to-digital conversion in eight bits in an analog-to-digital converter of the I/O driver 34, where the converted digital value "1" corresponds to 0.05 kg/cm$^2$. Since the pressure inside the tube increases when the downstream occlusion occurs, it is decided that the downstream occlusion has occurred when the present pressure value AK becomes greater than the initial pressure value AK by a value more than 1.5 kg/cm$^2$ ("30" in digital value).

In step S247, it is decided that the downstream occlusion has occurred, and the downstream occlusion alarm is outputted to the I/O driver 34 to make the buzzer 36 issue an alarm sound.

In step S248, the aforementioned fluid pumping operations are executed.

In step S249, it is decided whether or not the downstream occlusion detecting operation is to be continued. Consequently, when the above-mentioned operation is continued, the program flow returns to step S243 to take in the next pressure value AT. Otherwise, the downstream occlusion detecting operation is completed.

In other words, according to the present ninth embodiment, the downstream occlusion deciding means is comprised of the step S245 through step S247.

According to the present ninth embodiment as described above, the downstream occlusion detection can be also executed by the pressure sensor 16 which is provided in opposition to the fluid pumping section 11 in the cover 15 and used in detecting the erroneous placement of the tube 23. Therefore, the present ninth embodiment obviates the need of providing any pressure sensor specially for detecting the downstream occlusion on the downstream side of the fluid pumping section 11 or in the middle portion of the fluid pumping section 11 independently of the pressure sensor 16, which allows the fluid infusion pump to be easily compacted.

Tenth embodiment

Then the following describes a tenth embodiment related to an upstream occlusion detecting operation.

Figure 24A:
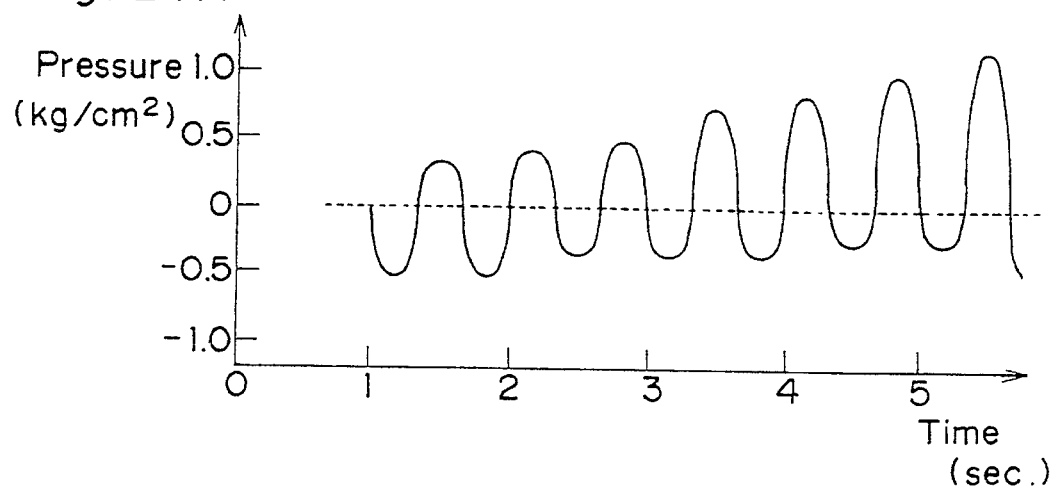
FIGS. 24A and 24B are graphs showing an exemplified pressure reduction of the bottom level detected by the pressure sensor in the case of upstream occlusion.
Figure 24B:
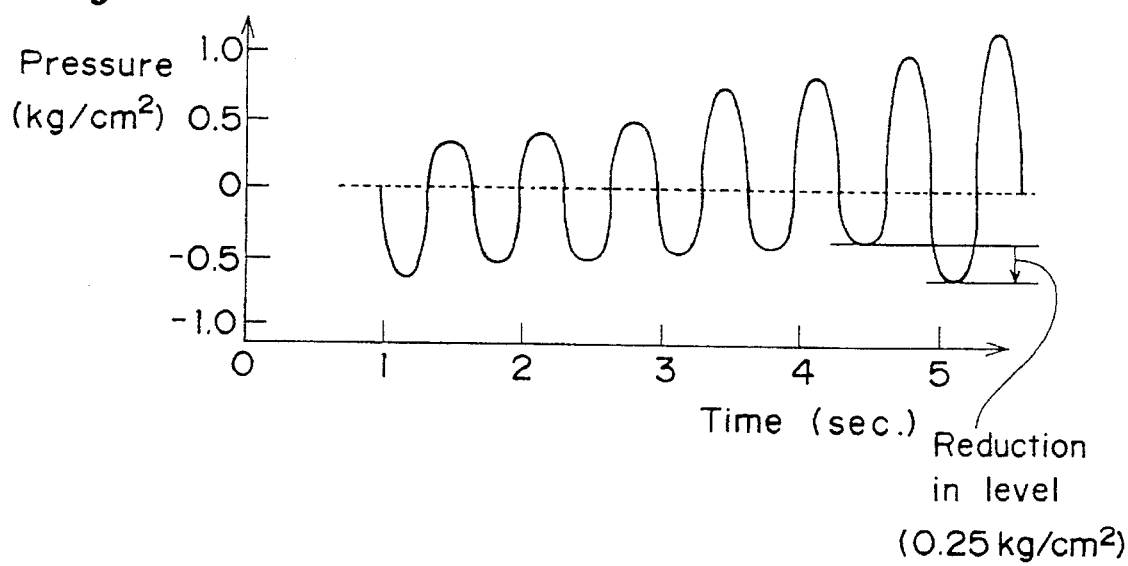
Figure 27:
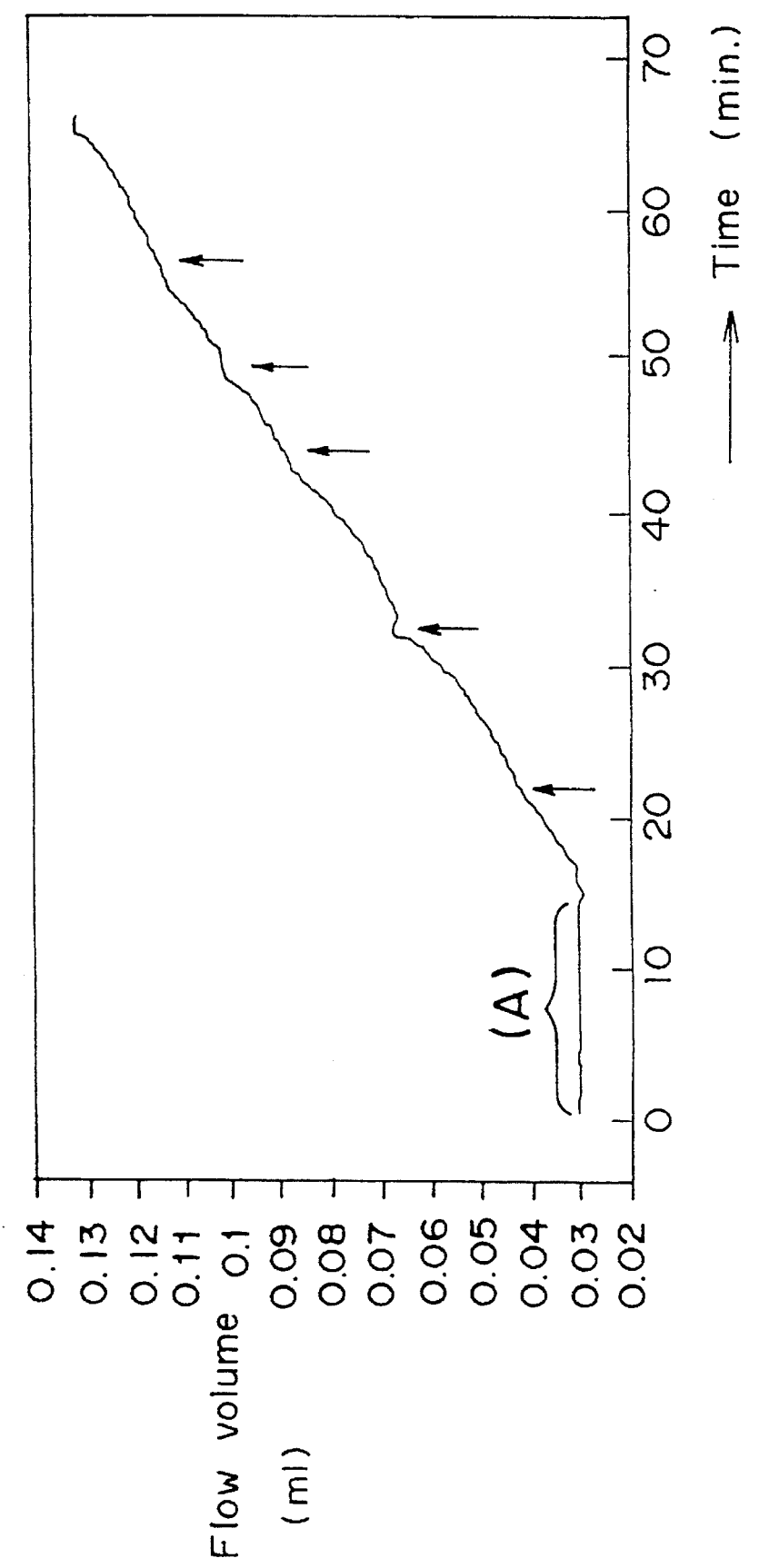
FIG. 27 is an explanatory view of a local change of flow rate in the conventional fluid infusion pump.

The upstream occlusion detection is also executed based on the change of pressure from the pressure sensor 16 in the same manner as in the downstream occlusion detecting operation. In detail, since the pressure inside the tube 23 is reduced when the tube 23 is occluded on the upstream side, the pressure exerted in the time when each of the fingers 20 starts to apply the pressure is reduced. Therefore, in a manner as shown in FIGS. 24A and 24B, by observing the phenomenon that a difference greater than a specified value takes place in the pressure value at a bottom portion in the change of pressure detected by the pressure sensor 16, the upstream occlusion is detected.

FIG. 25 is a flowchart of an upstream occlusion detecting operation executed under the control of the CPU 31. The following describes in detail the upstream occlusion detecting operation with reference to FIG. 25.

In step S251, it is decided whether or not the start switch is turned on. When the start switch is turned on, the program flow proceeds to step S252.

In step S252, the pulse output interval time of the motor drive pulse signal is set.

Then the contents of the count value CT and the address number N2 stored in the RAM 43 are initialized to "0".

In step S253, it is decided whether or not the output time exceeds a specified time. Consequently, when the output time exceeds the specified time, the program flow proceeds to step S254.

In step S254, one pulse of the pulses P of the motor drive pulse signal is supplied from the motor driver 38 to the stepping motor 39, and the count value CT of the amount of pulses supplied to the stepping motor 39 is incremented.

In step S255, a reference point in detecting the rotational position of the motor is obtained in the same manner as in step S215 through step S227 of the rotational position detecting operation of the eighth embodiment.

In step S256, the contents of the count value CT and the address number N2 are reset to "0".

In step S257, it is decided whether or not the output time exceeds the specified time. Consequently, when the output time has exceeded the specified time, the program flow proceeds to step S258.

In step S258, one pulse of the pulses P of the motor drive pulse signal is supplied from the motor driver 38 to the stepping motor 39, and the count value CT is incremented.

Then the pressure value from the pressure sensor 16 is taken in and set in the pressure value AT.

In step S259, it is decided whether or not a bottom exists in the pressure waveform in the vicinity of the concerned rotational position based on the pressure value AT taken in in step S255. Consequently, when a bottom exists, the program flow proceeds to step S260. Otherwise, the step S260 is skipped.

In step S260, the pressure value AT is set in the pressure value PB3[N2] stored in the address N2 of the corresponding table in the RAM 43, and the address number N2 is incremented.

In step S261, it is decided whether or not the content of the count value CT is not smaller than a value of 400. Consequently, when the content is not smaller than the value of 400, meaning that the stepping motor 39 has made one turn, the program flow proceeds to step S262. Otherwise, the program flow returns to step S257 to continue searching the bottom.

In step S262, the contents of the count value CT and the address number N2 are reset to "0".

In step S263, it is decided whether or not the output time exceeds the specified time. Consequently, when the output time exceeds the specified time, the program flow proceeds to step S264.

In step S264, one pulse of the pulses P of the motor drive pulse signal is supplied from the motor driver 38 to the stepping motor 39, and the count value CT is incremented.

Then the pressure value from the pressure sensor 16 is taken in and set in the pressure value AT.

In step S265, it is decided whether or not a bottom exists in the pressure waveform in the vicinity of the concerned rotational position based on the pressure value AT taken in in step S264. Consequently, when a bottom exists, the program flow proceeds to step S266. Otherwise, the program flow proceeds to step S269.

In step S266, the pressure value PB3[N2] at the previous bottom set in step S260 is set in a reference pressure value AP in the RAM 43, and the address number N2 is incremented.

In step S267, it is decided whether or not the present pressure value AT taken in from the pressure sensor 16 in step S264 is smaller than a value obtained by subtracting a value of "5" from the reference pressure value AP. Consequently, when the value AT is smaller than the obtained value, the program flow proceeds to step S268. Otherwise, the step S268 is skipped.

In the present tenth embodiment, each of the aforementioned pressure values is a digital value, and the digital value of "1" corresponds to $0.05$ kg/cm$^2$ as described hereinbefore. Since the pressure inside the tube 23 reduces when the upstream occlusion occurs, it is decided that the upstream occlusion has occurred when the pressure value AK in the time when each of the fingers 20 starts to be put in contact with the tube 23 (i.e., at the bottom) becomes smaller by a value greater than $0.25$ kg/cm$^2$ ("5" in digital value) than the reference pressure value (i.e., the pressure value at the previous bottom) AP.

In step S268, it is decided that the upstream occlusion has occurred, and therefore an upstream occlusion alarm is outputted to the I/O driver 34 to make the buzzer 36 issue an alarm sound.

In step S269, the fluid pumping operations are executed.

In step S270, it is decided whether or not the content of the count value CT is not smaller than a value of 400. Consequently, when the content is not smaller than the value of 400, meaning that the stepping motor 39 has made one turn, the program flow returns to step S262. Otherwise, the program flow proceeds to step S271.

In step S271, it is decided whether or not the upstream occlusion detecting operation is to be continued. Consequently, when the above-mentioned operation is continued, the program flow returns to step S263 to take in the next pressure value AT. Otherwise, the upstream occlusion detecting operation is completed.

In other words, according to the present tenth embodiment, the upstream occlusion deciding means is comprised of the step S258 through step S268.

According to the present tenth embodiment as described above, the upstream occlusion is detected by means of the pressure sensor 16 which is provided in opposition to the fluid pumping section 11 in the cover 15 in the same manner as in the downstream occlusion detecting operation as described hereinbefore. Therefore, the present tenth embodiment obviates the need of providing any pressure sensor specially for detecting the upstream occlusion on the upstream side of the fluid pumping section 11 or in the middle portion of the fluid pumping section 11 independently of the pressure sensor 16, which allows the fluid infusion pump to be easily compacted.

It is to be noted that the fluid infusion pump having the encoder 47 employed in the first embodiment can be also utilized in the eighth embodiment through the tenth embodiment.

As apparent from the above description, according to the fluid infusion pump of the present invention, the pressure force exerted from each of the fingers is detected by the pressure detecting means arranged in the inner wall of the cover within a mange of area in which the fore end portions of the fingers can press the tube to thereby output a detection signal. Within the above-mentioned arrangement, by observing the detection signal from the pressure detecting means, the possible erroneous placement of the tube, downstream occlusion, upstream occlusion and so forth can be detected by means of one sensor.

Therefore, the present invention allows the fluid infusion pump to be compacted with a reduced amount of sensors.

According to the fluid infusion pump of the present invention, the pressure force exerted from each of the fingers is detected by the pressure detecting means to which one end of the spring for urging the pressure plate placed in the inner wall of the cover in a range of area in which the fore end portions of the fingers can press the tube to thereby detect the detection signal. With the above-mentioned arrangement, by observing the detection signal from the pressure detecting means, the possible erroneous placement of the tube, downstream occlusion, upstream occlusion and so forth can be detected by means of one sensor.

Therefore, the present invention allows the fluid infusion pump to be compacted with a reduced amount of sensors.

According to the fluid infusion pump of one embodiment, the pressure detecting means is comprised of the pressure sensing plate which is distorted in compliance with the compression force of the spring and the load cell for detecting the distortion of the pressure sensing plate. With the above-mentioned arrangement, the pressure detecting means can be easily constructed.

According to the fluid infusion pump of one embodiment, the light travelling through the slits having different lengths and different intervals provided at the slit disk is detected by the photosensor, and the rotational position of the motor is detected by the rotational position detecting means based on the detection signal from the photosensor. With the above-mentioned arrangement, by detecting at least two slit edges, the rotational position of the motor can be detected.

Therefore, according to the embodiment, the rotational position of the motor can be detected before the motor makes one turn when the power is turned on.

According to the fluid infusion pump of one embodiment, the time interval between the inversion times in level of the detection signal from the photosensor is counted by the time counting means, and the slit length or the interval between slits is detected based on the count time to thereby specify the slit. With the above-mentioned arrangement, the slit can be easily specified by means of at least two slit edges to allow the rotational position of the motor to be speedily detected.

According to the fluid infusion pump of one embodiment, the amount of pulses supplied in the time interval between the inversion times in level of the detection signal from the photosensor is counted by the counter and the slit length or the interval between slits is detected based on the amount of pulses by the slit specifying means of the rotational position detecting means to thereby specify the slit. With the above-mentioned arrangement, the slit can be easily specified by means of at least two slit edges to allow the rotational position of the motor to be speedily detected.

According to the fluid infusion pump of one embodiment, the possible erroneous placement of the tube is subjected to a decision by the erroneous placement deciding means based on the detection signal from the pressure detecting means which can detect the pressure within the range in which the plural number of fingers can press the tube. With the above-mentioned arrangement, when the tube is displaced even a little bit from the range in which the plural number of fingers can press the tube, it can be decided that the tube is erroneously placed.

Therefore, the present embodiment can achieve the erroneous tube placement detection free from the dead zone.

According to the fluid infusion pump of one embodiment, the detection signal from the pressure detecting means is taken in by the erroneous placement deciding means in a cycle shorter than the cycle in which the fingers press the tube. With the above-mentioned arrangement, the pressure value relevant to the peak or the bottom of the pressure force exerted from each of the fingers can be securely taken in.

Therefore, the present embodiment can securely detect the erroneous placement of the tube.

According to the fluid infusion pump of one embodiment, the detection signal from the pressure detecting means is taken in by the erroneous placement deciding means in synchronization with the inversion in level of the detection signal from the photosensor. With the above-mentioned arrangement, the pressure value relevant to the peak or the bottom of the pressure force exerted from each of the fingers can be securely taken in in a cycle shorter than the cycle in which the fingers press the tube.

Therefore, the present embodiment can securely detect the erroneous placement of the tube.

According to the fluid infusion pump of one embodiment, the possible occurrence of the downstream occlusion is subjected to a decision by the downstream occlusion deciding means based on the detection signal from the pressure detecting means. With the above-mentioned arrangement, the possible occurrence of the downstream occlusion can be also detected by the pressure detecting means used for detecting the erroneous placement of the tube.

Therefore, the present embodiment obviates the need of providing any pressure detecting means for detecting the downstream occlusion, and therefore allows a compact fluid infusion pump to be provided.

According to the fluid infusion pump of one embodiment, the possible occurrence of the upstream occlusion is subjected to a decision by the upstream occlusion deciding means based on the detection signal from the pressure detecting means. With the above-mentioned arrangement, the upstream occlusion can be also detected by the pressure detecting means used for detecting the erroneous placement of the tube.

Therefore, the present embodiment obviates the need of providing any pressure detecting means for detecting the upstream occlusion, and therefore allows a compact fluid infusion pump to be provided.

According to the fluid infusion pump of one embodiment, the elapsed time from the time when one pulse of the drive pulses is supplied to the stepping motor is counted by the time counting means, while the pulse output interval time is set according to the rotational position by the time setting means. When the elapsed time reaches the pulse output interval time, one pulse of the drive pulses is supplied to the stepping motor to drive the motor by the motor driving means. With the above-mentioned arrangement, the rotating speed of the stepping motor can be controlled according to the rotational position of the motor.

Therefore, the present embodiment can eliminate the dead band condition by increasing the rotating speed of the stepping motor, for example, in the dead band. Furthermore, the pulse output interval time is set in optimum by the time setting means, with which the fluid flow is made linear to allow the fluid flow to be controlled with high accuracy.

In the above case, the dead band can be speedily detected by the rotational position detecting means before the motor makes one turn when the power is turned on. Thus the dead band is eliminated even in the time when the power is turned on to allow a stabilized fluid transfer to be always performed.

According to the fluid infusion pump of one embodiment, the duty ratio of the drive pulses is controlled by the duty ratio controlling means so that the duty ratio set by the duty ratio setting means according to the rotational position is achieved. With the above-mentioned arrangement, the motor driving torque can be controlled by controlling the current applied to the stepping motor.

Therefore, the present embodiment can control the driving torque of the stepping motor according to the rotational position of the motor.

Furthermore, the drive current is speedily reduced according to the required driving torque before the motor makes one turn when the power is turned on in combination with the operation of the rotational position detecting means to thereby allow the consumption current to be reduced. Thus the power battery can be compacted to allow the fluid infusion pump to be compacted.

According to the fluid infusion pump of one embodiment, the stepping motor is driven by the motor initial driving means until the next slit edge of the slit disk reaches the position in the vicinity of the photosensor. The stationary duty ratio is gradually increased by the duty ratio setting means until the detection signal from the photosensor is inverted in level to thereby set the duty ratio of the drive pulses at the duty ratio at which the necessary minimum drive current in the present rotational position is achieved. Then the stepping motor is driven by the motor driving means at the drive duty ratio based on the duty ratio set by the duty ratio setting means until the next slit edge but one of the slit disk reaches the position in the vicinity of the photosensor. With the above-mentioned arrangement, the drive duty ratio can be controlled in optimum according to the rotational position of the stepping motor.

Therefore, the present embodiment can reduce the consumption current by speedily reducing the drive current according to the required driving torque before the motor makes one turn in combination with the operation of the rotational position detecting means. Thus the power battery can be compacted to allow the fluid infusion pump to be compacted.

According to the fluid infusion pump of one embodiment, the duty ratio of the drive pulses is set at the inversion start duty ratio in the present rotational position by the inversion start duty ratio setting means. The duty ratio of the drive pulses is set at the duty ratio at which the necessary minimum drive current required in the time when the motor starts to be driven is achieved based on the inversion start duty ratio. Then the stepping motor starts to be driven at the drive duty ratio based on the duty ratio set by the duty ratio setting means. With the above-mentioned arrangement, the duty ratio in the time when the motor starts to be driven can be controlled in optimum according to the rotational position of the stepping motor.

Therefore, according to the present embodiment, the consumption current can be reduced by speedily reducing the drive current according to the stationary torque before the motor makes one turn when the power is turned on in combination with the operation of the rotational position detecting means. Thus the power battery can be compacted to allow the fluid infusion pump to be compacted.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A peristaltic fluid infusion pump having a main body and a cover securable to said main body, adapted to sandwich, between said main body and said cover, a flexible tube which is placed on a wall of said main body;

wherein said main body is formed with a generally semi-cylindrical groove for receiving said flexible tube;

said cover is formed with a recess which encloses a spring and with a pressure plate which is urged by said spring toward said groove in said main body whenever said cover is closed;

further comprising a plurality of fingers slidably received in a cavity formed in the wall and so aligned that respective fore end portions of said fingers sequentially engage respective axially adjacent portions of said flexible tube to compress said tube and to thereby transfer any medication fluid inside the tube longitudinally through said tube; and a pressure detector located adjacent said tube, on a surface of said pressure plate within a range of area in which the fore end portions of the fingers press the tube, said pressure plate being located on a side of said tube opposite said fingers and being urged, by said spring, toward the fingers against a pressure exerted by the fingers via the tube;

said pressure detector detecting the pressure exerted from each of the fingers via the tube, the pressure plate, and the spring, and outputting at least one detection signal representing said pressure.

2. A fluid infusion pump as claimed in claim 1, wherein the pressure detector comprises:

a pressure sensing plate, mounted on an end of the spring remote from the pressure plate, which distorts in response to compression force exerted by the spring; and a load cell mounted on, and detecting any distortion of, the pressure sensing plate.

3. A fluid infusion pump as claimed in claim 1, further comprising:

a slit disk which has slits having different respective circumferential lengths arranged in a circle at non-identical intervals, said slit disk being mounted on a shaft of a motor which drives the fingers via cams;

a photosensor which detects light travelling through any of the slits of the slit disk and outputs a detection signal;

and a rotational position detector which uniquely identifies each slit passing the photosensor, based on a detection signal outputted from the photosensor, thereby detecting a rotational position of the motor.

4. A fluid infusion pump as claimed in claim 3, further comprising:

time counting means for counting a time interval between a time when the detection signal from the photosensor is inverted in level, and a time when the detection signal is subsequently inverted in level, wherein the rotational position detector comprises slit specifying means detecting the length of the slit or the interval of the slits passing the photosensor, based on a time interval counted by the time counting means, and identifying the particular slit located in the position of the photosensor, based on a value of the detected length of interval.

5. A fluid infusion pump as claimed in claim 4, wherein the motor is a stepping motor, and the fluid infusion pump further comprises:

time counting means, counting an elapsed time from a time when a first one of said drive pulses is supplied to the stepping motor;

time setting means, setting a pulse output interval time by a predetermined method, according to the rotational position, of the stepping motor, detected by the rotational position detector; and motor driving means for driving the stepping motor by supplying one pulse of the drive pulses to the stepping motor when the elapsed time, counted by the time counting means, reaches the pulse output interval time.

6. A fluid infusion pump as claimed in claim 4, wherein the motor is a stepping motor, and the fluid infusion pump further comprises:

duty ratio setting means for setting a duty ratio of drive pulses to be supplied to the stepping motor, according to the rotational position, of the stepping motor, detected by the rotational position detecting means; and duty ratio controlling means, controlling the duty ratio of the drive pulses so that the duty ratio, commanded by the duty ratio setting means, is achieved, whereby a motor driving torque is controlled by controlling a current applied to the stepping motor.

7. A fluid infusion pump as claimed in claim 4, wherein the motor is a stepping motor, and the fluid infusion pump further comprises:

motor initial driving means, driving the stepping motor, until an edge of a next slit of the slit disk reaches a position in the vicinity of the photosensor, by supplying a predetermined number of pulses, having a duty ratio set by a predetermined method, to the stepping motor according to the rotational position, of the stepping motor, detected by the rotational position detector;

duty ratio setting means, setting the duty ratio, of the drive pulses to be supplied to the stepping motor located in a rotational position such that the edge of the next slit of the slit disk reaches a position in the vicinity of the photosensor, at a stationary duty ratio, at which a minimum current assuring a stationary torque is achieved, according to the rotational position of the stepping motor, and thereafter setting the duty ratio of the drive pulses at a duty ratio, at which a necessary minimum drive current in a present rotational position is achieved, by successively supplying, to the stepping motor, drive pulses having a duty ratio obtained by gradually increasing the set stationary duty ratio, until the detection signal from the photosensor is inverted in level; and motor driving means driving the stepping motor until an edge of a next-slit-but-one of the slit disk reaches a position in the vicinity of the photosensor by supplying, to the stepping motor, drive pulses having a drive duty ratio set, based on the duty ratio set by the ratio setting means.

8. A fluid infusion pump as claimed in claim 4, wherein the motor is a stepping motor, and the fluid infusion pump further comprises:

reversing start duty ratio setting means setting a stationary duty ratio, according to the rotational position, of the stepping motor, detected by the rotational position detector, and setting the duty ratio of the drive pulses at a reversing start duty ratio at which a drive current, for making the stepping motor start to reverse in a present rotational position, is achieved by successively supplying, to the stepping motor, drive pulses having a duty ratio obtained by gradually reducing the set stationary duty ratio, until the detection signal from the photosensor is inverted in level;

duty ratio setting means setting the duty ratio of the drive pulses at a duty ratio at which a minimum drive current, necessary in a time when the stepping motor starts to be driven, is achieved by successively supplying, to the stepping motor, drive pulses, having a duty ratio obtained by gradually increasing the reversing start duty ratio set by the reversing start duty ratio setting means, until the detection signal from the photosensor is inverted in level; and motor driving means, making the stepping motor start to be driven, by supplying, to the stepping motor, drive pulses having a drive duty ratio set, based on the duty ratio set by the duty ratio setting means.

9. A fluid infusion pump as claimed in claim 3, wherein the motor is a stepping motor, and further comprising a counter which counts the number of drive pulses supplied to the stepping motor in a time interval between a time when the detection signal from the photosensor is inverted in level and a time when the detection signal is subsequently inverted in level; and wherein the rotational position detector comprises slit specifying means detecting the length of the slit or the interval of the slits passing the photosensor, based on the number of pulses counted by said counter, and identifying the particular slit located in the position of the photosensor, based on a value of the detected length or interval.

10. A fluid infusion pump as claimed in claim 1, further comprising:

erroneous placement deciding means which monitors any change of pressure force exerted from the fingers by receiving a detection signal from the pressure detector, and when at least one of a peak and a bottom of the pressure force is not greater than a predetermined level, deciding that the tube is not correctly placed, in a position where the tube will be pressed by the fingers.

11. A fluid infusion pump as claimed in claim 10, wherein the erroneous placement deciding means samples the detection signal from the pressure detector at a time interval shorter than a cycle during which all of said fingers press the tube.

12. A fluid infusion pump having the photosensor as claimed in claim 11, and further comprising:

a slit disk which has slits having different respective circumferential lengths arranged in a circle at non-identical intervals, said slit disk being mounted on a shaft of a motor which drives the fingers via cams;

a photosensor which detects light travelling through any of the slits of the slit disk and outputs a detection signal; and a rotational position detector identifying the particular slit located in a position of the photosensor, based on a detection signal outputted from the photosensor, and thereby detecting a rotational position of the motor, and wherein the erroneous placement deciding means samples the detection signal from the pressure detecting means in synchrony with an inversion in level of the detection signal from the photosensor.

13. A fluid infusion pump as claimed in claim 1, further comprising:

downstream occlusion deciding means monitoring the pressure force exerted from each of the fingers by sampling the detection signal from the pressure detector, and when the pressure force increases in level to reach a predetermined level, deciding that downstream occlusion has occurred.

14. A fluid infusion pump as claimed in claim 1, further comprising:

upstream occlusion deciding means monitoring any change in the pressure exerted from each of the fingers by sampling the detection signal from the pressure detector, and when a bottom level in the change of the pressure fails to reach a predetermined value, deciding that an upstream occlusion has occurred.

15. A fluid infusion pump, having a main body and a cover securable to said main body, adapted to sandwich, between said main body and said cover, a flexible tube which is placed on a wall of said main body;

wherein said main body is formed with a generally semi-cylindrical groove for receiving said flexible tube;

said cover is formed with a recess which encloses a spring and a pressure plate which is urged by said spring toward said groove in said main body whenever said cover is closed;

further comprising a plurality of fingers slidably received in a cavity formed in the wall and so aligned that respective fore end portions of said fingers sequentially engage respective axially adjacent portions of said flexible tube to compress said tube and to thereby transfer any medication fluid inside the tube longitudinally through said tube;

a motor which drives said fingers via respective cams;

a slit disk, mounted on a common shaft with said motor, and formed with a plurality of slits of differing circumferential length;

a photosensor which detects light travelling through any of the slits of the slit disk and outputs a detection signal;

a rotational position detector, coupled to an output of said photosensor, which determines rotational position of said motor, based upon said photosensor detection signal, said detector including a timer which measures a time interval between successive inversions of said detection signal and a table associating specific slits with respective time intervals; and a pressure detector located adjacent said tube, on a surface of said pressure plate within a range of area in which the fore end portions of the fingers press the tube, detecting the pressure exerted from each of the fingers via the tube, the pressure plate, and the spring, and outputting at least one detection signal representing said pressure;

wherein the motor is a stepping motor, and the fluid infusion pump further comprises:

motor initial driving means driving the stepping motor, until an edge of a next slit of the slit disk reaches a position in the vicinity of the photosensor, by supplying a specified number of pulses, having a duty ratio set by a predetermined method, to the stepping motor, according to the rotational position of the stepping motor detected by the rotational position detector;

duty ratio setting means setting the duty ratio, of the drive pulses to be supplied to the stepping motor located in a rotational position such that the edge of the next slit of the slit disk reaches a position in the vicinity of the photosensor, at a stationary duty ratio at which a minimum current, assuring a stationary torque, is achieved by a predetermined method, according to the rotational position of the stepping motor, and thereafter setting the duty ratio of the drive pulses at a duty ratio at which a necessary minimum drive current, in a present rotational position, is achieved by successively supplying, to the stepping motor, drive pulses having a duty ratio obtained by gradually increasing the set stationary duty ratio, until the detection signal from the photosensor is inverted in level; and motor driving means, driving the stepping motor until an edge of a next-slit-but-one of the slit disk reaches a position in the vicinity of the photosensor by supplying, to the stepping motor, drive pulses having a drive duty ratio set according to a predetermined procedure, based on the duty ratio set by the duty ratio setting means.

16. A fluid infusion pump, having a main body and a cover securable to said main body, adapted to sandwich, between said main body and said cover, a flexible tube which is placed on a wall of said main body;

wherein said main body is formed with a generally semi-cylindrical groove for receiving said flexible tube;

said cover is formed with a recess which encloses a spring and a pressure plate which is urged by said spring toward said groove in said main body whenever said cover is closed;

further comprising a plurality of fingers slidably received in a cavity formed in the wall and so aligned that respective fore end portions of said fingers sequentially engage respective axially adjacent portions of said flexible tube to compress said tube and to thereby transfer any medication fluid inside the tube longitudinally through said tube;

a motor which drives said fingers via respective cams;

a slit disk, mounted on a common shaft with said motor, and formed with a plurality of slits of differing circumferential length;

a photosensor which detects light travelling through any of the slits of the slit disk and outputs a detection signal;

a rotational position detector, coupled to an output of said photosensor, which determines rotational position of said motor, based upon said photosensor detection signal, said detector including a timer which measures a time interval between successive inversions of said detection signal and a table associating specific slits with respective time intervals; and a pressure detector located adjacent said tube, on a surface of said pressure plate within a range of area in which the fore end portions of the fingers press the tube, detecting the pressure exerted from each of the fingers via the tube, the pressure plate, and the spring, and outputting at least one detection signal representing said pressure;

wherein the motor is a stepping motor, and the fluid infusion pump further comprises:

reversing start duty ratio setting means, setting a stationary duty ratio by a predetermined method according to the rotational position, of the stepping motor, detected by the rotational position detecting means, and setting the duty ratio of the drive pulses at a reversing start duty ratio, at which a drive current, for making the stepping motor start to reverse in a present rotational position, is achieved by successively supplying, to the stepping motor, drive pulses having a duty ratio obtained by gradually reducing the set stationary duty ratio, until the detection signal from the photosensor is inverted in level;

duty ratio setting means, setting the duty ratio of the drive pulses at a duty ratio at which a minimum drive current necessary, in a time when the stepping motor starts to be driven, is achieved by successively supplying, to the stepping motor, drive pulses having a duty ratio obtained by gradually increasing the reversing start duty ratio, set by the reversing start duty ratio setting means, until the detection signal from the photosensor is inverted in level; and motor driving means, making the stepping motor start to be driven by supplying, to the stepping motor, drive pulses having the drive duty ratio set, according to a predetermined procedure, based on the duty ratio set by the duty ratio setting means.

* * * * *